(12) United States Patent
Privitera et al.

(10) Patent No.: US 10,869,668 B2
(45) Date of Patent: *Dec. 22, 2020

(54) SURGICAL DEVICE

(71) Applicant: AtriCure, Inc., Mason, OH (US)

(72) Inventors: Salvatore Privitera, Mason, OH (US);
James David Hughett, Sr., Monroe, GA (US); Keith Edward Martin, Dayton, OH (US)

(73) Assignee: AtriCure, Inc., Mason, OH (US)

( * ) Notice: Subject to any disclaimer, the term of this patent is extended or adjusted under 35 U.S.C. 154(b) by 591 days.

This patent is subject to a terminal disclaimer.

(21) Appl. No.: 14/989,985

(22) Filed: Jan. 7, 2016

(65) Prior Publication Data
US 2016/0113656 A1 Apr. 28, 2016

Related U.S. Application Data

(63) Continuation of application No. 13/586,737, filed on Aug. 15, 2012, now Pat. No. 9,265,486.

(60) Provisional application No. 61/523,805, filed on Aug. 15, 2011.

(51) Int. Cl.
| | |
|---|---|
| *A61B 17/04* | (2006.01) |
| *A61B 17/10* | (2006.01) |
| *A61B 17/122* | (2006.01) |
| *A61B 17/128* | (2006.01) |
| *A61B 17/00* | (2006.01) |
| *A61B 17/08* | (2006.01) |

(52) U.S. Cl.
CPC .............. *A61B 17/10* (2013.01); *A61B 17/00* (2013.01); *A61B 17/00234* (2013.01); *A61B 17/083* (2013.01); *A61B 17/1227* (2013.01); *A61B 17/1285* (2013.01); *A61B 2017/00367* (2013.01)

(58) Field of Classification Search
CPC .......... A61B 17/00234; A61B 17/1285; A61B 17/1227; A61B 17/10; A61B 17/00; A61B 17/083; A61B 2017/00367
USPC ....... 606/1, 34, 51, 139, 141, 142, 143, 151, 606/157, 158, 205, 207
See application file for complete search history.

(56) References Cited

U.S. PATENT DOCUMENTS 7,424,965 B2 * 9/2008 Racenet .......... A61B 17/07207
227/180.1

* cited by examiner

*Primary Examiner* — Vy Q Bui
(74) *Attorney, Agent, or Firm* — Dorton & Willis LLP; Ryan Willis

(57) ABSTRACT

A medical instrument comprising: (A) a first joint comprising a first member and a second member, the first member configured to be repositionable with respect to the second member in an X-Y plane; (B) a second joint operatively coupled to the first joint, the second joint comprising a third member and a fourth member, the third member configured to be repositionable with respect to the fourth member in a Y-Z plane perpendicular to the X-Y plane; and, (C) a controller operatively coupled to the first joint and the second joint, the controller including a first control configured to direct repositioning of at least one of the first member and the second member, and a second control configured to direct repositioning of at least one of the third member and the fourth member.

16 Claims, 70 Drawing Sheets

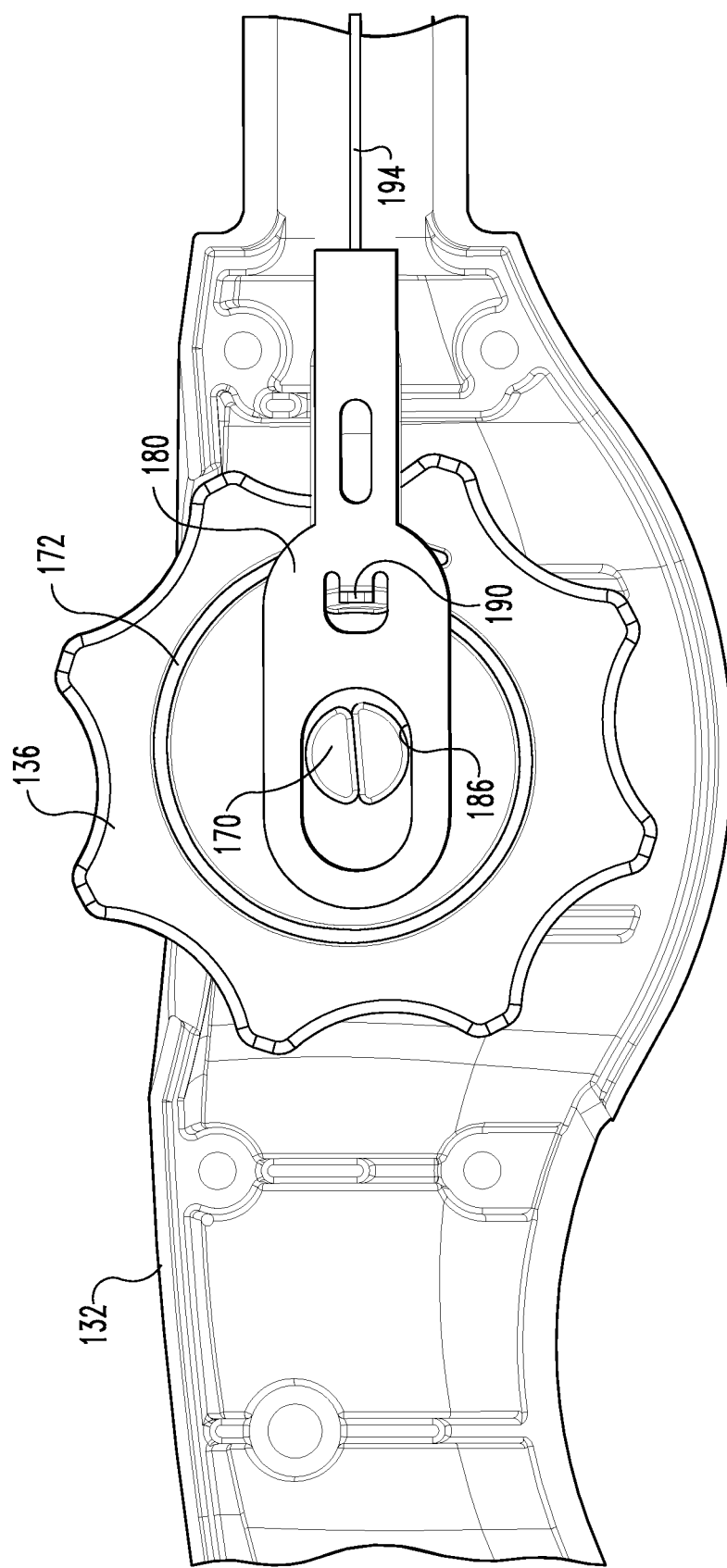

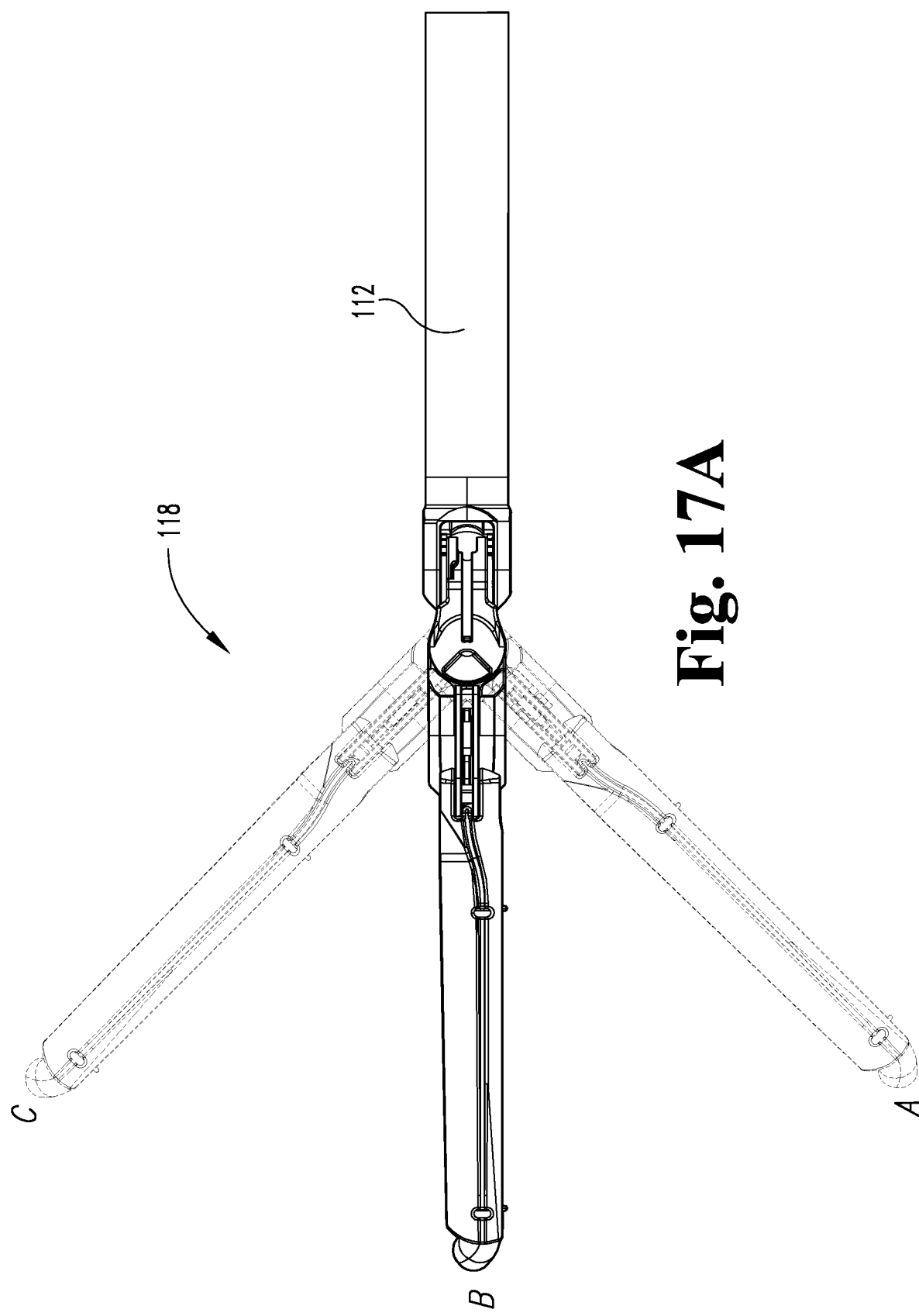

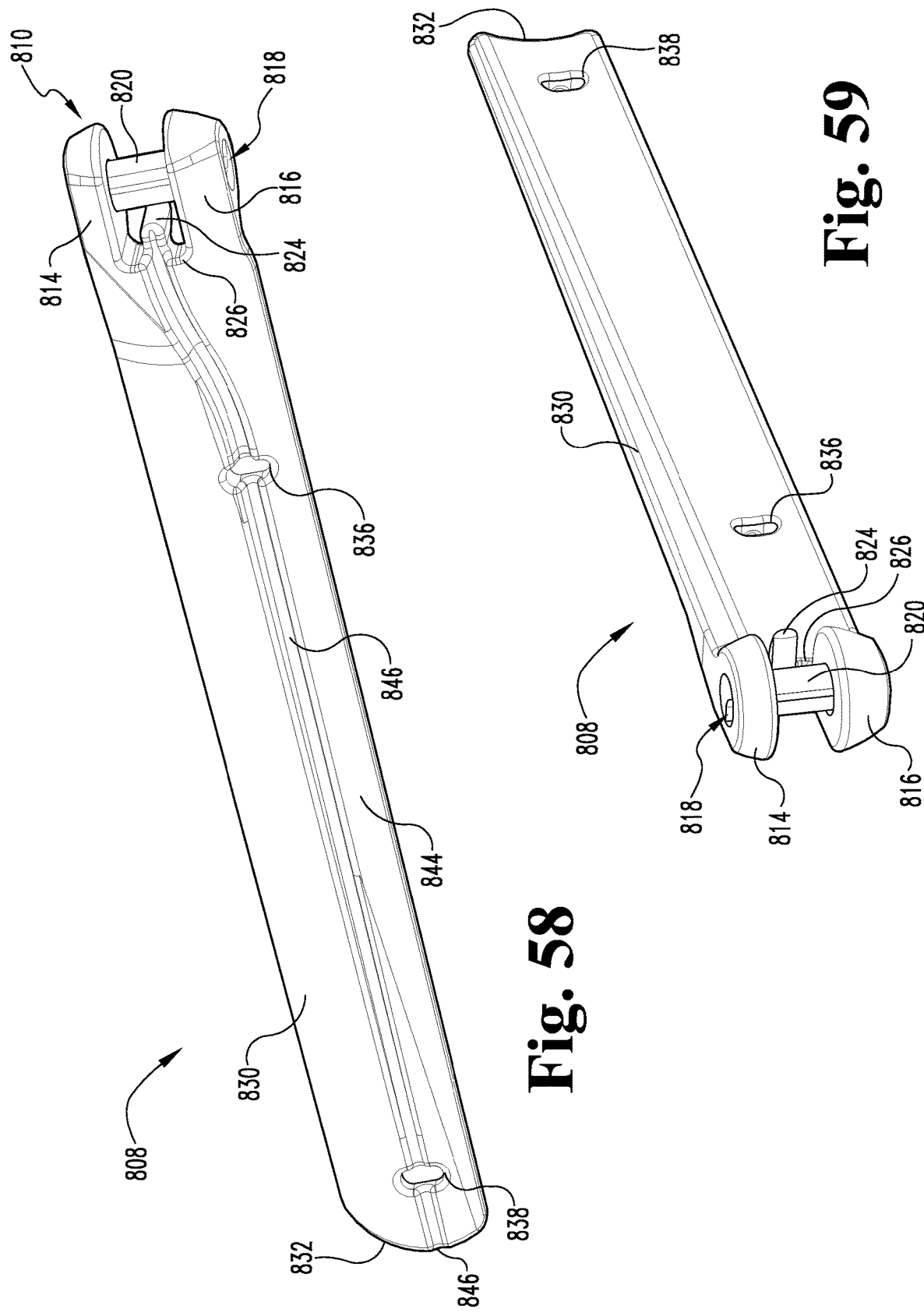

SURGICAL DEVICE

CROSS REFERENCE TO RELATED APPLICATIONS

The present application is a continuation of U.S. Nonprovisional patent application Ser. No. 13/586,737, titled "SURGICAL DEVICE" and filed on Aug. 15, 2012, now U.S. Pat. No. 9,265,486, which claims the benefit of U.S. Provisional Patent Application Ser. No. 61/523,805, titled "LAPAROSCOPIC DEVICE," which was filed on Aug. 15, 2011, the disclosure of which is hereby incorporated by reference.

RELATED ART

Field of the Invention

The present invention is directed to surgical equipment and, more specifically, to surgical equipment that may be used in minimally invasive procedures. The disclosure also relates to surgical equipment to facilitate the positioning and deployment of an atrial appendage occlusion device. In addition, the disclosure relates to surgical equipment that is adapted to accommodate or work in tandem with flexible endoscopes.

INTRODUCTION TO THE INVENTION

The exemplary embodiments disclosed herein include one or more active or passive repositioning mechanisms. As will be discussed in more detail hereafter, an active repositioning mechanism provides for infinite adjustments as the user is physically operating a control to directly manipulate the repositioning of an end effector. In contrast, a passive repositioning mechanism can be thought of as acting similar to a light switch, either off or on. In this manner, the passive repositioning mechanism either allows or disallows repositioning of the end effector, but is not responsible for actively manipulating the position of the end effector. Put another way, the passive repositioning system allows for free movement of the end effector within the end effector's range of motion when the mechanism is in the "on" position, but locks movement of the end effector within the end effector's range of motion when the mechanism is in the "off" position. In exemplary form, a laparoscopic device may incorporate both an active and a passive repositioning mechanism to control movements in different directions, such as pitch and yaw.

The exemplary embodiments also include active repositioning mechanisms that provide a certain motion conversion. In other words, a ninety degree change in position of the controller would result in a forty-five degree change in position at the end effector. As disclosed herein, certain parameters may be modified to provide different motion conversion depending upon the end application and user preference.

It is a first aspect of the present invention to provide a medical instrument comprising: (a) a first joint comprising a first member and a second member, the first member configured to be repositionable with respect to the second member in an X-Y plane; (b) a second joint operatively coupled to the first joint, the second joint comprising a third member and a fourth member, the third member configured to be repositionable with respect to the fourth member in a Y-Z plane perpendicular to the X-Y plane; and, (c) a controller operatively coupled to the first joint and the second joint, the controller including a first control configured to direct repositioning of at least one of the first member and the second member, and a second control configured to direct repositioning of at least one of the third member and the fourth member.

In a more detailed embodiment of the first aspect, the first control comprises a passive control configured to be repositionable between a first position, that allows free movement between the first member and the second member within the X-Y plane, and a second position that retards movement between the first member and the second member within the X-Y plane, and the second control comprises an active control configured to be repositionable among an infinite number of positions, where each of the infinite number of positions orients the third member with respect to the fourth member in a different position within the Y-Z plane. In yet another more detailed embodiment, the passive control includes a lever repositionably mounted to a housing of the controller, the lever coupled to a passive control line, and the passive control line is also coupled to a repositionable catch configured to engage at least one of the first member and the second member to retard movement between the first member and the second member within the X-Y plane. In a further detailed embodiment, the repositionable catch is biased, using a spring, to retard movement between the first member and the second member within the X-Y plane, and the lever is configured to be repositionable to tension the passive control line to overcome the bias of the spring to allow movement between the first member and the second member within the X-Y plane. In still a further detailed embodiment, the instrument further includes a longitudinal conduit extending between the controller and the first joint, wherein at least a portion of the passive control line extends through the longitudinal conduit. In a more detailed embodiment, the instrument further includes a longitudinal conduit extending between the controller and the first joint, where the first member is mounted to the controller, and the second member is repositionably mounted to the first member. In a more detailed embodiment, the first member is elongated and includes an internal cavity that at least partially houses a repositionable catch to retard movement between the first member and the second member within the X-Y plane, and at least one of the first member and the longitudinal conduit houses a spring biasing the repositionable catch to retard movement between the first member and the second member within the X-Y plane. In another more detailed embodiment, at least one of the first member and the second member includes a projection, at least one of the first member and the second member includes a cavity configured to receive the projection, the cavity is at least partially defined by a bearing surface, and the projection is configured to contact the bearing surface when movement occurs between the first member and the second member within the X-Y plane. In yet another more detailed embodiment, the first member includes the cavity, the second member includes the projection, the repositionable catch includes at least one tooth, and the second member includes at least one tooth configured to engage the at least one tooth of the repositionable catch to retard movement between the first member and the second member within the X-Y plane. In still another more detailed embodiment, the cavity comprises a first cavity and a second cavity spaced apart and facing one another, the projection comprises a first projection and a second projection spaced apart and facing away from one another, the first cavity is configured to receive the first projection, and the second cavity is configured to receive the second projection.

In yet another more detailed embodiment of the first aspect, the first member comprises a clevis, and the second member comprises a pelvis. In still another more detailed embodiment, the first control comprises a passive control configured to be repositionable between a first position, that allows free movement between the first member and the second member within the X-Y plane, and a second position that retards movement between the first member and the second member within the X-Y plane, the clevis includes an internal cavity that at least partially receives a repositionable catch and a bias spring, the repositionable catch comprises a portion of the first control, the first control also includes an actuator repositionable mounted to the controller, and the first control further includes a tether concurrently coupled to the actuator and the repositionable catch. In a further detailed embodiment, the pelvis includes a first pelvis half and a second pelvis half, and the first pelvis half and the second pelvis half are identical. In still a further detailed embodiment, the active control includes an actuator repositionably mounted to a housing of the controller, the actuator operatively coupled to an active control line, and the active control line is coupled to at least one of the third member and the fourth member to control movement between the third member and the fourth member within the Y-Z plane. In a more detailed embodiment, the actuator includes a wheel and a link plate, the wheel includes a spiral cavity, and the linkplate includes a projection configured to be received within the spiral cavity of the wheel. In a more detailed embodiment, the actuator includes a wheel and a link plate, the linkplate includes a spiral cavity, and the wheel includes a projection configured to be received within the spiral cavity of the linkplate. In another more detailed embodiment, the actuator includes a wheel and a link plate, the linkplate includes a cavity, and the wheel includes a spiral projection configured to be received within the cavity of the linkplate. In yet another more detailed embodiment, the actuator includes a wheel and a link plate, the wheel includes a cavity, and the linkplate includes a spiral projection configured to be received within the cavity of the wheel.

In a more detailed embodiment of the first aspect, the second control comprises an active control configured to be repositionable among an infinite number of positions, where each of the infinite number of positions orients the third member with respect to the fourth member in a different position within the Y-Z plane, the second member is mounted to the third member, and the third member is repositionably mounted to the fourth member. In yet another more detailed embodiment, the fourth member is elongated and includes an internal cavity that at least partially houses a repositionable pull link, and the fourth member includes a channel configured to receive at least a portion of the active control line. In a further detailed embodiment, the channel includes a first arcuate segment and a second arcuate segment, the active control line includes a first active control line and a second active control line, the first arcuate segment is configured to receive the first active control line, the second arcuate segment is configured to receive the second active control line, at least a portion of the first active control line is secured to the fourth member, and at least a portion of the second active control line is secured to the fourth member. In still a further detailed embodiment, at least one of the third member and the fourth member includes a projection, at least one of the third member and the fourth member includes a cavity configured to receive the projection, the cavity is at least partially defined by a bearing surface, and the projection is configured to contact the bearing surface when movement occurs between the third member and the fourth member within the Y-Z plane. In a more detailed embodiment, the fourth member includes the cavity, and the third member includes the projection. In a more detailed embodiment, the cavity comprises a first cavity and a second cavity spaced apart and facing away from one another, the projection comprises a first projection and a second projection spaced apart and facing one another, the first cavity is configured to receive the first projection, and the second cavity is configured to receive the second projection. In another more detailed embodiment, the second control comprises an active control configured to be repositionable among an infinite number of positions, where each of the infinite number of positions orients the third member with respect to the fourth member in a different position within the Y-Z plane, the third member comprises a pelvis, and the fourth member comprises a yoke. In yet another more detailed embodiment, the active control includes an actuator repositionably mounted to a housing of the controller, the actuator operatively coupled to a first active control line and a second active control line, the yoke includes an internal cavity that at least partially receives a repositionable pull link, the yoke includes a first channel configured to receive at least a portion of the first active control line, and a second configured to receive at least a portion of the second active control line, at least a portion of the first active control line and the second active control line are secured to the yoke. In still another more detailed embodiment, the second member and the third member are mounted to one another, and the second member and the third member cooperate to forma pelvis.

In yet another more detailed embodiment of the first aspect, the actuator includes a first wheel, a first link plate, a second wheel, and a second link plate, the first and second wheels each include a spiral cavity, the first and second linkplates each include a projection configured to be received within a respective spiral cavity of the first and second wheels, the first active control line is coupled to the first link plate, and the second active control line is coupled to the second link plate. In still another more detailed embodiment, the first wheel is a mirror image of the second wheel. In a further detailed embodiment, the spiral cavity of each of the first and second wheels includes an arcuate wall that delineates the spiral cavity, and the projection of each of the first and second link plates includes a curved surface that is configured to contact the arcuate wall of a respective spiral cavity. In still a further detailed embodiment, the first control comprises a first passive control configured to be repositionable between a first position, that allows free movement between the first member and the second member within the X-Y plane, and a second position that inhibits movement between the first member and the second member within the X-Y plane, and the second control comprises a second passive control configured to be repositionable between a first position, that allows free movement between the third member and the fourth member within the Y-Z plane, and a second position that inhibits movement between the third member and the fourth member within the Y-Z plane. In a more detailed embodiment, the first passive control includes an actuator repositionably mounted to a housing of the controller, the actuator coupled to a first passive control line, and the first passive control line is also coupled to at least one of the first member and the second member to retard movement between the first member and the second member within the X-Y plane. In a more detailed embodiment, the actuator is configured to be repositionable to allow movement between the first member and the second member within the X-Y plane. In another more detailed embodiment, In yet another more detailed embodiment, the first member is elongated and includes an internal cavity that at least partially houses a repositionable catch to retard movement between the first member and the second member within the X-Y plane, and at least one of the first member and the longitudinal conduit houses a spring biasing the repositionable catch to retard movement between the first member and the second member within the X-Y plane.

In a more detailed embodiment of the first aspect, at least one of the first member and the second member includes a projection, at least one of the first member and the second member includes a cavity configured to receive the projection, the cavity is at least partially defined by a bearing surface, and the projection is configured to contact the bearing surface when movement occurs between the first member and the second member within the X-Y plane. In yet another more detailed embodiment, the first member includes the cavity, the second member includes the projection, the repositionable catch includes at least one tooth, and the second member includes at least one tooth configured to engage the at least one tooth of the repositionable catch to retard movement between the first member and the second member within the X-Y plane. In a further detailed embodiment, the cavity comprises a first cavity and a second cavity spaced apart and facing one another, the projection comprises a first projection and a second projection spaced apart and facing away from one another, the first cavity is configured to receive the first projection, and the second cavity is configured to receive the second projection. In still a further detailed embodiment, the first member comprises a clevis, and the second member comprises a pelvis. In a more detailed embodiment, the clevis includes an internal cavity that at least partially receives a repositionable catch and a bias spring, the repositionable catch comprises a portion of the first control, the first control also includes an actuator repositionable mounted to the controller, and the first control further includes a tether concurrently coupled to the actuator and the repositionable catch. In a more detailed embodiment, the pelvis includes a first pelvis half and a second pelvis half, and the first pelvis half and the second pelvis half are identical. In another more detailed embodiment, the second control includes an actuator repositionably mounted to a housing of the controller, the actuator operatively coupled to a passive control line, and the passive control line is coupled to at least one of the third member and the fourth member to control movement between the third member and the fourth member within the Y-Z plane. In yet another more detailed embodiment, the actuator includes a depressible button extending through the housing of the controller that is configured to engage a receiver, the actuator includes at least one tooth, and the receiver includes a at least one tooth configured to selectively engage the at least one tooth of the actuator. In still another more detailed embodiment, an actuator is repositionably mounted to a housing of the controller, the actuator comprising a portion of the first control and a portion of the second control, the first passive control includes a first receiver repositionably mounted to the housing of the controller, the first receiver operatively coupled to a first line mounted to at least one of the first member and the second member, and the second passive control includes a second receiver repositionably mounted to the housing of the controller, the second receiver operatively coupled to a second line mounted to at least one of the third member and the fourth member.

In yet another more detailed embodiment of the first aspect, the actuator comprises a depressible button that is biased by a spring, the actuator configured to be repositionable between a first position and a second position, the first position allows free movement between the first member and the second member within the X-Y plane and allows free movement between the third member and the fourth member within the Y-Z plane, the second position retards free movement between the first member and the second member within the X-Y plane and retards free movement between the third member and the fourth member within the Y-Z plane, the actuator is lockable in the first position, the actuator does not engage the first receiver or the second receiver in the first position, and, the actuator engages the first receiver and the second receiver in the second position. In still another more detailed embodiment, the actuator comprises a depressible button that is biased by a spring to engage the first receiver and the second receiver, the first and second receivers are rotationally repositionable along a common spool extending internally within the controller when not engaged by the depressible button, and the first and second receivers are not rotationally repositionable along the common spool when engaged by the depressible button. In a further detailed embodiment, the instrument further includes an end effector operatively coupled to the first and second joints. In still a further detailed embodiment, the end effector comprises at least one of a surgical dissector, an ablation pen, an occlusion clip, an occlusion clip applicator, surgical forceps, surgical jaws, a linear cutter, an ablation clamp, and an ablation rail. In a more detailed embodiment, the controller includes a third control operatively coupled to the end effector. In a more detailed embodiment, the end effector comprises a clip deployment device, and the third control includes a link that extends from the controller to the end effector to control repositioning of at least a portion of the clip deployment device. In another more detailed embodiment, the clip deployment device include opposing jaws removably coupled to an occlusion clip, and the link is configured to be repositioned to remove the occlusion clip from being coupled to the opposing jaws. In yet another more detailed embodiment, the opposing jaws each include an orifice through which a tether extends, the tethers are coupled to the occlusion clip, and the link is removable coupled to the tethers.

In yet another more detailed embodiment of the first aspect, the tether comprises a suture loop, and the link interposes the suture loop and the occlusion clip. In yet another aspect of the invention, the end effector comprises a clip deployment device, and the third control includes a link that extends from the controller to the end effector to control repositioning of at least a portion of the clip deployment device. Moreover, in yet another detailed embodiment, the second joint includes a channel along which a pull link is configured to traverse, the pull link being operatively coupled to the third control and the clip deployment device, and the deployment device including at least two link clips operatively coupled to the pull link, each of the at least two link clips having a non-circular cam that rides upon a camming surface of at least one of two jaws, the at least two link clips configured to pivot with respect to the two jaws until interaction between the cam and camming surface inhibits further pivoting.

It is a second aspect of the present invention to provide a medical instrument comprising: (a) a controller at least partially housing a plurality of controls; (b) an elongated conduit operatively coupling the controller to a first joint and a second joint; (c) a first joint comprising a first member and a second member, the first member configured to be repositionable with respect to the second member in an X-Y plane; (d) a second joint operatively coupled to the first joint, the second joint comprising a third member and a fourth member, the third member configured to be repositionable with respect to the fourth member in a Y-Z plane perpendicular to the X-Y plane; and, (e) an end effector operatively coupled to the first and second joints, where the plurality of controls includes a first control operatively coupled to the first joint to control motion of the first member with respect to the second member in the X-Y plane, a second control operatively coupled to the second joint to control motion of the third member with respect to the fourth member in the Y-Z plane, a third control operatively coupled to the end effector control motion of at least a portion of the end effector.

In a more detailed embodiment of the second aspect, the instrument further includes an occlusion clip removably mounted to the end effector, wherein the plurality of controls includes a fourth control to dismount the occlusion clip from the end effector. In yet another more detailed embodiment, the first control comprises a passive control configured to be repositionable between a first position, that allows free movement between the first member and the second member within the X-Y plane, and a second position that retards movement between the first member and the second member within the X-Y plane, and the second control comprises an active control configured to be repositionable among an infinite number of positions, where each of the infinite number of positions orients the third member with respect to the fourth member in a different position within the Y-Z plane. In a further detailed embodiment, the third control comprises a second active control configured to be repositionable among an infinite number of positions, where each of the infinite number of positions orients the end effector in a different position. In still a further detailed embodiment, the instrument further includes an occlusion clip removably mounted to the end effector, wherein the plurality of controls includes a fourth control to dismount the occlusion clip from the end effector, wherein the fourth control comprises a passive control configured either dismount or retain a connection between the end effector and the occlusion clip. In a more detailed embodiment, the first control comprises a first passive control configured to be repositionable between a first position, that allows free movement between the first member and the second member within the X-Y plane, and a second position that retards movement between the first member and the second member within the X-Y plane, and the second control comprises a second control configured to be repositionable between a first position, that allows free movement between the third member and the fourth member within the Y-Z plane, and a second position that retards movement between the third member and the fourth member within the Y-Z plane. In a more detailed embodiment, the third control comprises an active control configured to be repositionable among an infinite number of positions, where each of the infinite number of positions orients the end effector in a different position.

In yet another more detailed embodiment of the second aspect, the first control comprises a first passive control configured to be repositionable between a first position, that allows free movement between the first member and the second member within at least ninety degrees of the X-Y plane, and a second position that retards movement between the first member and the second member within the X-Y plane, and the second control comprises a second control configured to be repositionable between a first position, that allows free movement between the third member and the fourth member within at least ninety degrees of the Y-Z plane, and a second position that retards movement between the third member and the fourth member within the Y-Z plane. In still another more detailed embodiment, the first control comprises a passive control configured to be repositionable between a first position, that allows free movement between the first member and the second member within at least ninety degrees of the X-Y plane, and a second position that retards movement between the first member and the second member within the X-Y plane, and the second control comprises an active control configured to be repositionable among an infinite number of positions within at least ninety degrees of the Y-Z plane, where each of the infinite number of positions orients the third member with respect to the fourth member in a different position within the Y-Z plane. In a further detailed embodiment, the active control includes a first wheel having a first spiral cavity formed therein and a second wheel having a second spiral cavity formed therein, the first and second spiral cavities being mirror images of one another, the active control also includes a first link plate coupled to a first link line and a second link place coupled to a second link line, the first link plate includes a first projection configured to be received within the first spiral cavity, the second link plate includes a second projection configured to be received within the second spiral cavity, the first wheel and second wheel are coupled to one another so that rotation of one wheel results in corresponding rotation of the other wheel, where rotation in a first direction causes tension on the first link line and not on the second link line, but rotation in a second direction, opposite the first direction, causes tension on the second link line and not on the first link line, and tension on the first link line causes movement in a positive X direction within the Y-Z plane, while tension on the second link line causes movement in a negative X direction within the Y-Z plane. In still a further detailed embodiment, the end effector comprises at least one of a surgical dissector, an ablation pen, an occlusion clip, an occlusion clip applicator, surgical forceps, surgical jaws, a linear cutter, an ablation clamp, and an ablation rail.

BRIEF DESCRIPTION OF THE DRAWINGS

FIG. 16 is a magnified profile view of a wheel and link plate, with the right side housing removed, showing the interaction between a wheel and a link plate at a third position.

FIG. 58 is an outside perspective view of an exemplary left side jaw of the exemplary laparoscopic device of FIG. 1.

FIG. 59 is an inside perspective view of the exemplary left side jaw of FIG. 58.

DETAILED DESCRIPTION

Figure 1:
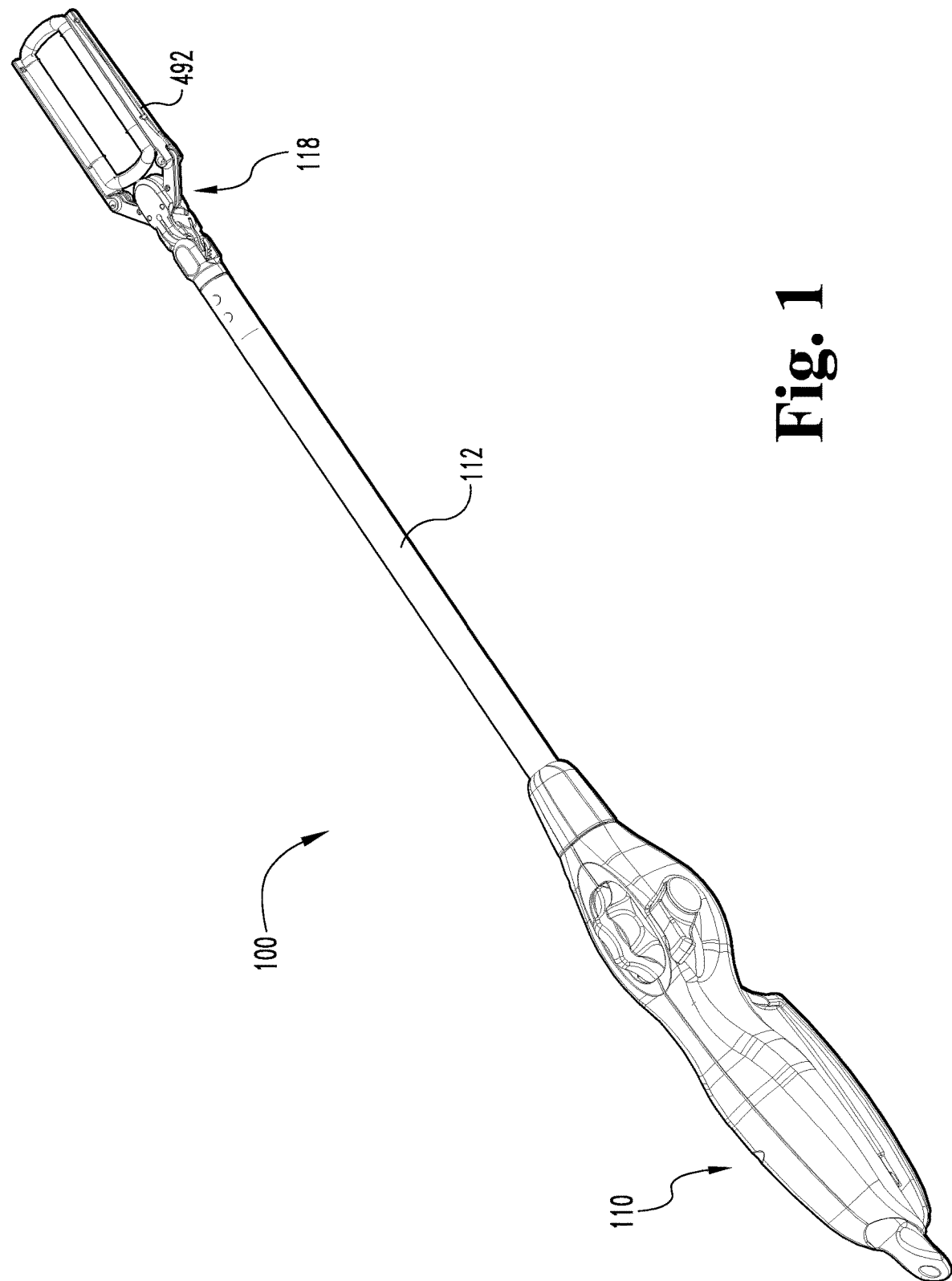
FIG. 1 is an elevated perspective view of an exemplary laparoscopic device in accordance with the instant disclosure.

The exemplary embodiments of the present disclosure are described and illustrated below to encompass surgical equipment and, more specifically, to surgical equipment that may be used in minimally invasive procedures. The disclosure also relates to surgical equipment to facilitate the positioning and deployment of an atrial appendage occlusion device. In addition, the disclosure relates to surgical equipment that is adapted to accommodate or work in tandem with flexible endoscopes. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-6, an exemplary laparoscopic device 100 comprises a controller 110 mounted to a proximal portion of a semi-rigid conduit 112 that is relatively linear. The controller 110 includes various controls in order to manipulate a repositionable mechanism 116 operatively coupled to an end effector 118, where the repositionable mechanism is mounted to a distal portion of the conduit 112. In this exemplary embodiment, the repositionable mechanism 116 is coupled to an end effector comprising a clip deployment device 118. But as will be discussed in later embodiments, the end effector 118 may comprise any number of devices such as, without limitation, forceps, ablation rails, jaws, linear cutters, ablation pens, ablation clamps, illuminated dissectors, and non-illuminated dissectors.

The exemplary repositionable mechanism 116 incorporates an active mechanism and a passive mechanism. It should be noted that the active mechanism is operative to control the pitch (i.e., up and down) of the end effector 118, while the passive mechanism is operative to control the yaw (i.e., side to side) of the end effector. However, as will be evident from the following disclosure, the repositionable mechanism 116 in an alternate exemplary embodiment may comprise only active or passive mechanisms. Conversely, the repositioning mechanism 116 in further alternate exemplary embodiments may utilize a passive mechanism to control the pitch (i.e., up and down) of the end effector 118, while an active mechanism is operative to control the yaw (i.e., side to side) of the end effector. Those skilled in the art will understand that the following description is one but of a plurality of configurations incorporating active and passive mechanisms to control the motion of an end effector 118 in two planes.

The controller 110 comprises a right side housing 130 and a left side housing 132 that cooperatively define an internal cavity and corresponding openings to accommodate throughput of certain controls. A first of these openings is a dorsal opening 134 that accommodates throughput of a pair of wheels 136, 138 that are rotationally repositionable along a lateral axis.

Referring to FIGS. 7-10, each wheel 136, 138 includes a contact face 140 adapted to be contacted by a user in order to rotate the wheel. The contact face 140 includes a series of circumferentially distributed depressions 142 interposed by a series of knurls 144 to facilitate grip between the user and the wheel 136, 138. Each knurl 144 is sloped to match the contour of the wheel 136, 138, which decreases from a maximum where the contact face 140 abuts an interior face 146. Radially inset from the depressions 142 and the knurls 144 is a planar ring surface 148 that circumferentially delineates the outer boundary of a ring-shaped exterior cavity 152. A pair of sloped surfaces 154, 156 inset from the ring surface 148 and axially spaced from one another operate to constrict the diameter of the cavity 152 when moving axially, deeper into the cavity. The cavity 152 is also partially delineated by a hollow axle 158 that extends from the center of each wheel 136, 138. This axle 158 is circumferentially surrounded at its base by a circular plateau 162, where the axle and plateau cooperate to incrementally increase the radial dimension of the ring-shaped cavity 152. An interior of the axle 158 defines a cylindrical cavity 166 that continues this cylindrical shape until reaching an interior midpoint where the cavity takes on a semicircular shape that extends through to the interior surface 146. A semicircular projection 170 adjacent to the cavity 166 extends generally perpendicularly away from the interior surface 146. The interior surface 146 also includes a spiral trench 172 that is distributed approximately two hundred and twenty degrees around the projection 170. In this manner, the radial distance between the trench 172 and the projection 170 gradually changes until reaching a maximum and minimum at the ends of the trench.

Figure 11:
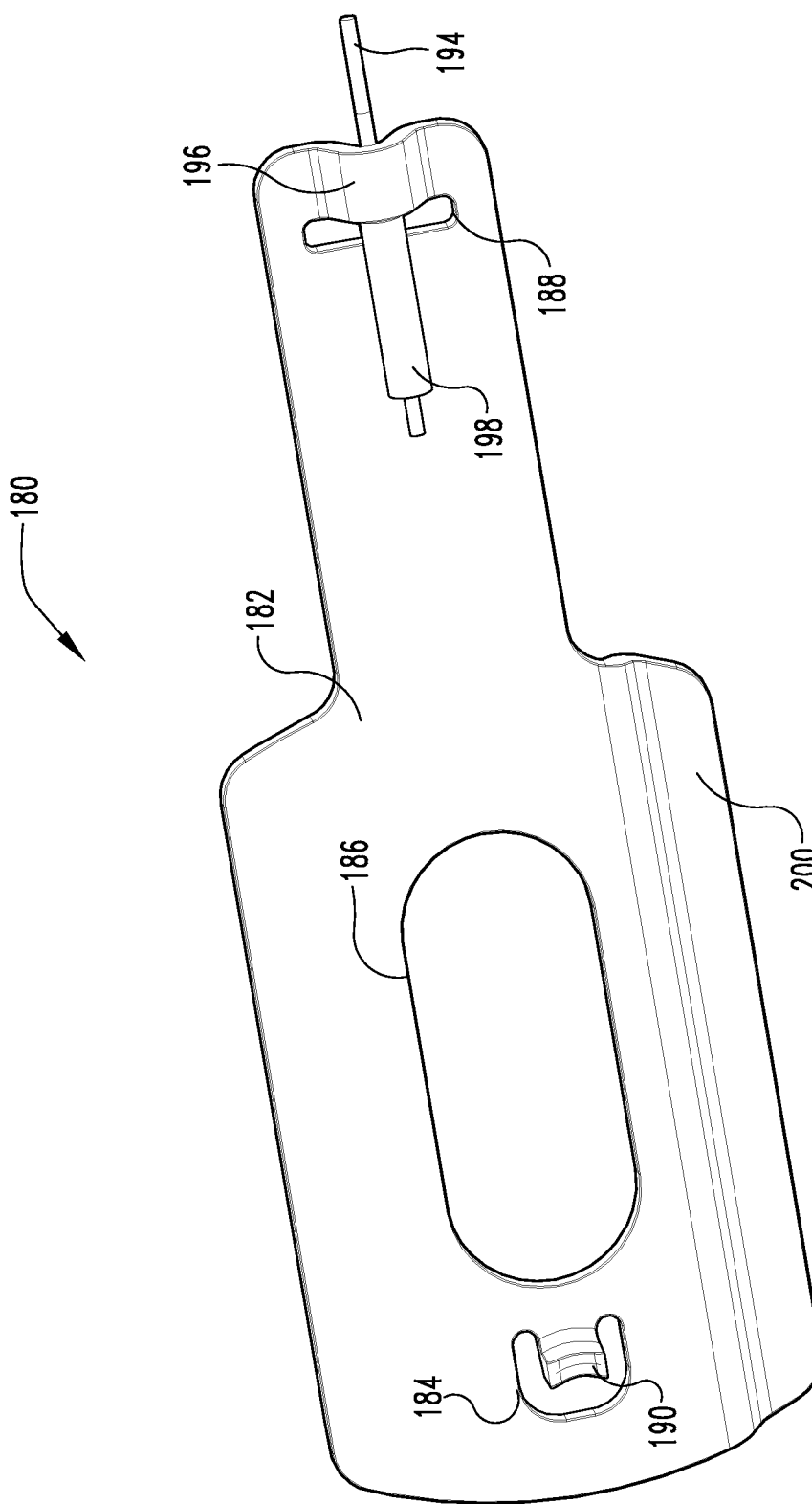
FIG. 11 is an elevated perspective view from the right side of an exemplary link plate of the exemplary laparoscopic device of FIG. 1.
Figure 12:
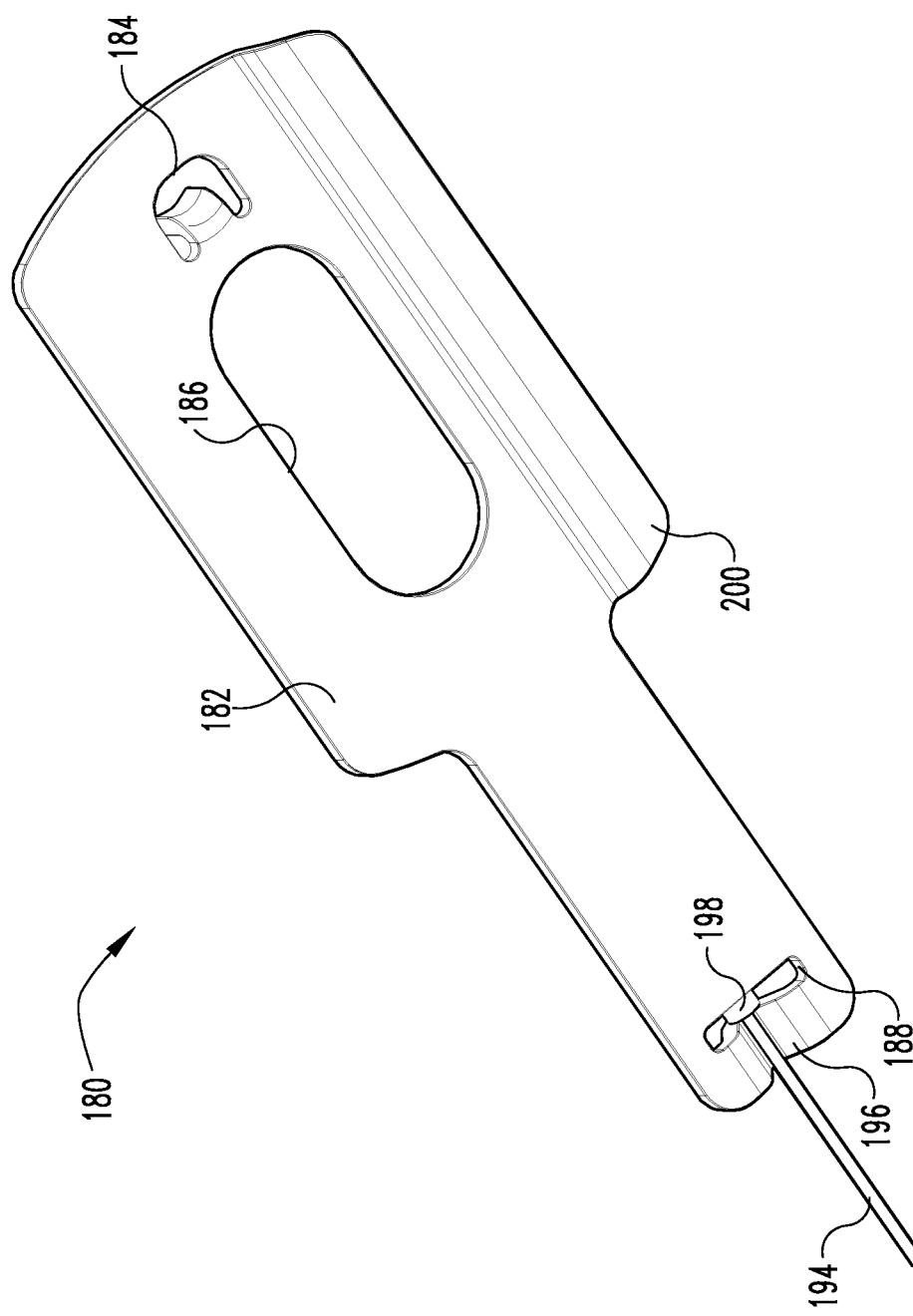
FIG. 12 is an elevated perspective view from the left side of the exemplary link plate of FIG. 11.
Figure 13:
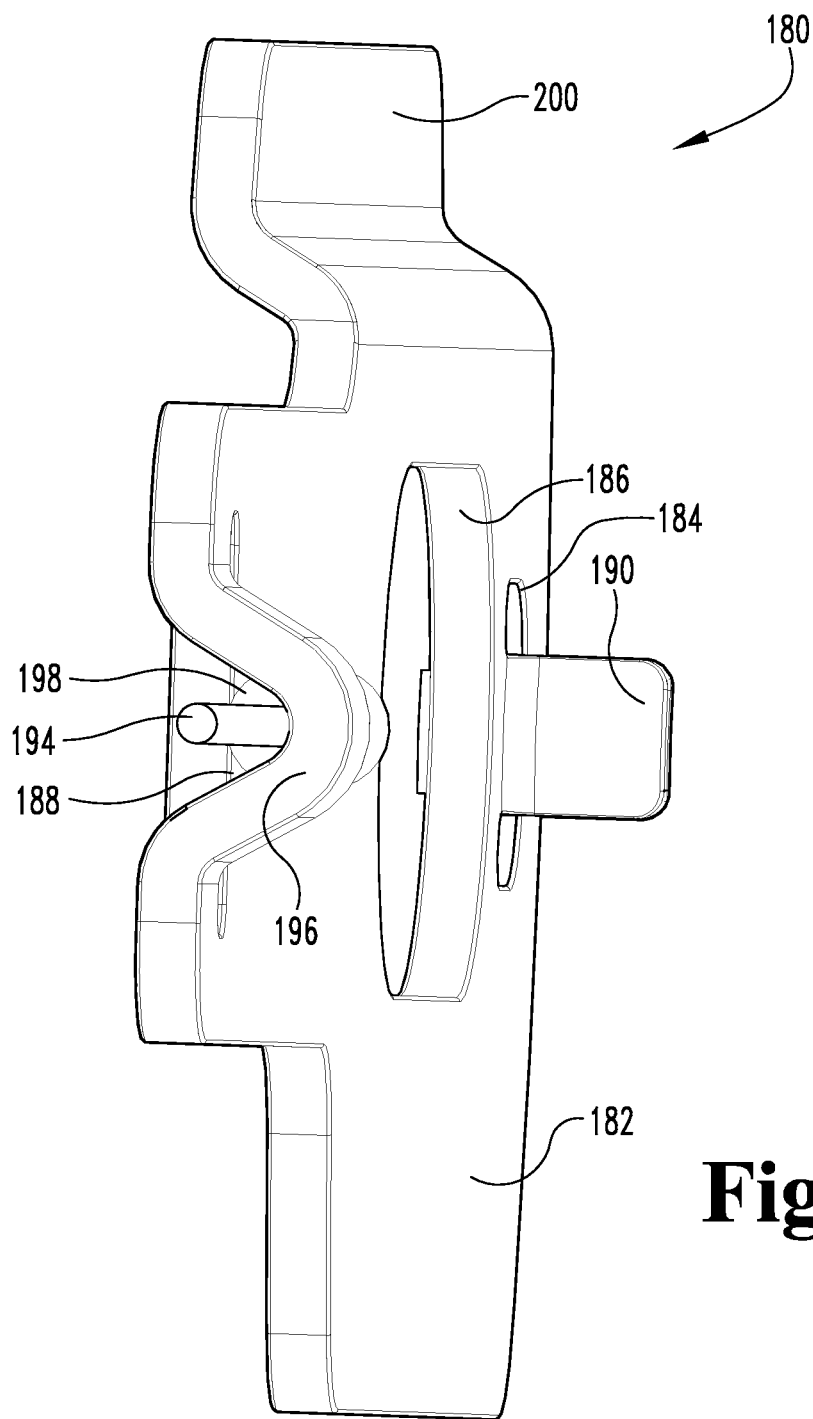
FIG. 13 is an elevated perspective view from the front of the exemplary link plate of FIG. 11.
Figure 14:
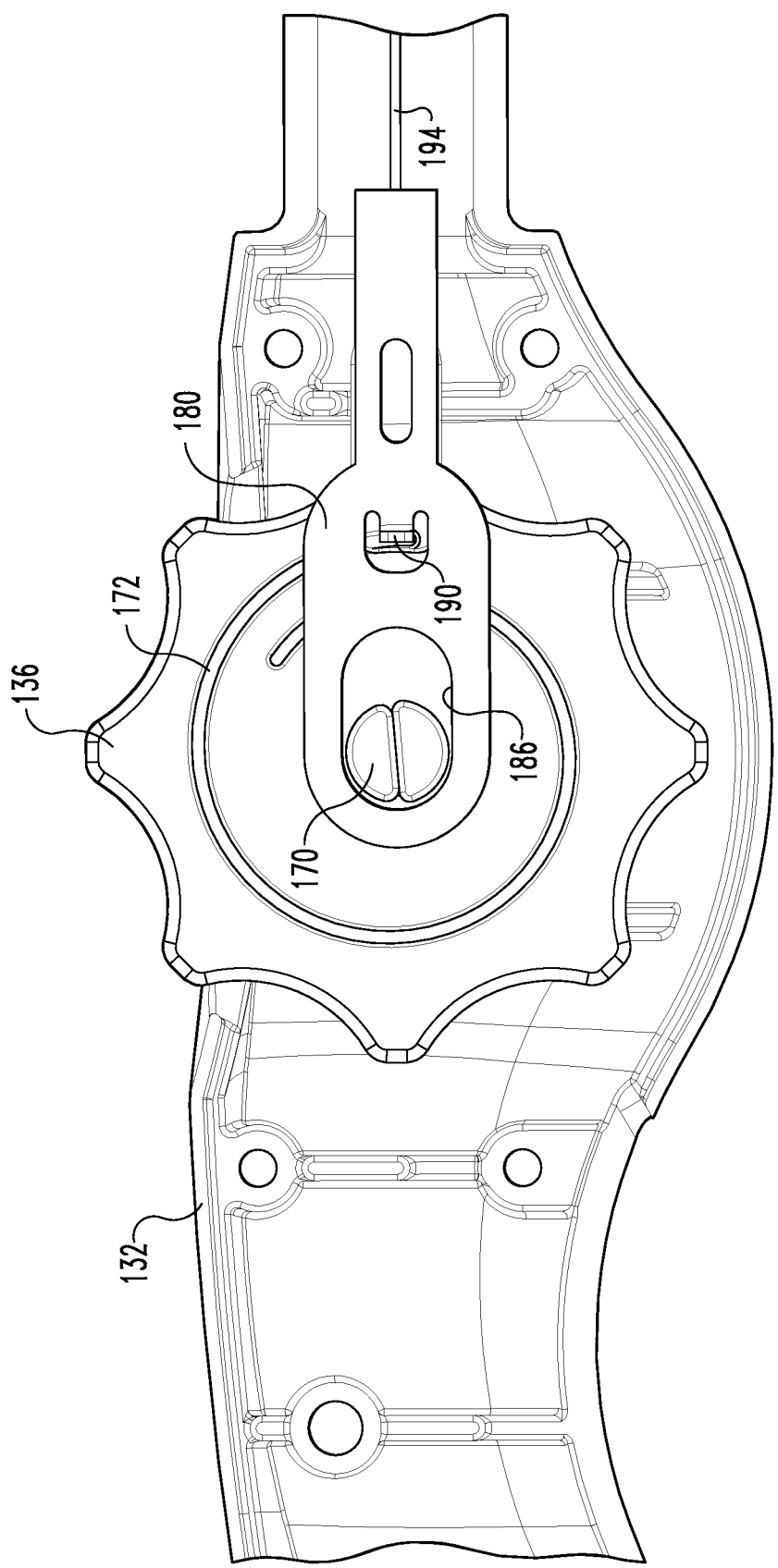
FIG. 14 is a magnified profile view, with the right side housing removed, showing the interaction between a wheel and a link plate at a first position.
Figure 15:
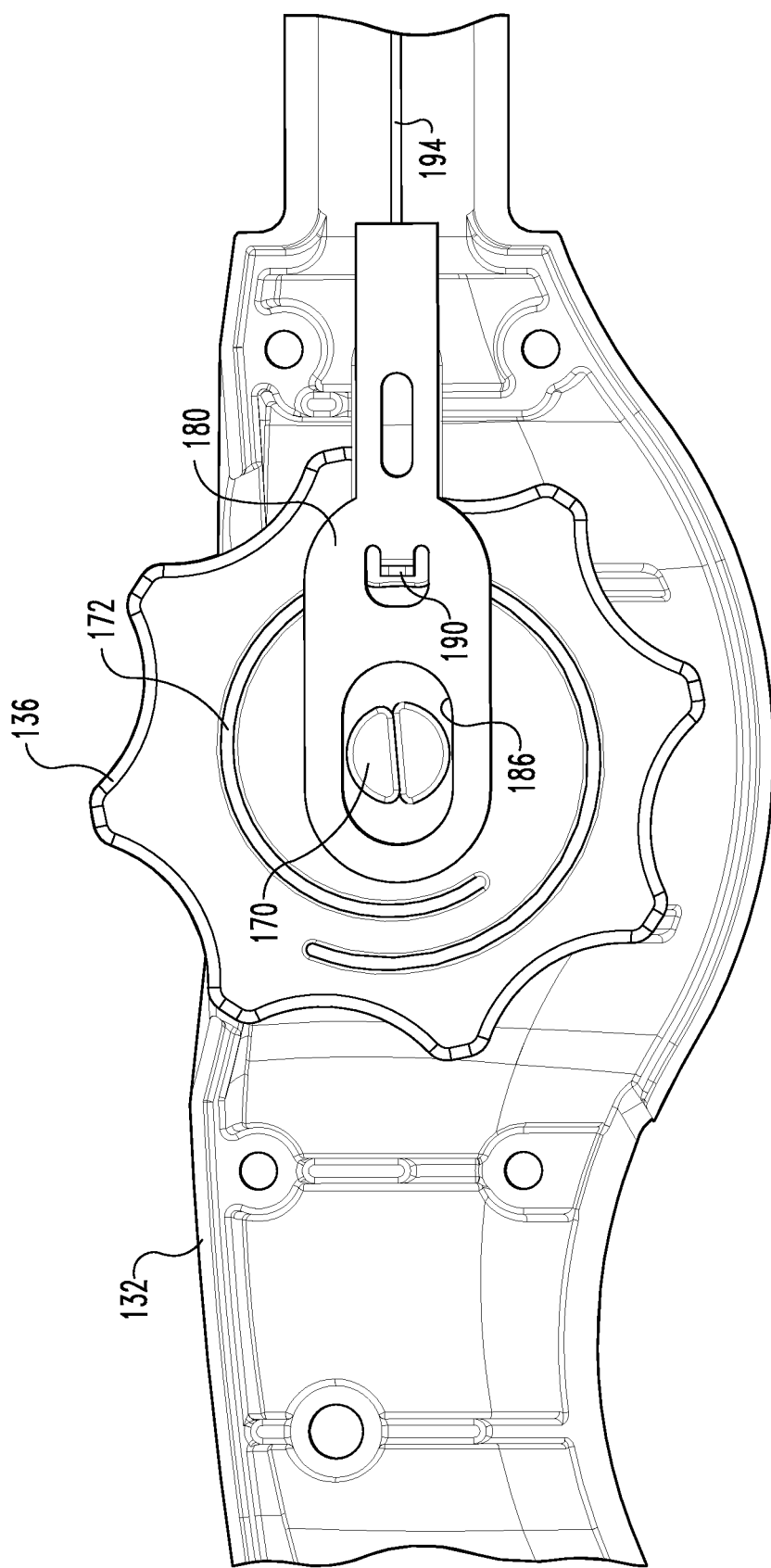
FIG. 15 is a magnified profile view, with the right side housing removed, showing the interaction between a wheel and a link plate at a second position.
Figure 17B:
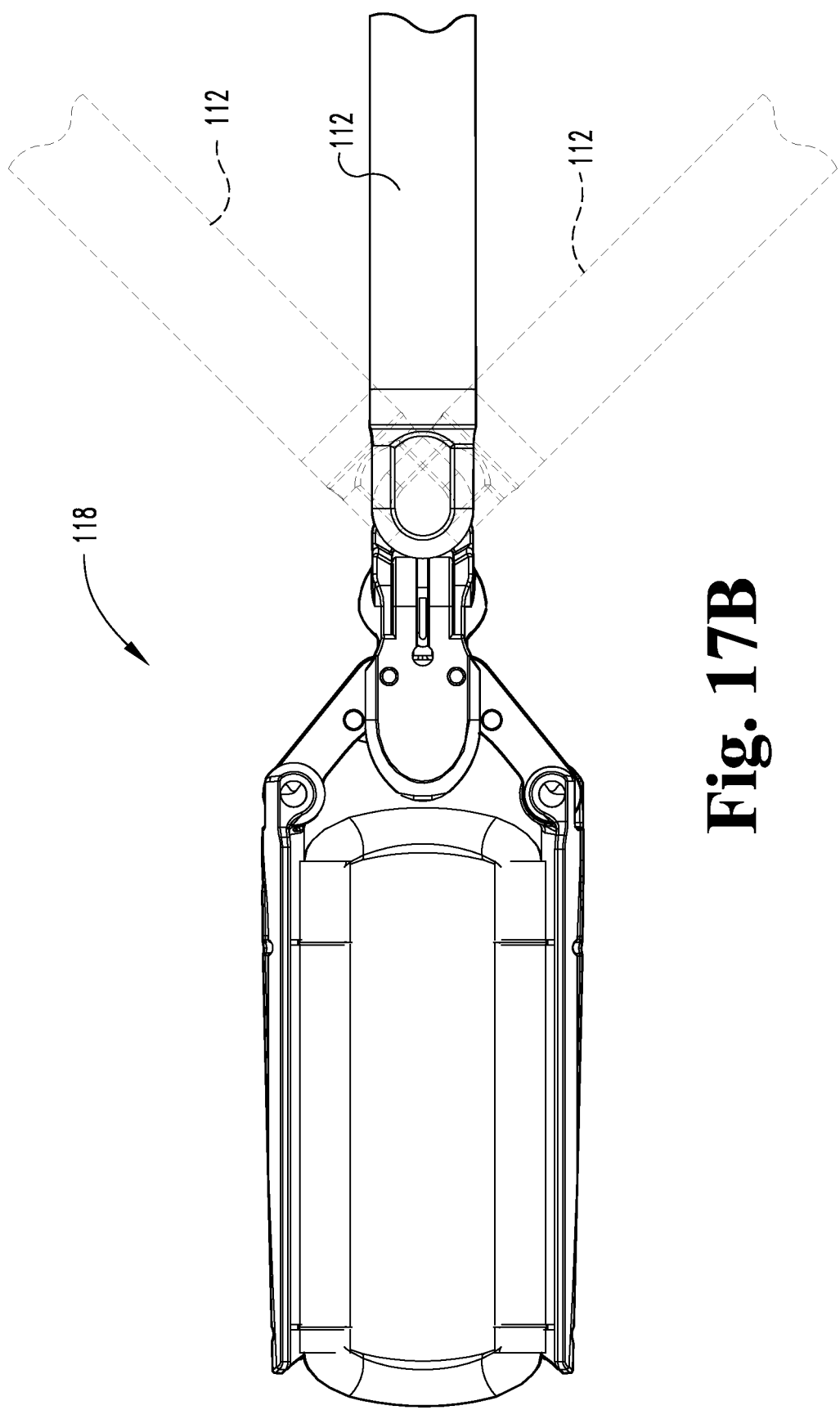
FIG. 17A is a profile view showing three vertical positions of the end effector achieved using an active repositioning mechanism.
FIG. 17 B is an overhead view showing three horizontal positions of the end effector (shown using changes in position of the semi-rigid conduit with respect to the end effector) achieved using a passive repositioning mechanism.

Referencing FIGS. 11-13, the wheels 136, 138 are operatively coupled to the repositionable mechanism 116 and operate to control pitch of the repositionable mechanism. In order to control pitch of the repositionable mechanism 116, each wheel 136, 138 is coupled to a link plate 180 that converts the rotational motion of the wheel into longitudinal motion along a longitudinal axis extending along the length of the conduit 112. In particular, each link plate 180 comprises a key shape having a planar section 182 and a plurality of stamped openings 184, 186, 188. The first of these stamped openings 184 has a horseshoe shape that creates a projection extending into the opening. This projection is thereafter deformed by bending the projection approximately ninety degrees to create a catch 190 that extends perpendicularly away from the planar section 182. The second opening 186 has a generally oval shape with circular ends and is provided in order to reduce the weight of the link plate 180 and provide a complementary opening for the semicircular projection 170 of a corresponding wheel 136, 138 (see FIGS. 8-10). The third opening 188 has a widthwise dimension that is substantially shorter than the vertical dimension to create an elongated, generally rectangular opening with rounded corners. This third opening 188 provides a throughput for a connection wire 194 and cooperates with a half-loop 196 to secure the connection wire to the link plate 180. In particular, the end of the planar section 182 is deformed to create the half-loop 196, where the connection wire 194 is threaded on the interior (i.e., concave aspect of the half-loop) of the half loop and extends through the third opening 188. In this exemplary embodiment, the connection wire 194 includes a cylindrical sleeve 198 that is secured to the wire so that lateral movement between the sleeve and wire does not occur. The sleeve 198 is dimensioned to allow for throughput of the sleeve and connection wire 194 through the third opening 188. In particular, after throughput of the sleeve 198 and connection wire 194 through the third opening 188, the sleeve 198 is positioned longitudinally against the link plate 180 and abuts the half loop 196. Specifically, the sleeve 198 is dimensioned so that the sleeve cannot pass through the half loop 196 when positioned longitudinally against the link plate 180. In this manner, repositioning of the connection wire 194 may be accomplished by repositioning the link plate 180 to place the connection wire 194 in tension. Each link plate 180 also includes a spacer flange 200 that extends above the second opening 186. The spacer flange 200 comprises a longitudinal S-shape bend that is applied to the top of the key-shape. This flange 200 cooperates with a counterpart flange 200 of another link plate 180 to ensure proper spacing between adjacent link plates.

Referring to FIGS. 2, 3, and 7-17, assembly of the wheels 136, 138 and link plates 180 provides for a means for repositioning the repositionable mechanism 116 upward or downward simply by rotating the wheels in a clockwise or counterclockwise direction. In particular, the link plates 180 are assembled back to back, with one of the link plates 180 being inverted, so that the flanges 200 face inward toward one another. In this manner, the flange 200 of a first link plate 180 abuts the planar surface 182, while the second link plate flange 200 abuts the planar surface 182 of the first link plate. In this orientation, the catches 190 of each link plate 180 extend outward, away from one another. More specifically, the catches 190 (and a portion of the link plates 180 themselves) are sandwiched between the interior faces 146 of the wheels 136, 138 and are received within a respective spiral trench 172 of the adjacent wheel 136, 138. At the same time, when the interior faces 146 are brought closer together, semicircular projections 170 of the wheels 136, 138 are aligned so that the planar surfaces of the projections abut one another, thereby forming a cylindrical projection that extends through both second openings 186 of the link plates 180.

Referring specifically to FIGS. 14-17A, rotation of the wheels 136, 138 in concert is operative to change the vertical orientation of the repositionable mechanism 116. For instance, starting at position A as shown in FIG. 17A, rotation of the wheels 136, 138 from the top, moving distally and downward, is operative to pull the first link plate 180 proximally, while pushing the second link plate distally. In other words, the rotational motion of the wheels 136, 138, via the interface between the spiral trench 172 and the catches 190, is transformed into horizontal motion of the link plates 180. More specifically, the catch 190 of the first link plate 180 abuts an end of the spiral trench 172 of the first wheel 136 that operates to limit the vertical travel of the repositionable mechanism 116. In this exemplary embodiment, the vertical travel is limited so that the maximum angle of deflection is negative sixty degrees from horizontal. In order to bring the repositionable mechanism 116 upward, the wheels 136, 138 are rotated clockwise, thereby changing the position of the spiral trench 172 with respect to the catch 190. In exemplary form, the catch 190 rides within the spiral trench 172 and is maintained in a constant horizontal orientation with respect to the trench because of the tension of the connection wire 194 pulling on the link plate 180 proximally. But as the wheels 136, 138 are rotated clockwise from position A, the distance from the center of the wheels to the spiral trench 172 occupied by the catch 190 decreases, thereby repositioning the first link plate 180 proximally with respect to the wheels. Continued rotation of the wheels 136, 138 clockwise (approximately ½ a turn) is operative to raise the repositionable mechanism 116 upward to reach position B (see FIG. 17A), where the repositionable mechanism is angled zero degrees from horizontal. Further clockwise rotation of the wheels 136, 138 clockwise (approximately ½ a turn) is operative to raise the repositionable mechanism 116 upward to reach position C (see FIG. 17A), where the repositionable mechanism is angled sixty degrees from horizontal. Conversely, rotation of the wheels 136, 138 from the top, moving proximally and downward, is operative to push the first link plate 180 distally, while pulling the second link plate proximately, thereby lowering the repositionable mechanism 116 by way of the connection wires 194.

The rotation of the wheels 136, 138 is proportional to the pivoting motion of the repositionable mechanism 116. It should be noted that position C corresponds to the catch 190 being adjacent the opposite end of the spiral trench 172, which is operative to set the vertical travel limit of sixty degrees from horizontal. Simply put, by rotating the wheels 136, 138 approximately 360 degrees, the repositionable mechanism is operative to travel 120 degrees. Accordingly, the wheels 136, 138 are operative to convert three degrees of rotational motion into one degree of pivoting motion. And the shape of the spiral trench 172 may be modified to increase or decrease the conversion between rotational motion of the wheels 136, 138 to pivoting motion of the repositionable mechanism 116. For example, the pitch of the spiral trench 172 may set so that two full rotations of the wheels 136, 138 are necessary to move from one endpoint to the opposite endpoint of the trench. In such an example, the conversion would be six degrees of rotational motion translating into one degree of pivoting motion (presuming the maximum pivoting range was 120 degrees). In other words, it would take two full rotations of the wheels 136, 138 to move between the pivotal endpoints of the repositioning mechanism 116. In contrast, the pitch of the spiral may be set to extend around one third of the wheels 136, 138 so that the conversion would be one to one (i.e., one degree of rotational motion translates into one degree of pivoting motion).

The spiral trench 172 can also be set to have variable rates as the wheels 136, 138 are turned. In other words, the distance changes from the center of the wheels 136, 138 to the trench 172 is not constant along all 360 degrees. For example, the middle section of the trench 172 may have a pitch that correlates to two degrees of rotation being converted into one degree of pivotal motion of the repositionable mechanism 116 within ±20 degrees from horizontal (i.e., zero degrees). But beyond this point, the trench 172 pitch is decreased so that the final 40 degrees of travel (between 20 to 60 degrees and −60 to −20 degrees) is achieved by turning the wheels three degrees to achieve one degree of pivotal motion. Those skilled in the art will understand that various combinations can be achieved by changing the pitch of the trench 172 and having one or more trench sections with different pitches.

Figure 18:
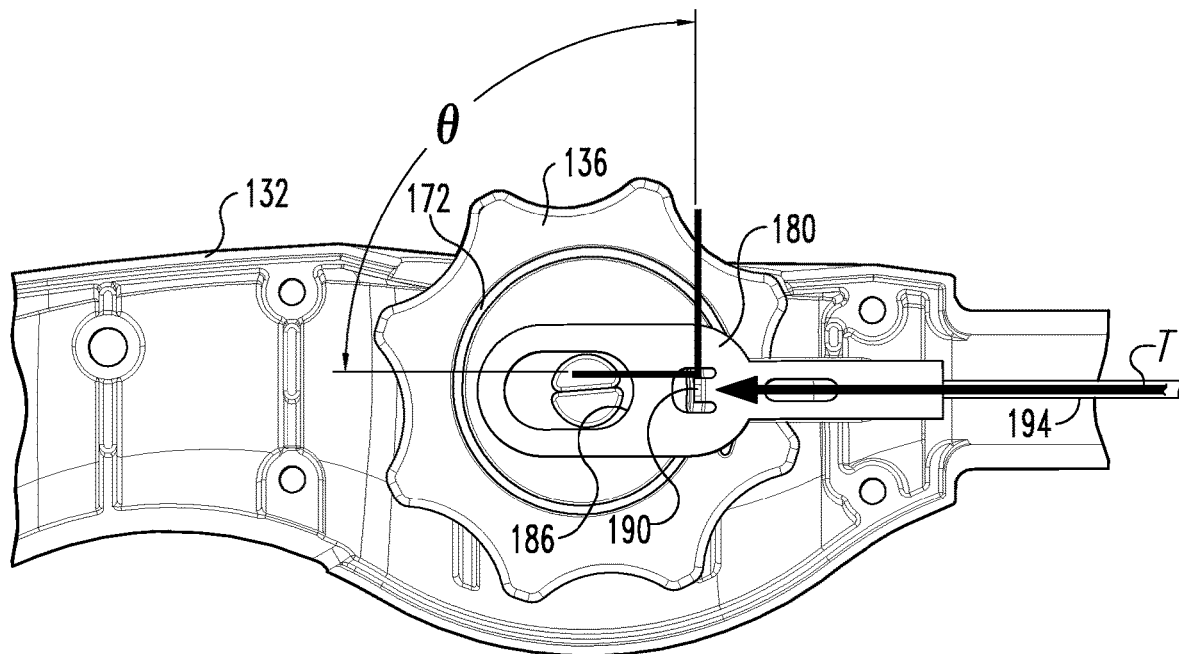
FIG. 18 is a magnified profile view, with the right side housing removed, showing an angle θ between the catch and the trench.

Referring to FIG. 18, the pitch (i.e., angle θ) of the spiral trench 172 also influences whether the repositioning mechanism 116 is self-locking. In the context of this disclosure, self-locking refers automatically inhibiting movement. In exemplary form, as the angle θ of the spiral trench 172 increases (and the conversion from rotation degrees to pivoting degrees decreases), the resistance to movement of the catch 190 within the trench 172 decreases. In exemplary form, when the angle θ between the catch and trench is ninety degrees, resistance is maximized. In contrast, when the angle θ between the catch and trench is zero, the resistance is minimized. At some angle θ between zero and ninety, the resistance is great enough to provide a self-locking feature. In other words, to achieve a self-locking feature, the resistance to movement of the catch 190 within the trench 172 must be greater than the tensile force T on the connection wire 194. The more spiral turns that comprise the trench 172, the greater the angle θ. The less spiral turns that comprise the trench 172, the lesser the angle θ and the greater the chance of a back load causing the wheels 136, 138 to rotate. In exemplary from, the spiral trench 172 has an angle of approximately 80-85 degrees. This angle is sufficient to provide a self-locking feature so that a back load (a force applied directly to the repositioning mechanism 116 that is transmitted along the connection wire 194) is inoperative to cause the wheels 136, 138 to rotate, thereby inhibiting pivoting motion of the repositioning mechanism. However, it may be desirable to avoid a self-locking feature, at which point the shape of the catch 190 and trench 172 can be changed to decrease the friction therebetween, including decreasing the spiral turns to decrease the angle θ.

As discussed above, the wheels 136, 138 are rotated and act as cams to reposition the link plates 180, which in turn repositions the connection wires 194. As will be discussed in more detail hereafter, the connection wires 194 are mounted to the yoke 614 that rotates with respect to the pelvis halves 594, 596 in order to provide an infinite number of positions within the range of motion afforded by the spiral trench 172 of the wheels 136, 138. For purposes of this disclosure, this mechanism is referred to as an active repositioning mechanism because it is the affirmative rotation of the wheels that directly results in a proportional movement of the yoke 614 with respect to the pelvis halves 594, 596. Moreover, a user of the wheels 136, 138 is operative to lock the position of the end effector 118 simply by discontinuing rotation of the wheels. In exemplary form, the resistance to rotation of the wheels 136, 138 is the result of the angle between the trench 172 boundaries and the catch 190 of the link plates 180. Based upon the structure of this mechanism, a user of the wheels 136, 138 actively controls the position of the end effector 118.

In an alternate exemplary embodiment, the active mechanism may be remotely controlled so that a user does not physically touch the wheels 136, 138, but instead operates a controller remote from the wheels. The controller is in communicatively coupled to a motor or actuator operative to drive the wheels in the desired direction, thereby allowing remote control of the wheels.

In a further alternate exemplary embodiment, the active mechanism is removed from the controller 110 and repositioned distally at the distal end of the conduit 112, proximate the end effector 118. In such an embodiment, the active mechanism is exposed and available to be manipulated by a robotic appendage, thereby repositioning the end effector locally (with respect to the controller 110). More specifically, the wheels would be rotated by the robotic appendage in order to reposition the end effector 118.

As will be discussed in more detail hereafter, this active mechanism is in contrast to a passive mechanism having "on" and "off" functionality that allows certain movement of the end effector 118 or disallows this same movement. Because the mechanism does not affirmatively allow control of incremental motion of the end effector 118, but rather only operates to allow or disallow motion, the mechanism is referred to herein as passive.

Referring back to FIGS. 1, 5, and 19-23, the right side housing 130 of the controller 110 also includes an exterior depression 230 and a pair of through openings 232, 234 to accommodate a repositionable lever 236 that is part of the passive mechanism. As will be discussed in more detail hereafter, the repositionable lever 236 may be manipulated to lock and unlock the repositionable mechanism 116 in order to provide for or constrain lateral adjustability of the end effector 118. The first through opening 232 is defined by a cylindrical bearing 238 that extends perpendicularly away from the housing 130. The bearing 238 includes an exterior circular bearing surface 240 and an interior circular bearing surface 242 that are sandwiched by the lever 236. In this manner, the lever 236 rotates around the exterior bearing surface 240 and rotates within the interior bearing surface 242. The lever 236 includes a tapered appendage 248 integrally formed with a cupped cover 250. An interior of the cupped cover 250 is hollowed to define an internal cavity 252 delineated by a peripheral wall 254 having a generally circular shape at one end and an arcuate shape (but not rounded) at the other end. A cylindrical upstanding projection 256 extends perpendicularly away from the interior of the cupped cover 250 and is generally equidistantly spaced from the circular portion of the peripheral wall 254, but extends above the height of the peripheral wall. A second cylindrical upstanding projection 258 is formed at a corner of the arcuate end of the peripheral wall 254. This second cylindrical projection 258 extends perpendicularly away from the interior of the cupped cover 250 (and parallel to the first cylindrical projection 256) and extends above the height of the first cylindrical projection 256. The first cylindrical projection 256 is received within the first through opening 232 of the cylindrical bearing 238, while the second cylindrical projection 258 is received within the second through opening 234. The circular cross-section of the first cylindrical projection 256 and the first through opening 232 and the dimensions of each allow for rotation of the rotation of the first cylindrical projection within the first through opening without significant radial play that would otherwise cause the lever 236 to not consistently rotate around a single rotational axis. Conversely, the second through opening 234 is elongated and takes on an arcuate path that tracks the movement of the second cylindrical projection 258. More specifically, the second through opening 234 includes rounded ends that generally match the curvature and dimensions of second projection 258, but allow for play between the bounds of the opening and the projection so the projection can move within the opening. At the same time, the height of the second through opening 234 is slightly larger than the diameter of the second projection 258, while the arcuate path of the through opening tracks the position of the second projection as the lever 236 rotates about the housing 130. The bounds or endpoints of the opening 234 provide a limit on the rotational repositioning of the lever 236. As will be discussed in more detail hereafter, the bounds provide a locked and an unlocked position that corresponds to locked or free lateral adjustability of the end effector 118. More specifically, the lever 236 is coupled to a connection wire 261 by winding the connection wire around the first cylindrical projection 256. The remaining exterior surface 260 of the right side housing 130 is convex and includes a number of additional features.

Figure 2:
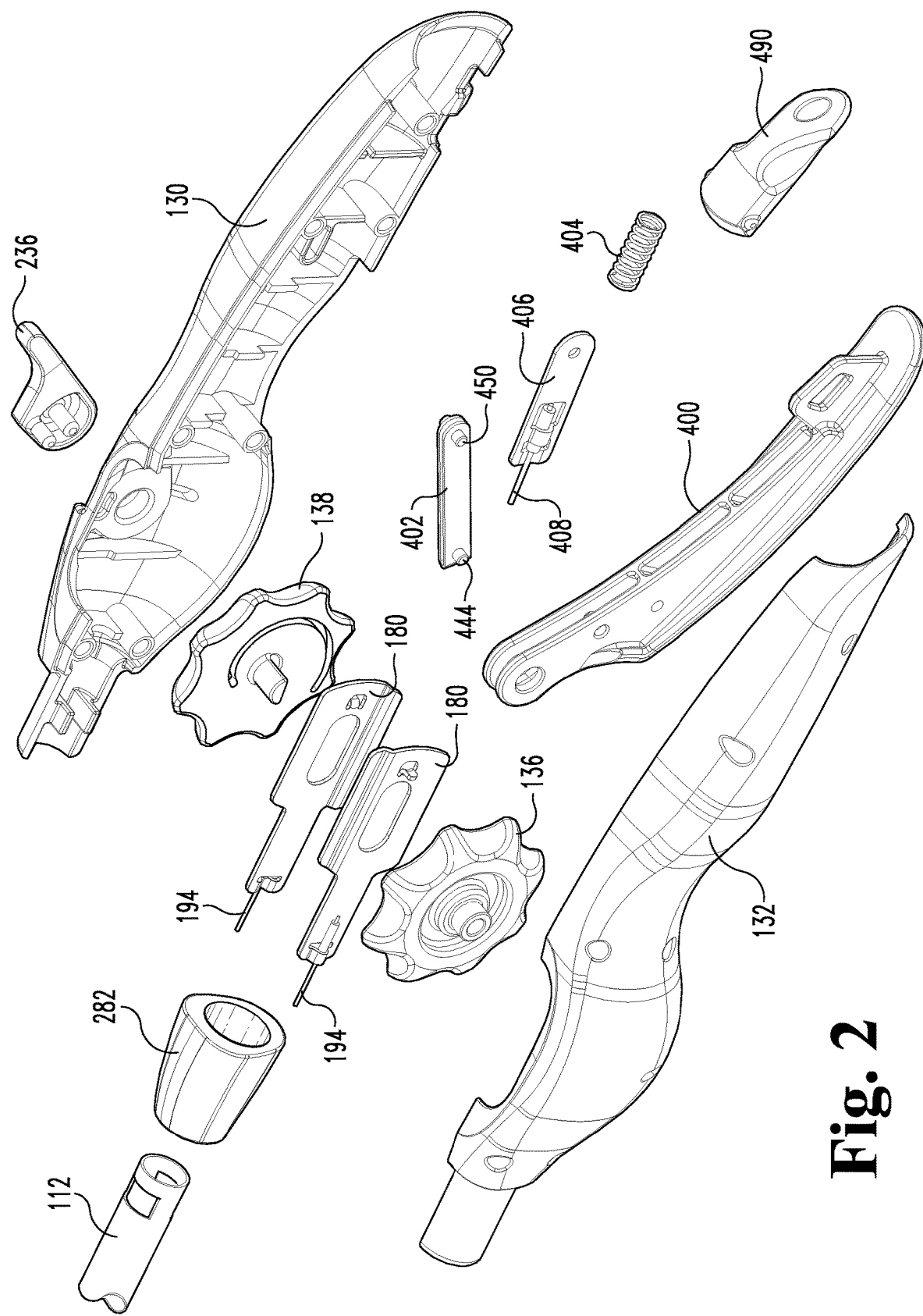
FIG. 2 is an exploded view of a proximal end of the exemplary laparoscopic device of FIG. 1.
Figure 19:
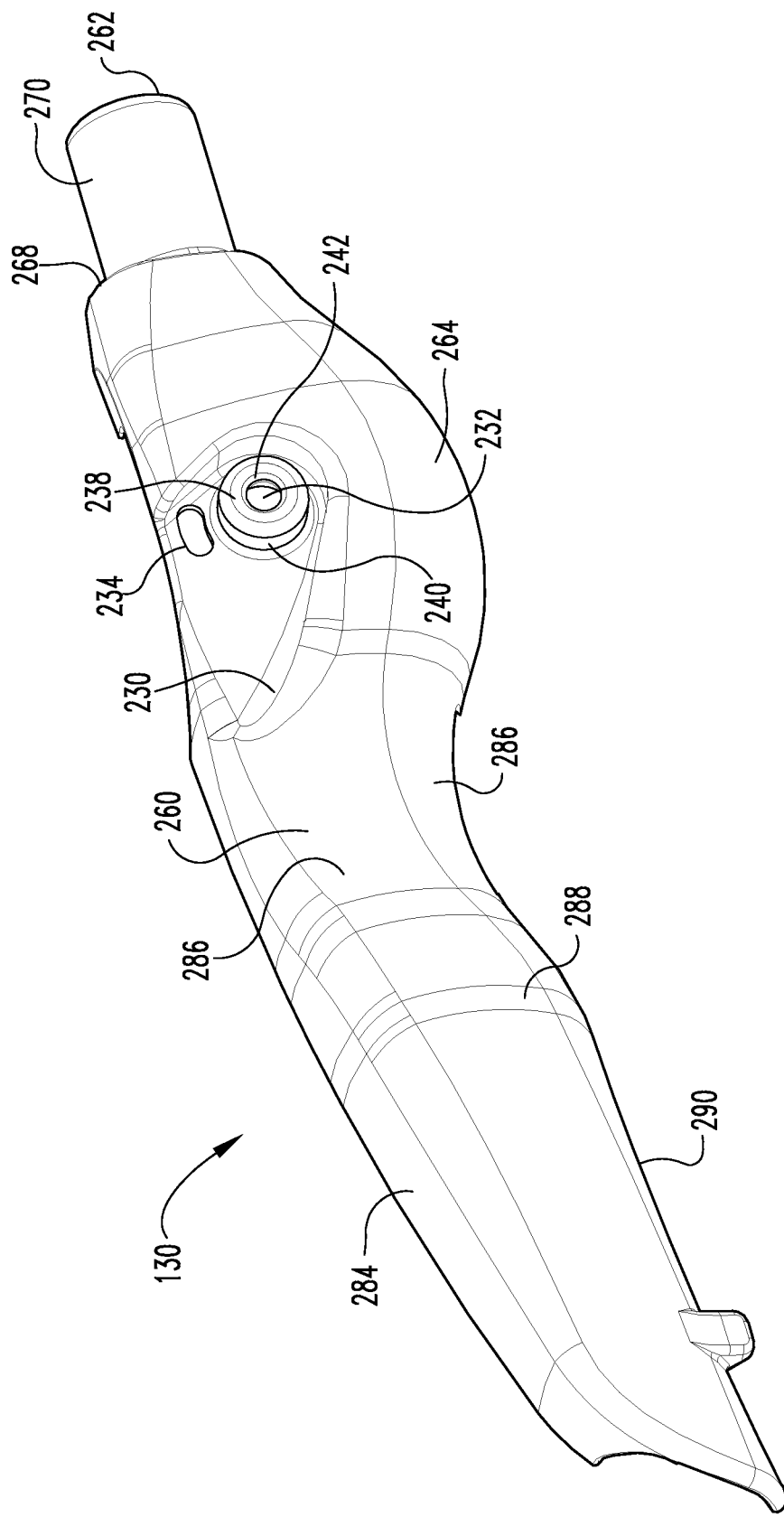
FIG. 19 is an elevated perspective view of the outside of the right side housing of the exemplary laparoscopic device of FIG. 1.
Figure 20:
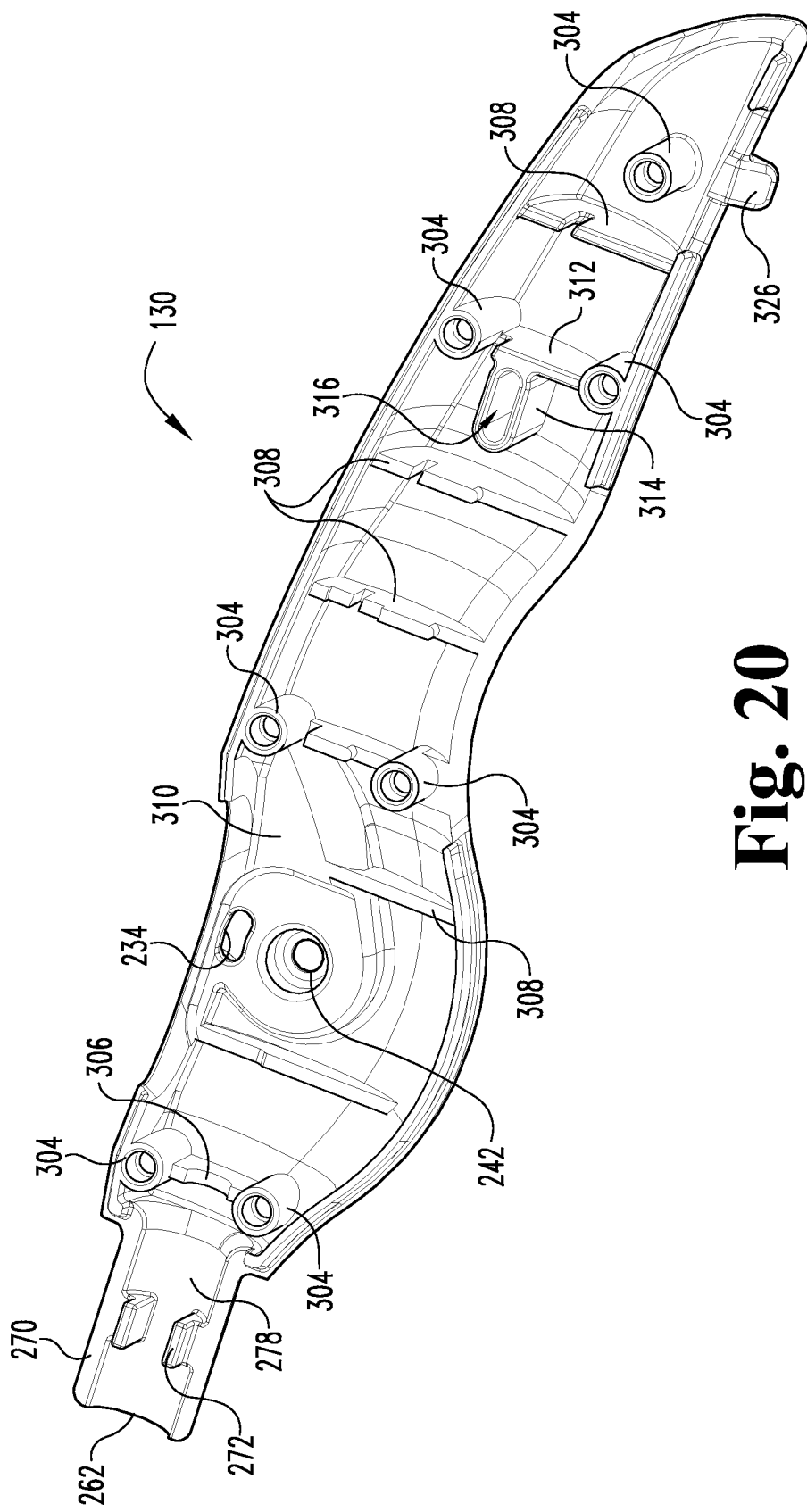
FIG. 20 is an elevated perspective view of the inside of the right side housing of the exemplary laparoscopic device of FIG. 1.
Figure 21:
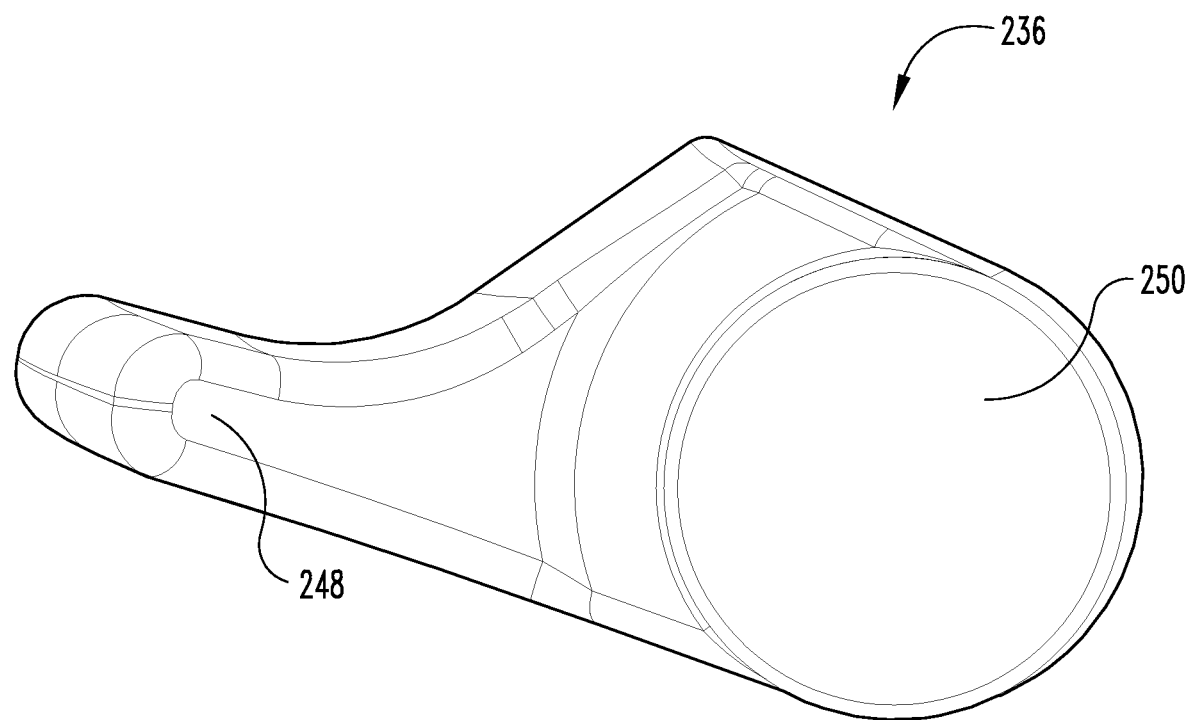
FIG. 21 is an elevated perspective view of the outside of an exemplary lever of the exemplary laparoscopic device of FIG. 1.
Figure 22:
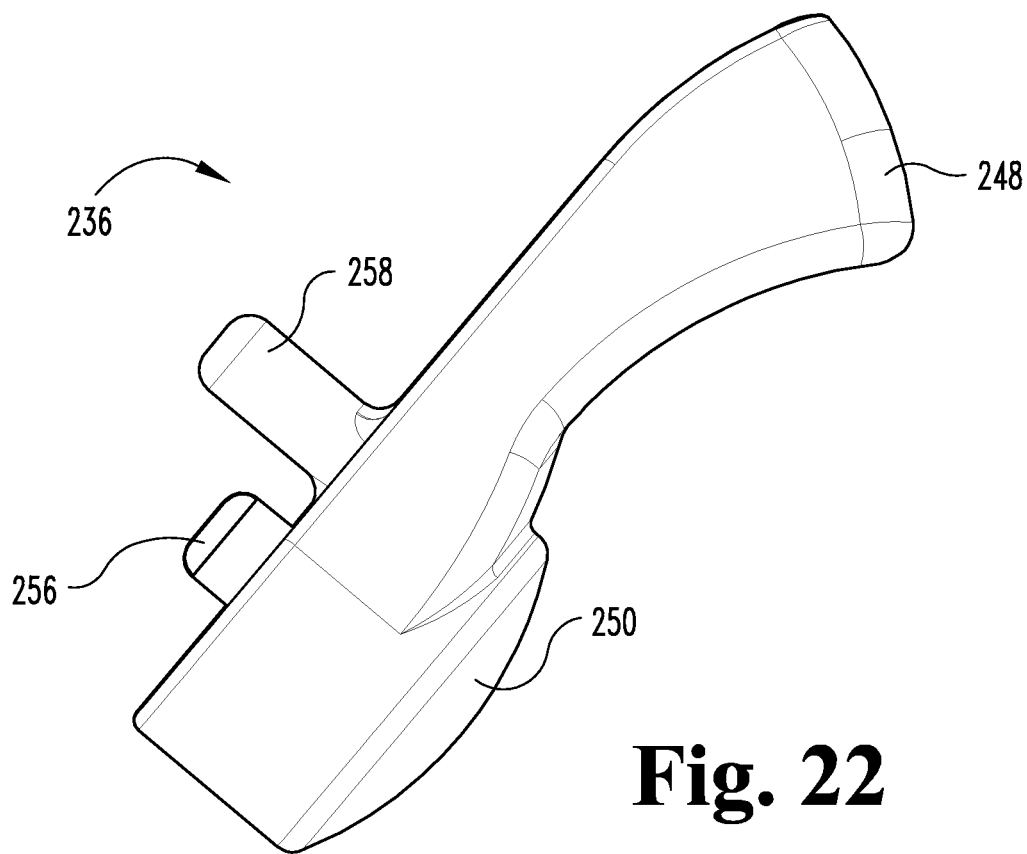
FIG. 22 is a profile view of the exemplary lever of FIG. 21.
Figure 23:
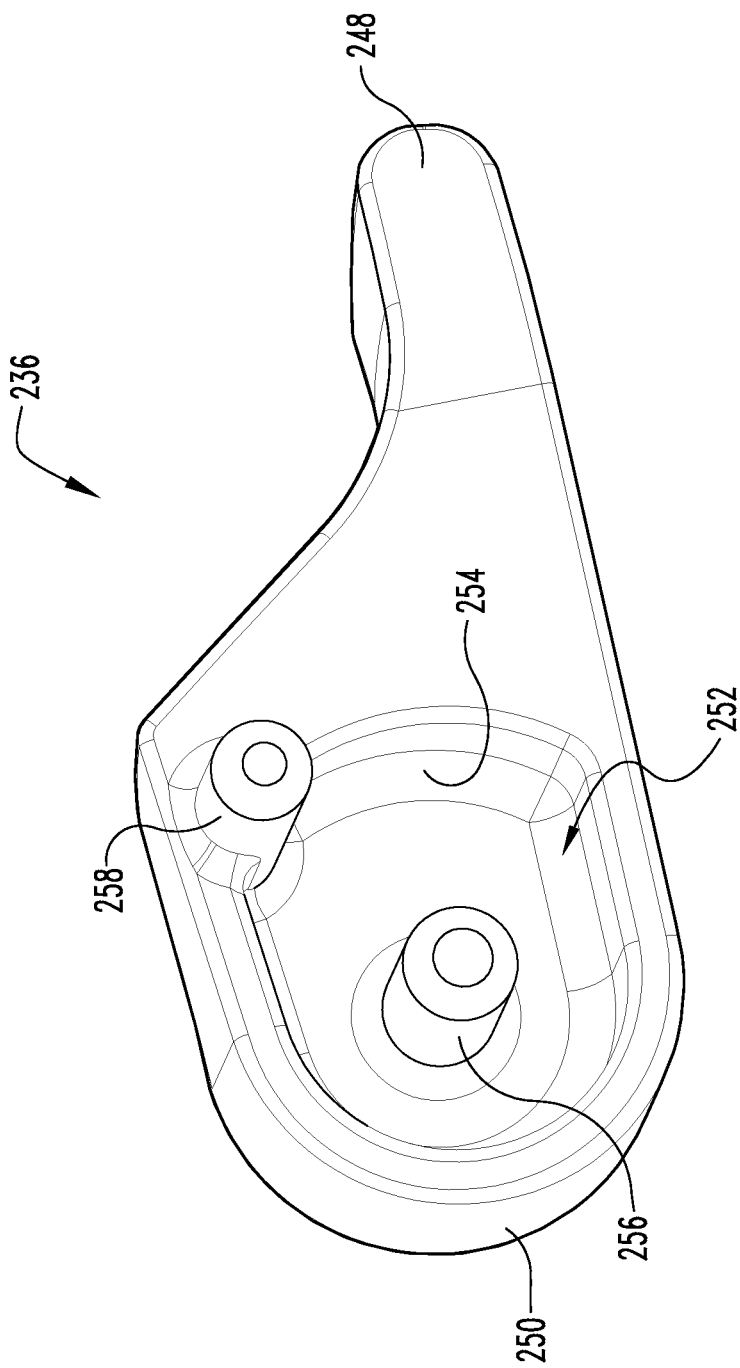
FIG. 23 is an elevated perspective view of the inside of the exemplary lever of FIG. 21.
Figure 24:
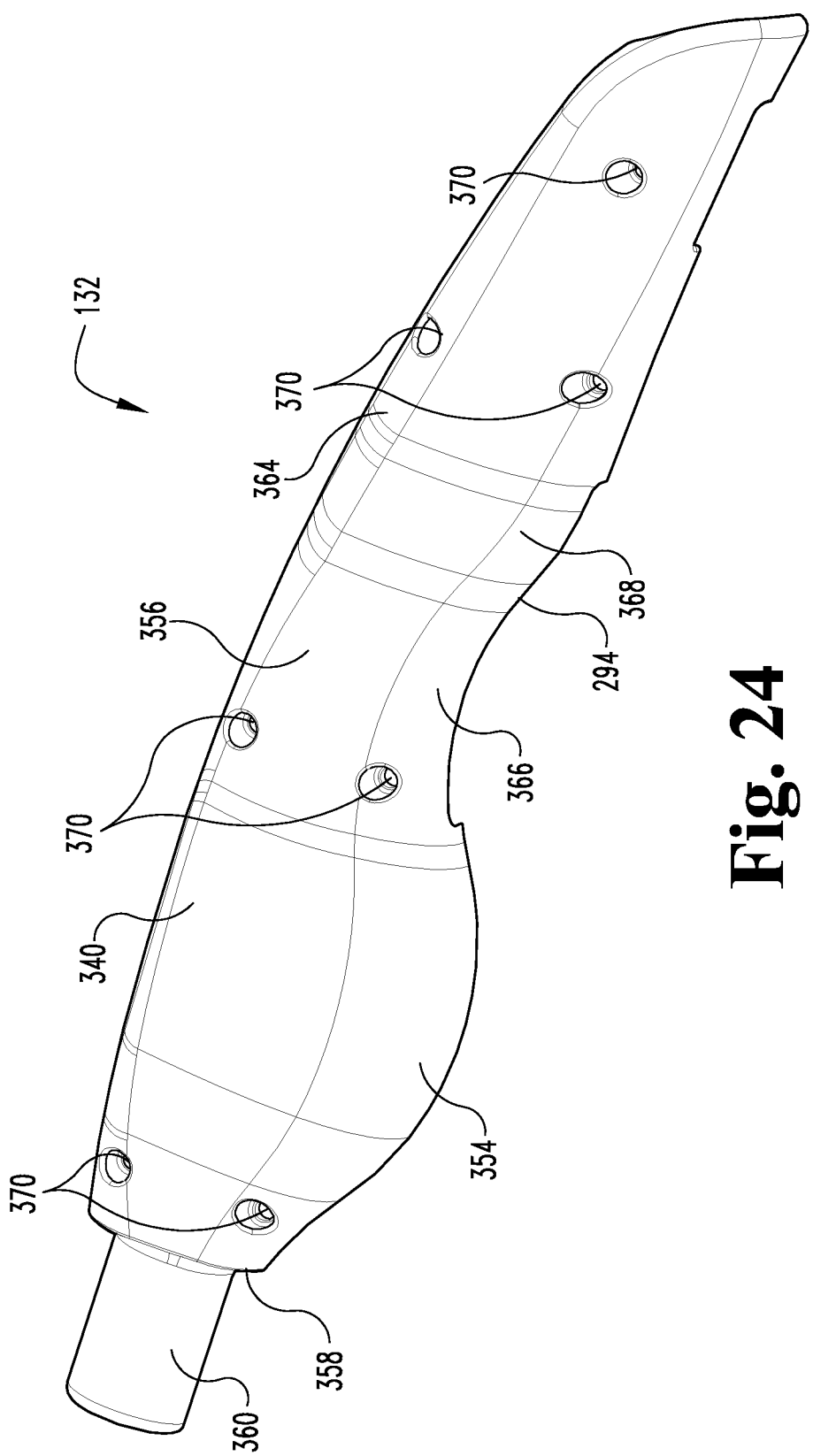
FIG. 24 is an elevated perspective view of the outside of the left side housing of the exemplary laparoscopic device of FIG. 1.

Referring specifically to FIGS. 2, 19, and 20, the additional features include an enlarged section 264, proximate a distal end 262, which is rounded on its underside. This enlarged section 264 tapers proximally and distally to transition into a proximal neck 266 and a distal flange 268. The distal flange 268 interposes the enlarged section 264 and a semi-circular adapter 270. As will be discussed in more detail hereafter, the adapter 270 includes a pair of detents 272 that engage the semi-rigid conduit 112 in order to inhibit longitudinal movement of the conduit with respect to the controller 110. Both detents 272 extend in parallel to one another and extend from an interior circumferential surface 278 of the adapter 270 that communicates with an exterior of the semi-rigid conduit 112. The exterior of the adapter 270 is smooth and semicircular in order to receive a cylindrical cap 282 that circumscribes the exterior of the adapter 270.

Figure 5:
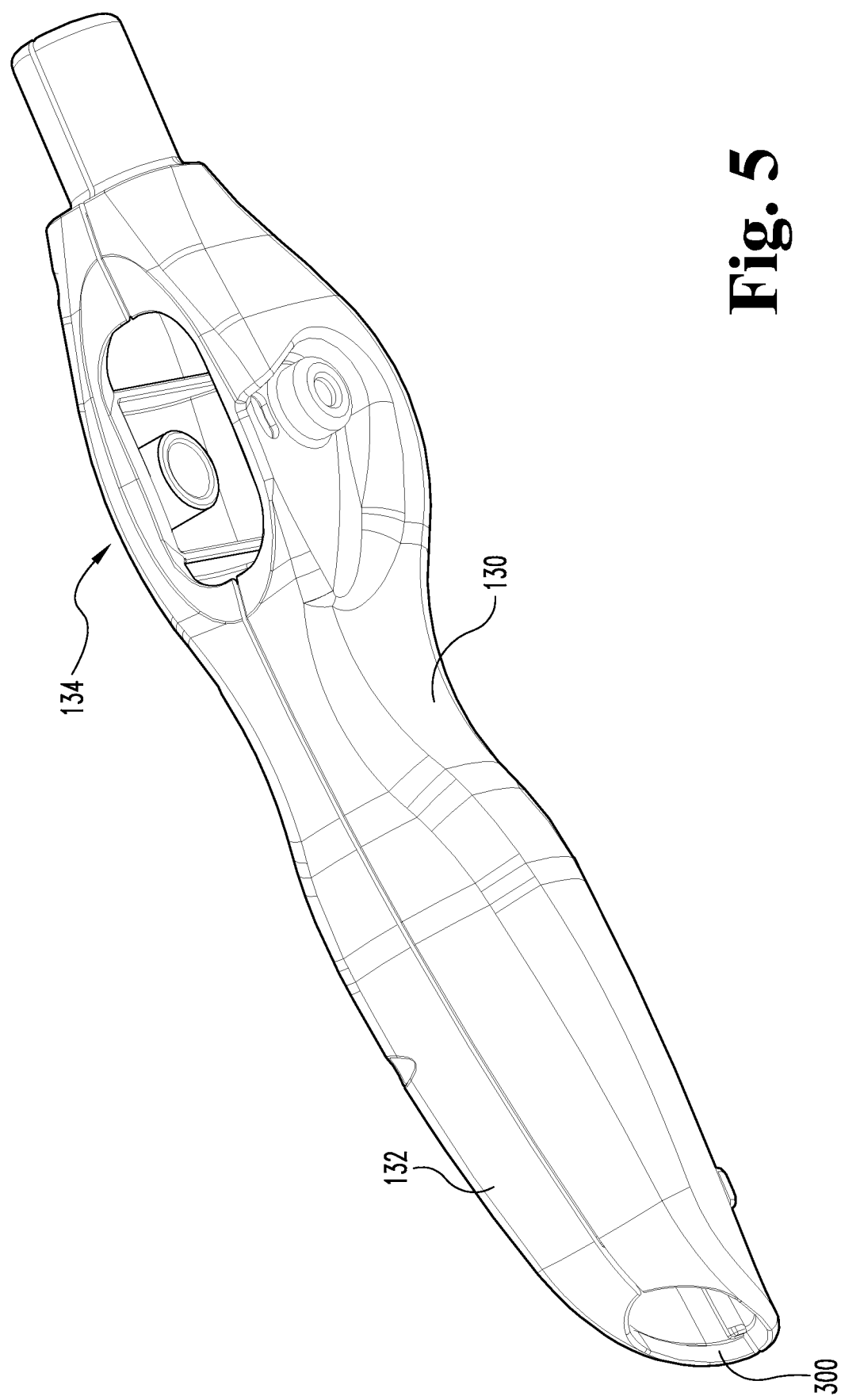
FIG. 5 is an elevated perspective view of the right and left side housings mounted to one another.
Figure 6:
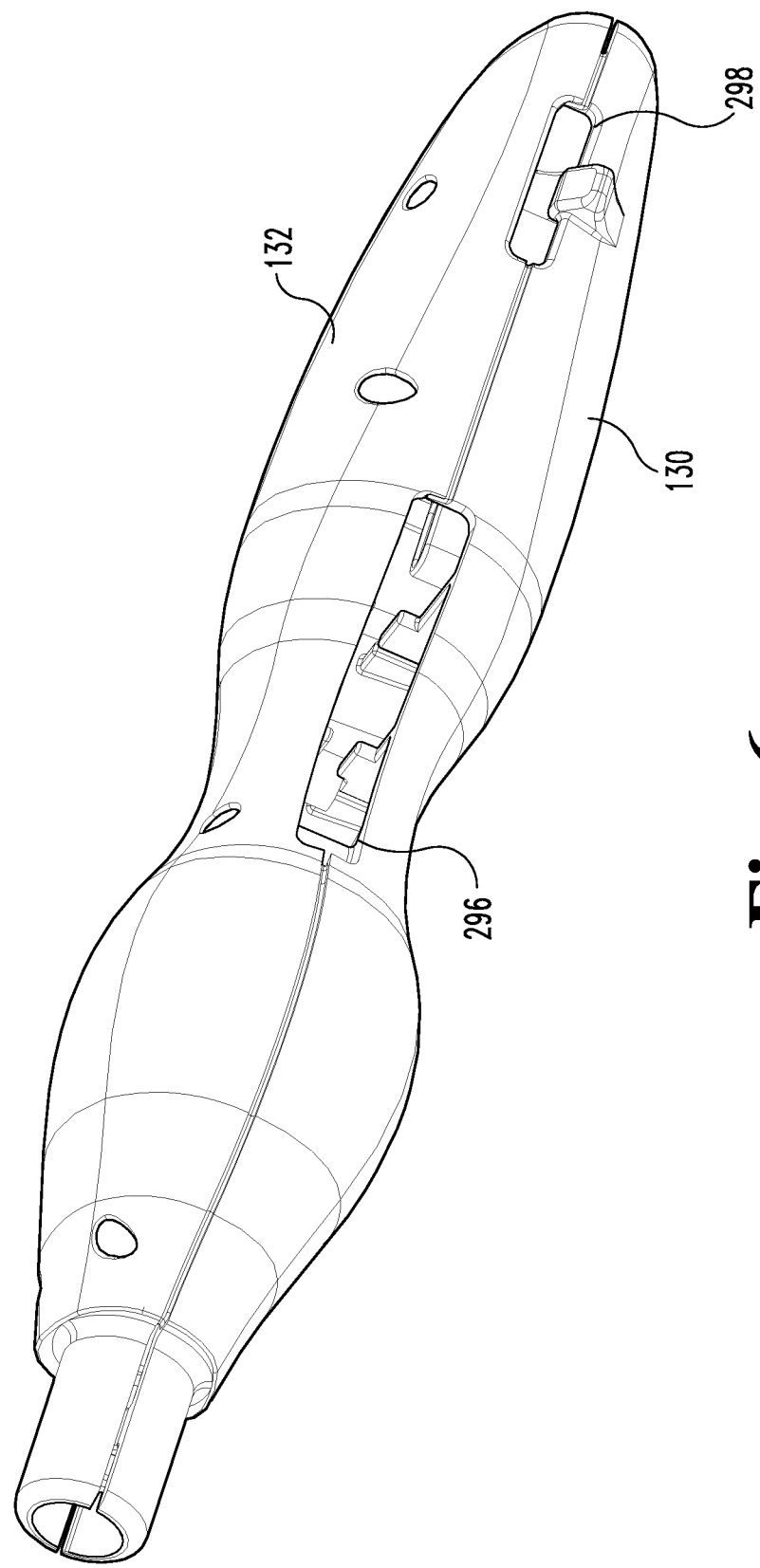
FIG. 6 is an underneath perspective view of the right and left side housings mounted to one another.
Figure 7:
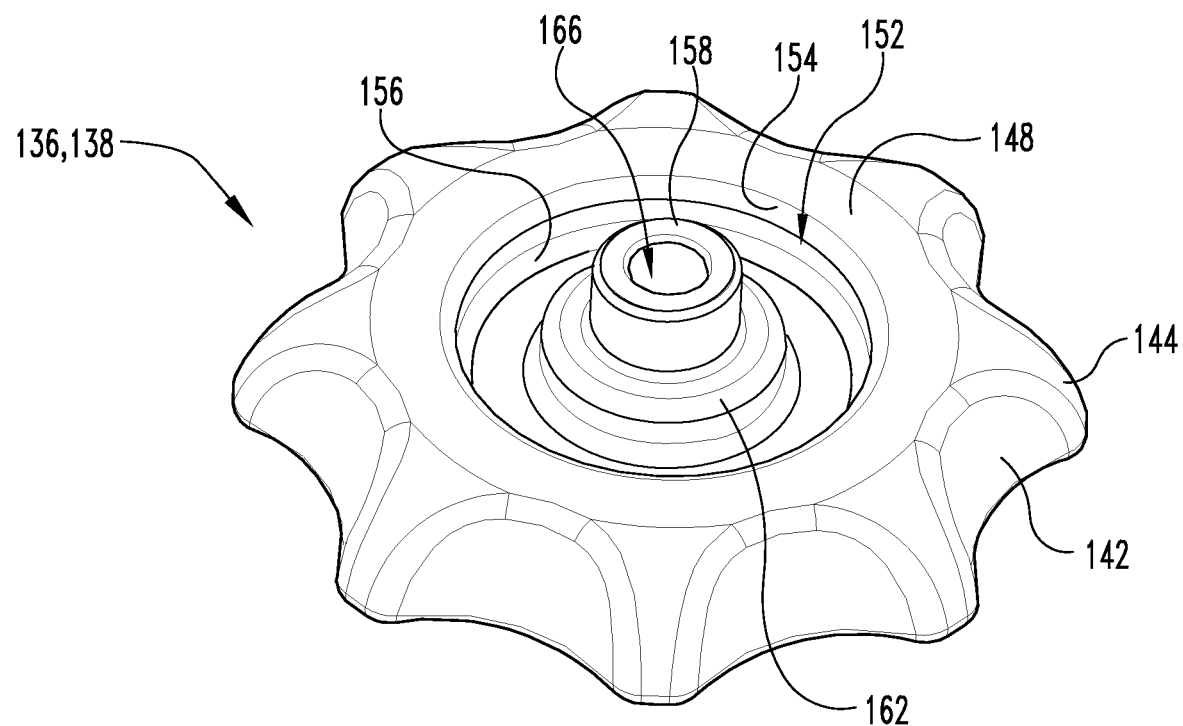
FIG. 7 is an elevated perspective view of an exemplary wheel of the exemplary laparoscopic device of FIG. 1.
Figure 8:
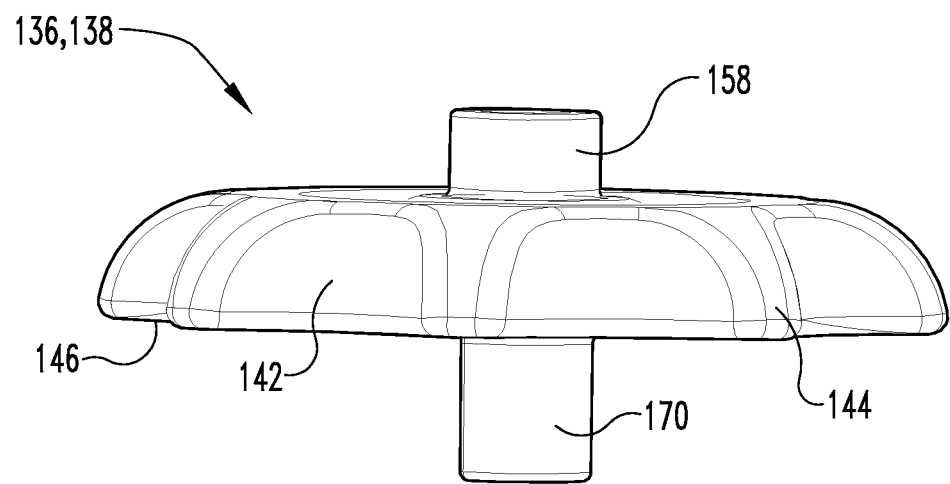
FIG. 8 is a profile view of the exemplary wheel of FIG. 7.
Figure 9:
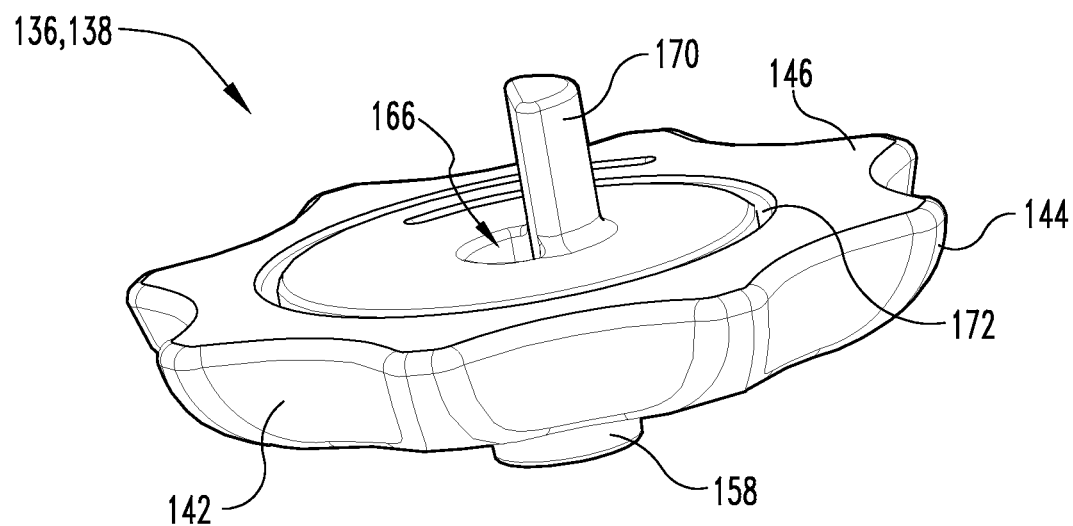
FIG. 9 is an underneath perspective view of the exemplary wheel of FIG. 7.
Figure 10:
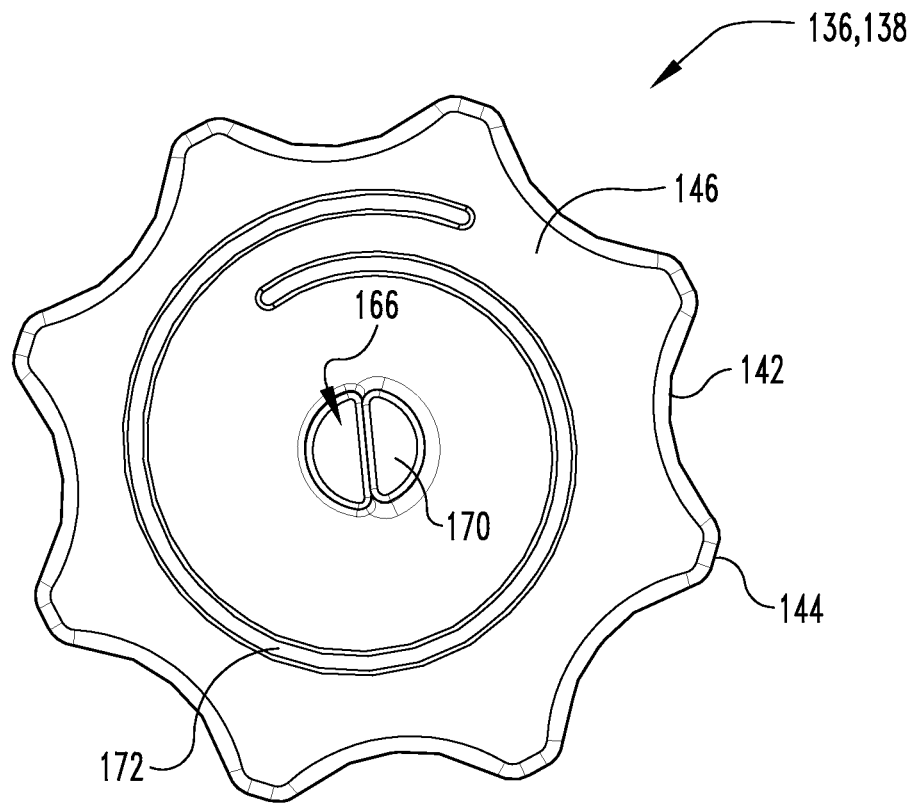
FIG. 10 is a bottom view of the exemplary wheel of FIG. 7.

Referring to FIGS. 5 and 6, the exterior surface 260 of the right side housing 130 also includes a sloped dorsal surface 284 (sloped downward from distal to proximal) that arcuately transitions into a sculpted recess 286 and a bowed medial surface 288 that both transition to a relatively planar ventral surface 290. As will be discussed in more detail hereafter, the ventral surface 290 of the right side housing 130 cooperates with a corresponding ventral surface 294 of the left side housing 132 to partially delineate a handle mechanism port 296 and a handle retention port 298. Both ports 296, 298 are open to the interiors of the respective housings 130, 132. The surfaces 284, 288, 290 converge at the proximal end to partially define a proximal port 300 that is also open to the interior of the housing 130.

Figure 25:
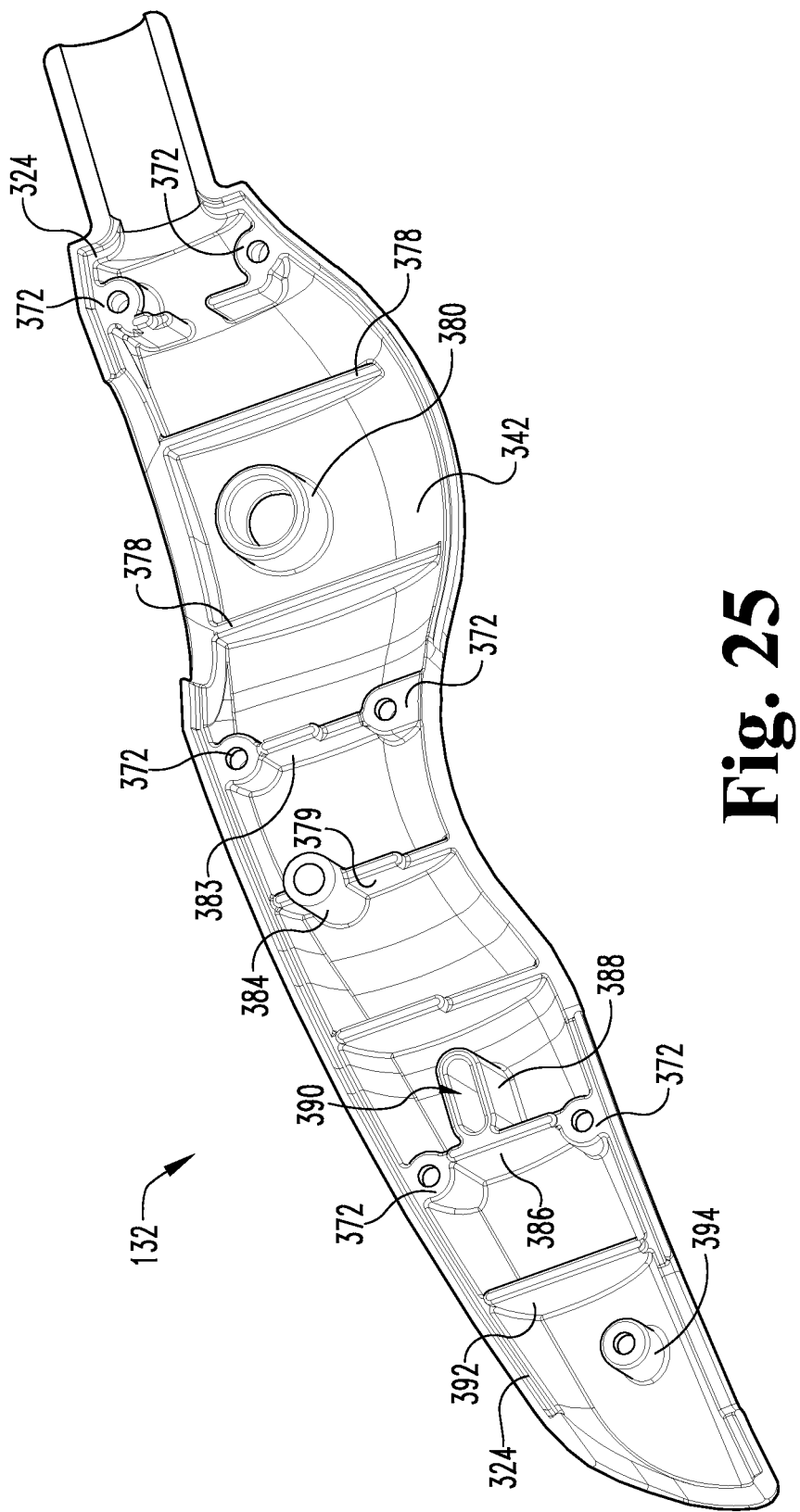
FIG. 25 is an elevated perspective view of the inside of the right side housing of the exemplary laparoscopic device of FIG. 1.
Figure 26:
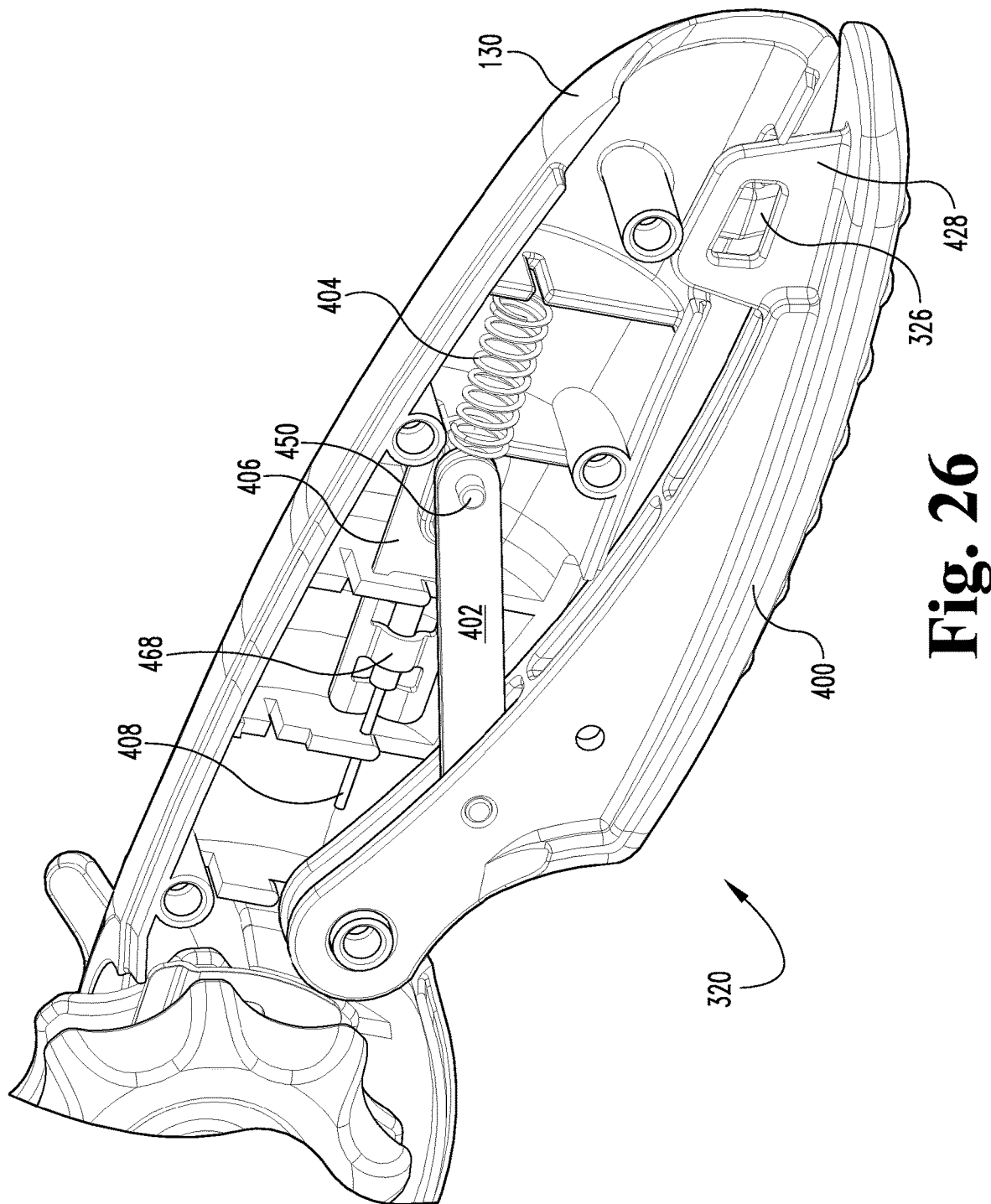
FIG. 26 is a magnified profile view of an interior of a proximal portion of the exemplary controller of the laparoscopic device of FIG. 1, with the left side housing removed.
Figure 27:
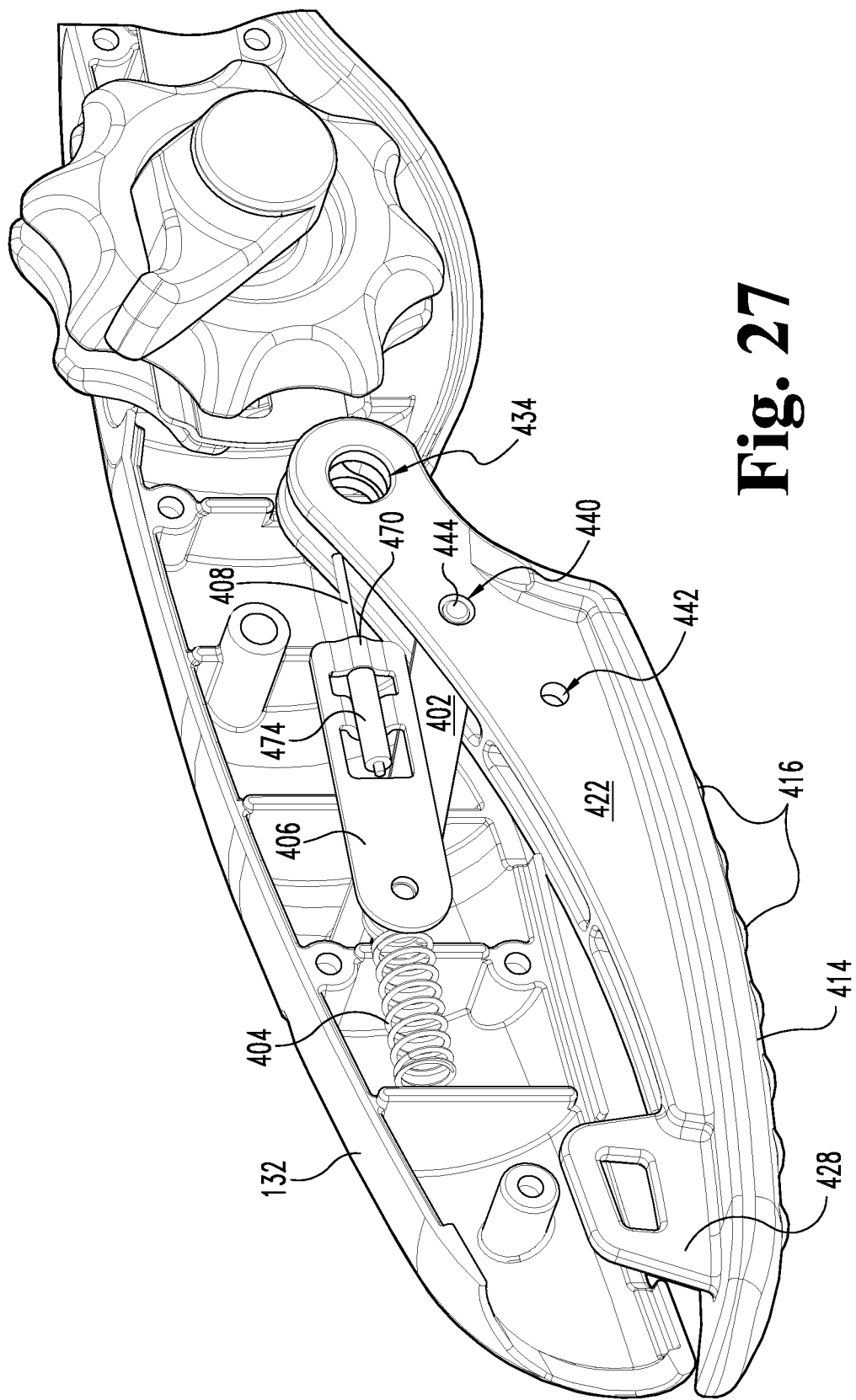
FIG. 27 is a magnified profile view of an interior of a proximal portion of the exemplary controller of FIG. 1, with the right side housing removed.
Figure 28:
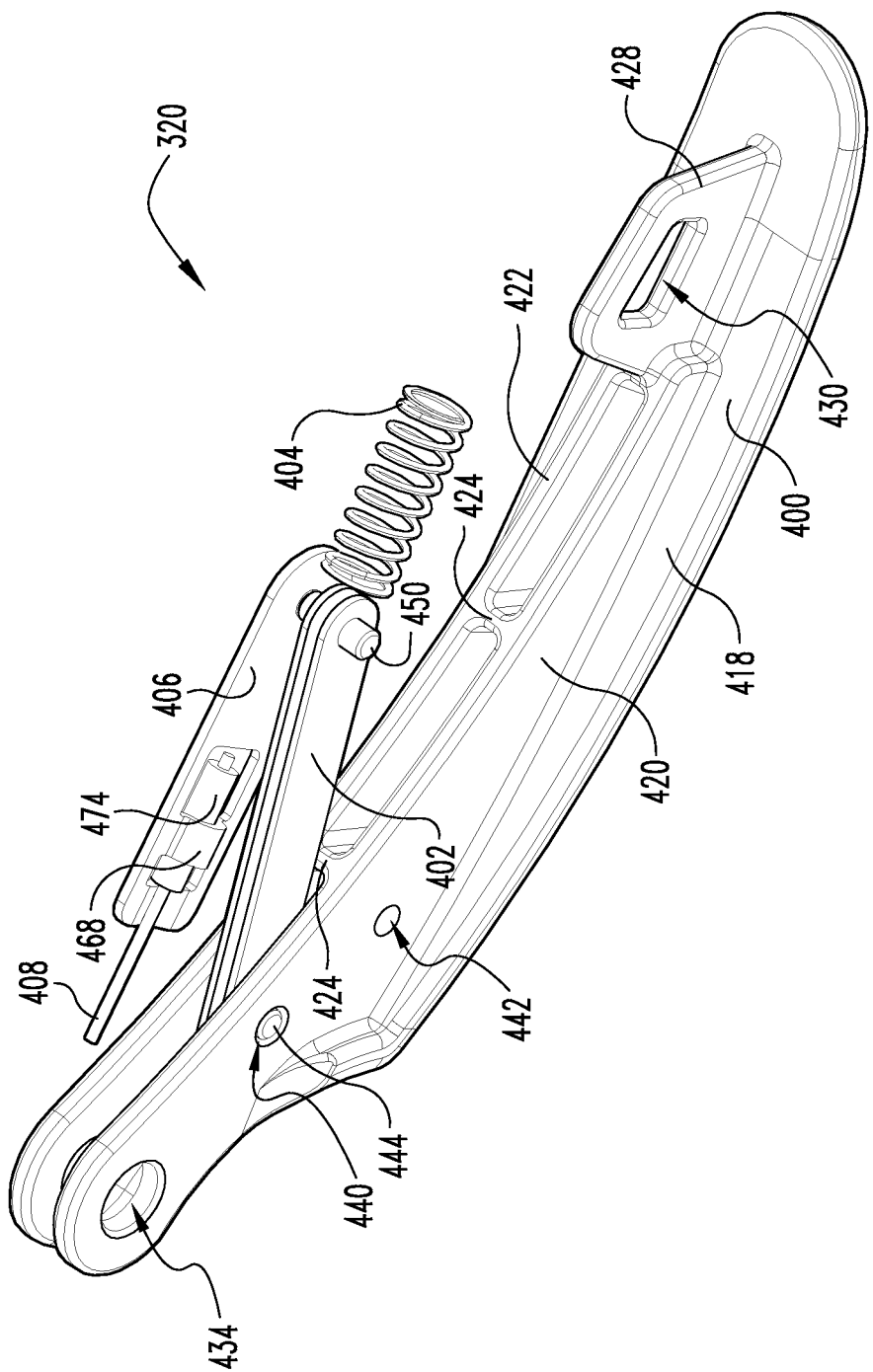
FIG. 28 is an elevated perspective view of an exemplary handle mechanism of the laparoscopic device of FIG. 1.
Figure 29:
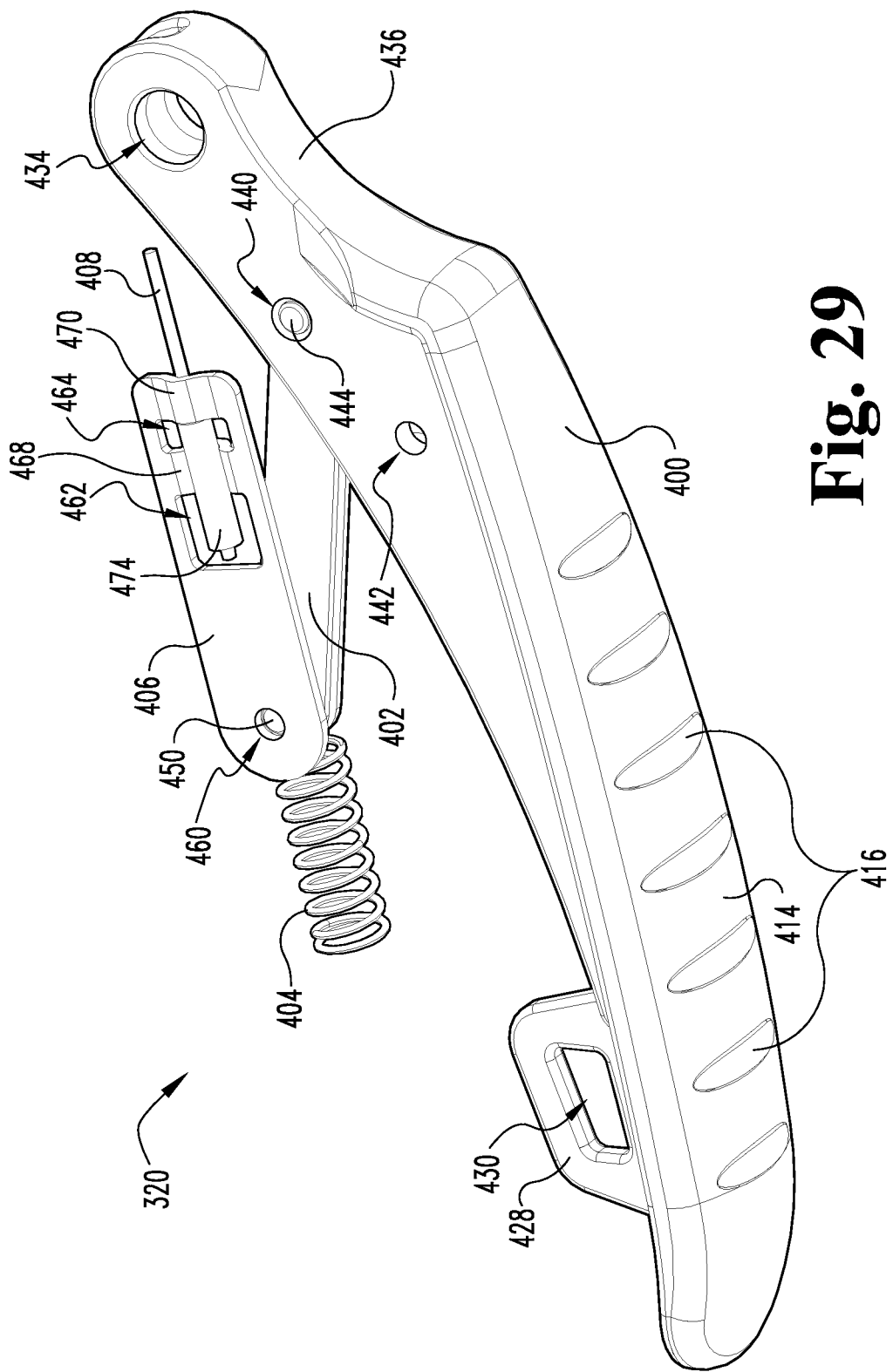
FIG. 29 is an underneath perspective view of the exemplary handle mechanism of FIG. 28.
Figure 30:
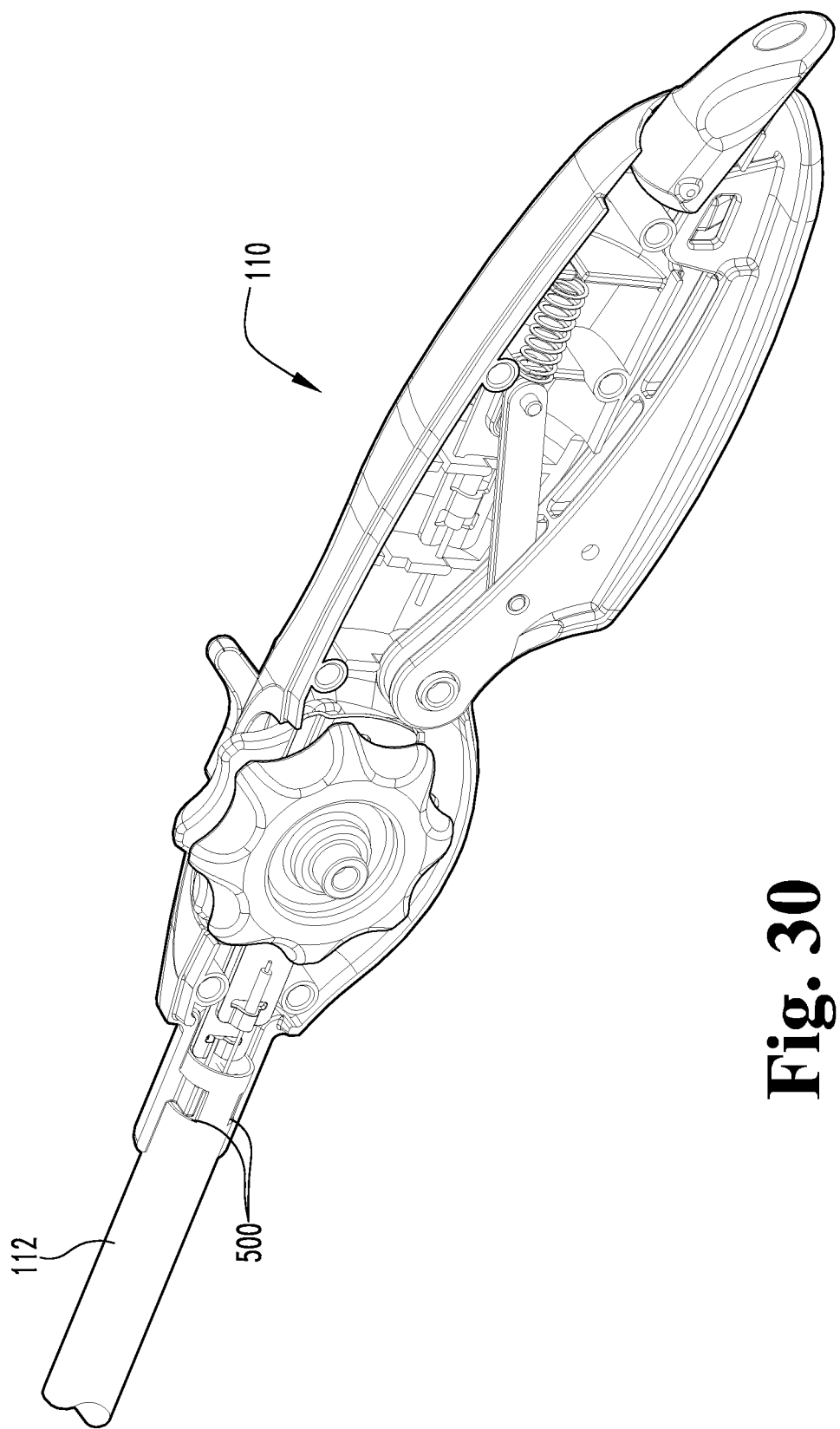
FIG. 30 is an elevated perspective view of the interior of the exemplary controller and proximal portion of the conduit of the exemplary laparoscopic device of FIG. 1, with the left side housing removed.
Figure 31:
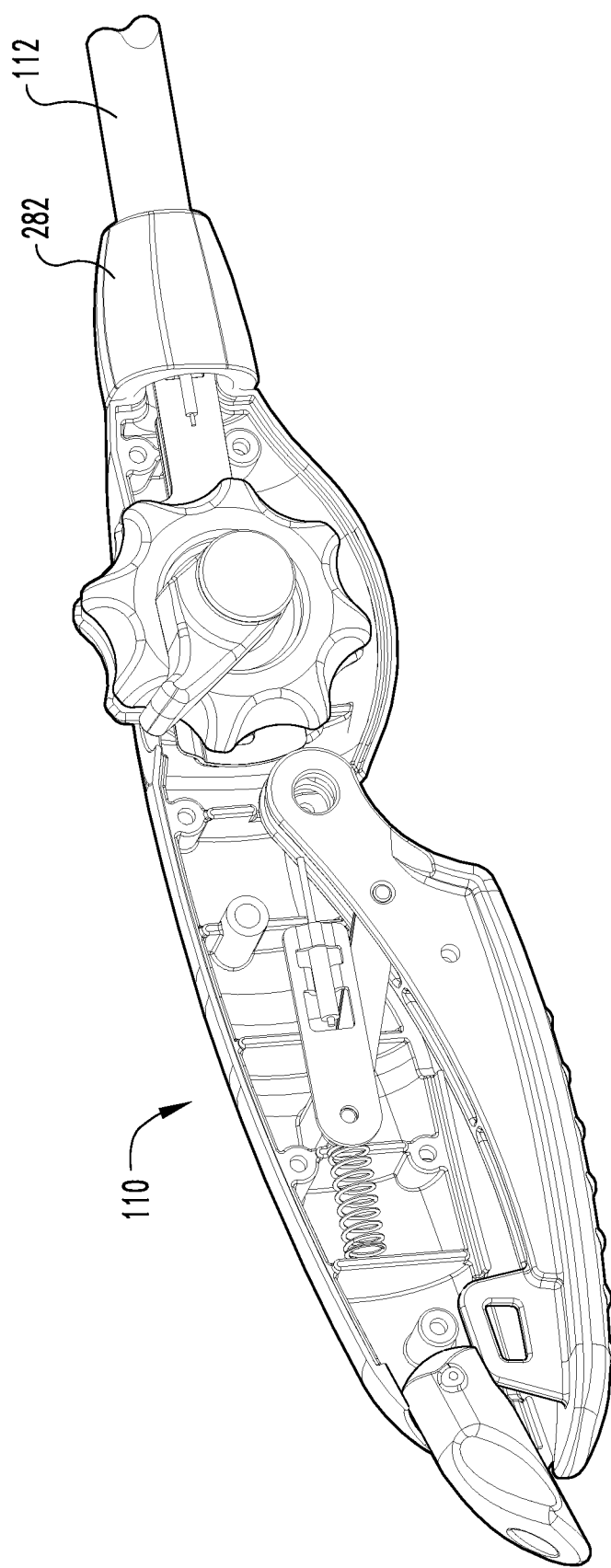
FIG. 31 is an elevated perspective view of the interior of the exemplary controller and proximal portion of the conduit of the exemplary laparoscopic device of FIG. 1, with the right side housing removed and an exemplary cap installed.
Figure 32:
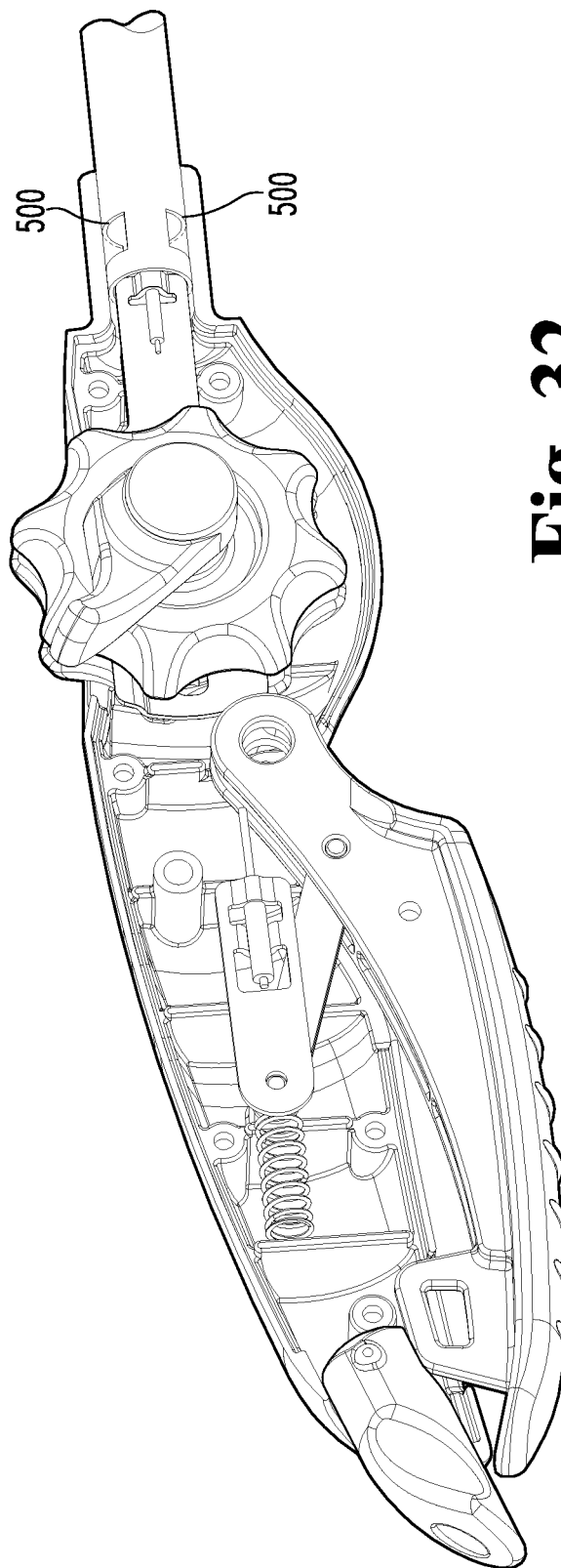
FIG. 32 is an elevated perspective view of the interior of the exemplary controller and proximal portion of the conduit of the exemplary laparoscopic device of FIG. 1, with the right side housing removed and an exemplary cap removed.

Referring back to FIG. 20, the interior of the right side housing includes a series of hollow cylinders 304 that extend generally perpendicularly from the interior surface and are generally parallel to one another. Each cylinder 304 is sized to receive a threaded fastener in order to mount the respective housings 130, 132 to each other. In exemplary form, two of the hollow cylinders 304 are spaced apart from one another by a cross-member 306 having a semicircular cutout. Extending proximally from these hollow cylinders 304 is a pair of stiffening ribs 308 that are partially interposed by a projection 310 having a corresponding shape that defines the exterior depression 230. At the proximal end of the projection 310 are another pair of hollow cylinders 304. These hollow cylinders 304 are followed by another pair of stiffening ribs 308 that interpose a third set of hollow cylinders 304. This pair of hollow cylinders 304 comprising the third set is spaced apart from one another by a cross-member 312 that includes an oblong projection 314 extending proximal-to-distal. As will be discussed hereafter, the oblong projection 314 is hollowed and includes a corresponding cavity 316 that receives a portion of the handle mechanism 320 (see FIG. 26). Finally, a proximal stiffening rib 308 interposes the third set of cylinders and a proximal single cylinder 304. A portion of the perimeter of the interior surface of the right side housing 130 includes a recessed ledge 322 that is received within a corresponding channel 324 (see FIG. 25) of the left side housing 132 in order to align the housings 130, 132. And the interior of the right side housing also includes a detent 326 that extends into the handle retention port 298 and is used to retain the handle mechanism in a set position.

Referring to FIGS. 5, 6, 24, and 25, the left side housing 132 is similar to the right side housing 130 and includes a convex exterior surface 340 and a concave interior surface 342. The interior and exterior surfaces 340, 342 converge to partially define the dorsal opening 134, the handle mechanism port 296, the handle retention port 298, and the proximal port 300.

The left side housing 132 of the controller 110 includes an enlarged section 354, proximate a distal end 352 that is rounded on its underside. This enlarged section 354 tapers proximally and distally to transition into a proximal neck 356 and a distal flange 358. The distal flange 358 interposes the enlarged section 354 and a semi-circular adapter 360. The exterior of the adapter 360 is smooth and semicircular in order to receive the cylindrical cap 282 that circumscribes the exterior of the adapter 360.

The exterior surface 340 of the left side housing 132 also includes a sloped dorsal surface 364 (sloped downward from distal to proximal) that arcuately transitions into a sculpted recess 366 and a bowed lateral surface 368 that both transition to a relatively planar ventral surface 294. The bowed lateral surface 368 includes a plurality of through holes 370 that are partially bounded by corresponding hollow cylinders 372 that extend into the interior of the left side housing 132. These cylinders 372 are adapted to be aligned with the hollow cylinders 304 of the right side housing 130 and receive corresponding fasteners (not shown) in order to mount the housings to each other. Moreover, the ventral surfaces 290, 294 of the housings 130, 132 cooperate to delineate the handle mechanism port 296 and the handle retention port 298. The surfaces 364, 368, 294 converge at the proximal end to partially define the proximal port 300 that is also open to the interior of the housing 132.

The interior of the left side housing 132 includes several hollow cylinders 372 that extend generally perpendicularly from the interior surface 342 and are generally parallel to one another. In exemplary form, two of the hollow cylinders 372 nearest the distal end are spaced apart from one another and have generally the same height. Traveling proximally from these hollow cylinders 372 is a pair of stiffening ribs 378 that are partially interposed by a cylindrical projection 380 having a hollow interior cavity 382 and a longitudinal height approximating the height of the ribs. Traveling proximally from the stiffening ribs 378 are a pair of hollow cylinders 372 that are spaced apart from one another by an L-shaped cross-member 383. It should be noted that the dorsal cylinder 372 has a height relatively the same as the height of the tall portion of the cross-member, while the ventral cylinder has a height relatively the same as the height of the lower portion of the cross-member. Continuing to travel proximally from the L-shaped cross-member 383, a larger hollow cylinder 384 intersects a stiffening rib 379 having a notch cut out of it to resemble the L-shaped cross-member. Further traveling proximally from the larger cylinder 384 is an L-shaped cross-member 385, followed by a pair of hollow cylinders 372 comprising a third set spaced apart from one another by a cross-member 386 that includes an oblong projection 388 extending proximal-to-distal. As will be discussed hereafter, the oblong projection 388 is hollowed and includes a corresponding cavity 390 that receives a portion of the handle mechanism 320. Finally, a proximal stiffening rib 392 interposes the third set of cylinders and a proximal single cylinder 394. A portion of the perimeter of the interior surface 340 of the left side housing 132 includes channels 324 that receive the recessed ledge 322 of the right side housing 130.

Referencing FIGS. 2 and 26-29, the handle mechanism 320 comprises a repositionable handle 400, a drive link 402, a return spring 404, and a draw plate 406. As will be discussed in more detail hereafter, the draw plate 406 is coupled to a draw wire 408 operatively coupled to the clip deployment device 118 in order to selectively open and close an occlusion clip 1160 (see FIG. 75), such as during an atrial appendage occlusion clip deployment surgical procedure. A more detailed explanation of the respective components of the handle mechanism 320 follows.

The repositionable handle 400 includes an arcuate, ventral gripping surface 414 having a series of convex bumps 416 longitudinally spaced apart to facilitate gripping by a user. At the same time, the ventral gripping surface 414 tapers in the medial-to-lateral direction from a maximum in between the proximal and distal ends. Opposite the ventral gripping surface 414 is a corresponding interior surface 418 from which a pair of spaced apart, parallel vertical walls 420, 422 extend. The vertical walls 420, 422 are also connected to one another via a plurality of cross walls 424. The proximal cross wall is also connected to an upstanding loop 428 that provides a through opening 430 in the medial-to-lateral direction. Extending distally from the loop 428, the walls 420, 422 gradually increase in height and extend distally beyond the ventral gripping surface 414. In particular, the distal most portion of the walls 420, 422 each includes a rounded, dorsal end having a circular opening 434 extending in the medial-to-lateral direction. A distal wall 436 spans between the walls 420, 422 at the distal end and transitions into the ventral gripping surface 414. The circular openings 434 of the walls 420, 422 are laterally aligned, as are two other pairs of circular openings 440, 442 extending through the walls in the medial-to-lateral direction. Both paired openings 440, 442 are smaller in diameter than the distal openings 434 and each is adapted to receive a pin 444 in order to repositionably mount the drive link 402 to the handle 400. While only one of the paired openings 440, 442 will be occupied by the pin 444, the other paired opening unoccupied may be used depending upon the spring rate of the return spring 404 and the device (e.g., clip deployment device 118) comprising the end effector 118.

An exemplary drive link 402 comprises a U-shaped, longitudinally extending plate sized to fit between the walls 420, 422 of the handle 400. A distal end of the plate 402 includes the U-shaped bend and a pair of through openings (extending in a medial-to-lateral direction) that receive the pin 444. A proximal end of the plate 402 includes respective legs in parallel to one another and each having a through opening. Each of the legs of the plate 402 is biased by the coiled return spring 404, which contacts the rounded end of each leg. In this exemplary embodiment, the return spring 404 is not rigidly coupled to the drive link 402, but rather is biased against the drive link and retained in position by the bias of the return spring itself pushing against respective stiffening ribs of the housings 130, 132 and the proximal ends of the plate 402. The through openings in the legs receive a second pin 450, which is also concurrently received within the cavity 390 of the oblong projection 388 and within the cavity 316 of the oblong projection 314, that couples the drive link 402 to the draw plate 406.

The draw plate 406 comprises a substantially straight and flat substrate having three openings 460, 462, 464 that extend in the medial-to-lateral direction. The first opening 460 receives the second pin 450 to mount the drive link to the draw plate 406. The second opening 462 comprises a rectangular opening with rounded corners, while the third opening 464 comprises a smaller rectangular opening with rounded corners having a proximal-to-distal dimension that is less than the dorsal-to-ventral dimension. A strip of the draw plate 406 interposes the openings 462, 464 and is deformed to create a lateral half loop 468 concave laterally and convex medially. A second strip of the draw plate 406 at the distal end is also deformed to create a medial half loop 470 convex laterally and concave medially. It should be noted that the lateral half loop 468 is deeper than the medial half loop 470 because the lateral half loop 468 is sized to accommodate a sleeve 474 that circumscribes a proximal portion of the draw wire 408. This sleeve 474 is not readily repositionable longitudinally along the draw wire 408. Accordingly, repositioning of the sleeve 474 while the draw wire 408 is in tension correspondingly causes the draw wire to be repositioned.

The repositionable handle 400 is adapted to be grasped by a user and repositioned from a retained position to a free position. In the retained position (see FIG. 26), the loop 428 of the handle 400 engages the detent 326 of the right side housing 130 to retain the handle adjacent to the housings 130, 132. When a user desires to disengage the handle 400 from the detent 326, the user laterally slides the handle away from the detent and out of engagement with the detent. Thereafter, the bias of the spring 404 is operative to push against the drive link 402, which itself pushes against the handle 400 to force the handle away from the housings 130, 132. At the same time, the draw plate 406 is also repositioned. When the handle 400 engages the detent 326, the draw plate is fully retracted in a proximal-most position. As will be discussed in more detail hereafter, the proximal-most position of the draw plate 406 results in the draw wire 408, which is also mounted to the pull link 764, being pulled proximally to open the occlusion clip 1160. Conversely, when the handle 400 disengages the detent 326 and is moved away from the housings 130, 132, the draw plate is repositioned in a distal direction. Eventually, if the handle 400 is repositioned to the maximum travel away from the housings 130, 132, the draw plate 406 is positioned in a distal-most position. As will be discussed in more detail hereafter, the distal-most position of the draw plate 406 results in the draw wire 408 repositioned distally in order to close the occlusion clip 1160.

Figure 3:
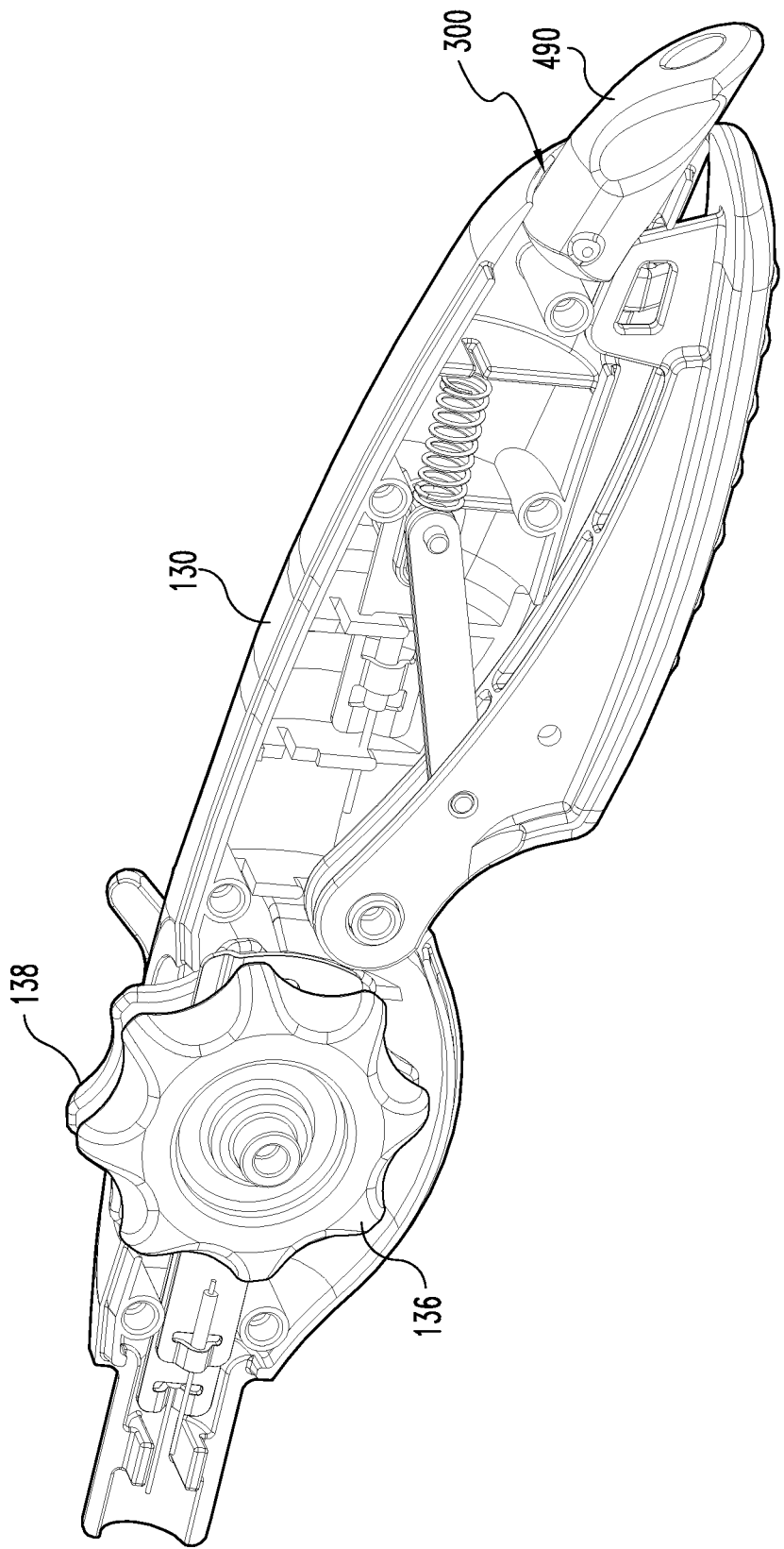
FIG. 3 is an elevated perspective view of the proximal end of the exemplary laparoscopic device of FIG. 2, without the left side housing.
Figure 4:
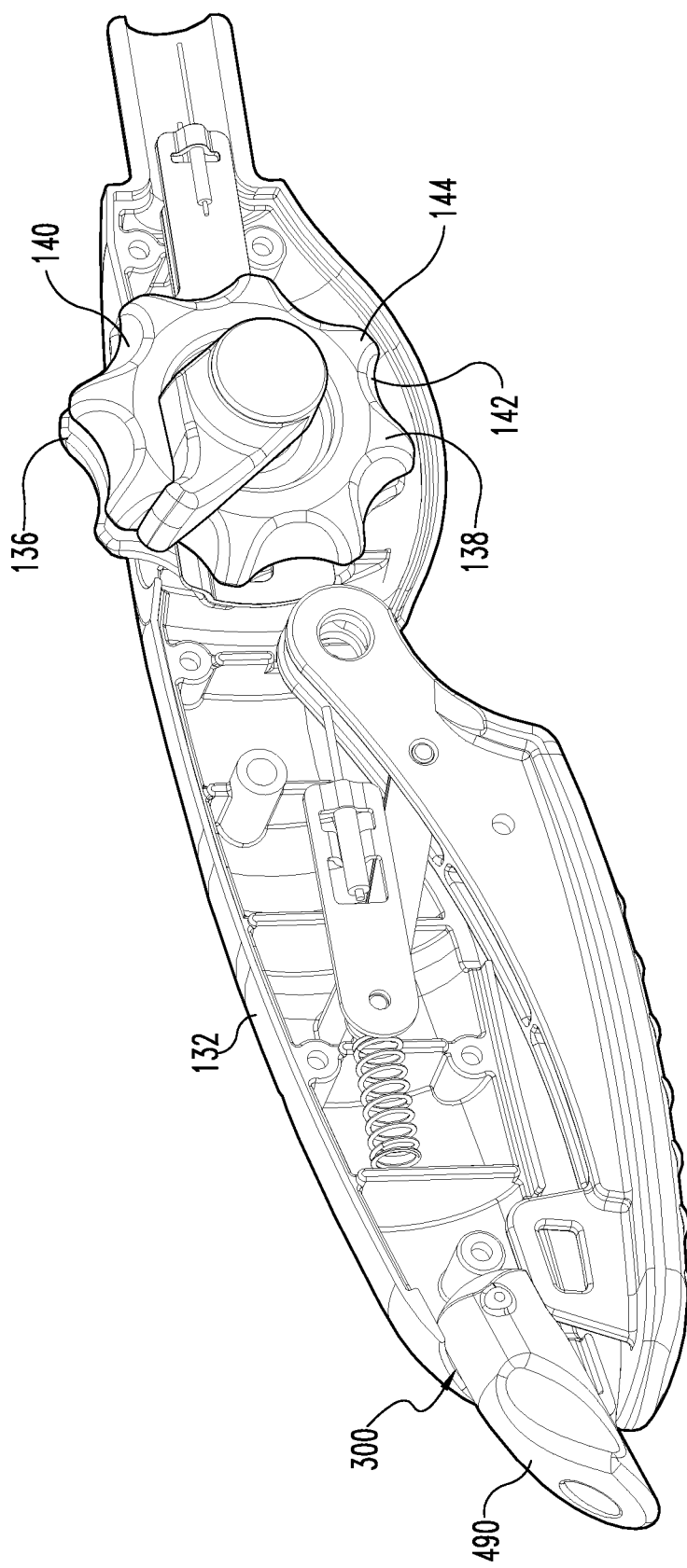
FIG. 4 is an elevated perspective view of the proximal end of the exemplary laparoscopic device of FIG. 2, without the right side housing.

Referring to FIGS. 2-4, the controller 110 also includes a removable stem 490 that is seated within the proximal port 300 of the housings 130, 132. The removable stem 490 is coupled to one or more clip release wires 492 (in this case, two clip release wires) that act to disconnect an occlusion clip from the clip deployment device 118. In this manner, the stem may be removed from the proximal end of the controller 110, thereby drawing the release wire(s) proximally and disconnecting the occlusion clip from the clip deployment device 118. In this exemplary embodiment, the stem 490 is secured within the proximal port 300 via a friction fit that may be overcome by the user applying pressure to the stem to move it proximally with respect to the controller 110. But it is also within the scope of the disclosure to use detents or other affirmative release mechanisms to release the stem 490 from the controller 110.

Referencing back to FIGS. 2-32, assembly of the controller 110 includes mounting the wheels 136, 138 to one another so that the interior faces 146 of the wheels sandwich the link plates 180 therebetween. A detailed discussion of assembly of the wheels 136, 138 and link plates 180 has already been provided and will not be repeated for purpose of brevity. Thereafter, the wheels 136, 138 are oriented so that the axles 158 face in opposite directions and are received respectively within the cylindrical projection 380 of the left side housing 132 and within the circular bearing surface 242 of the right side housing 130. Likewise, the drive link 402 is mounted to the right and left side housings 130, 132 by way of the pin 450 concurrently received within the cavities 316, 390 of the oblong projections 314, 388. In exemplary form, the drive link 402 and right side housing 130 sandwich the draw plate 406 therebetween. At the same time, the drive link 402 is mounted to the handle 400, while the circular opening 434 of the handle receives a cylinder 304 of the right side housing 130 in order to rotationally mount the handle to the housing. Moreover, the spring 404 is inset within the right side housing 130 so that the spring interposes the proximal stiffening rib 308 and the drive link 402. Finally, the removable stem 490 is inserted between the housings 130, 132 and thereafter, the housings 130, 132 are mounted to one another to close the controller. At this time, the draw wire 408, the clip release wires 492, the connection wires 194, and the connection wire 261 all extend through the distal end 262 of the housings 130, 132.

Referring to FIGS. 20 and 30-32, the controller 110 is mounted to a semi-rigid conduit 112 that is relatively linear and has a relatively constant circular cross section. In this exemplary embodiment, the conduit 112 is fabricated from stainless steel and includes a proximal circular opening and a distal circular opening. The proximal circular opening provides access between the interior of the conduit 112 and the interior of the controller 110. More specifically, the hollow interior of the conduit 112 accommodates throughput of the draw wire 408, the clip release wires 492, the connection wires 194, and the connection wire 261. The conduit 112 includes a proximal section having a pair of rectangular, arcuate cut-outs 500. These cutouts 500 provide respective openings for the detents 272 of the adapter 270 to occupy and mount the conduit 112 to the housings 130, 132.

Figure 33:
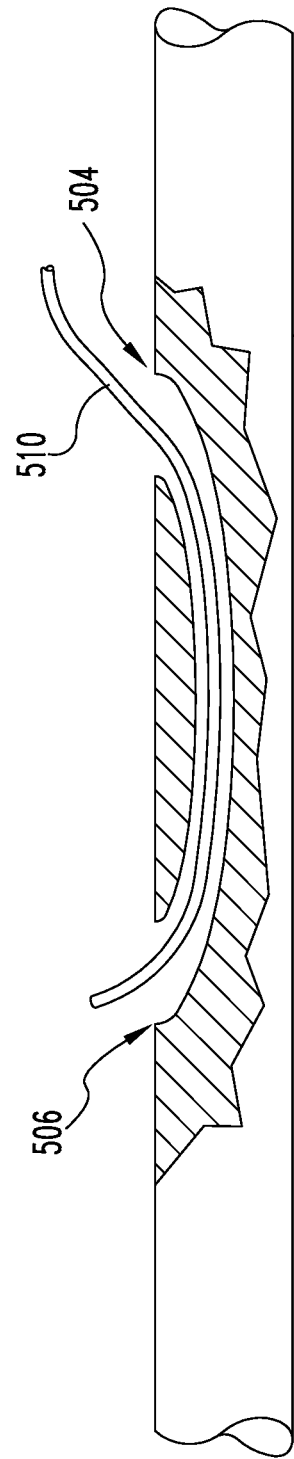
FIG. 33 is a longitudinal cross-sectional view of an alternate exemplary conduit for use with the laparoscopic device of FIG. 1.
Figure 34:
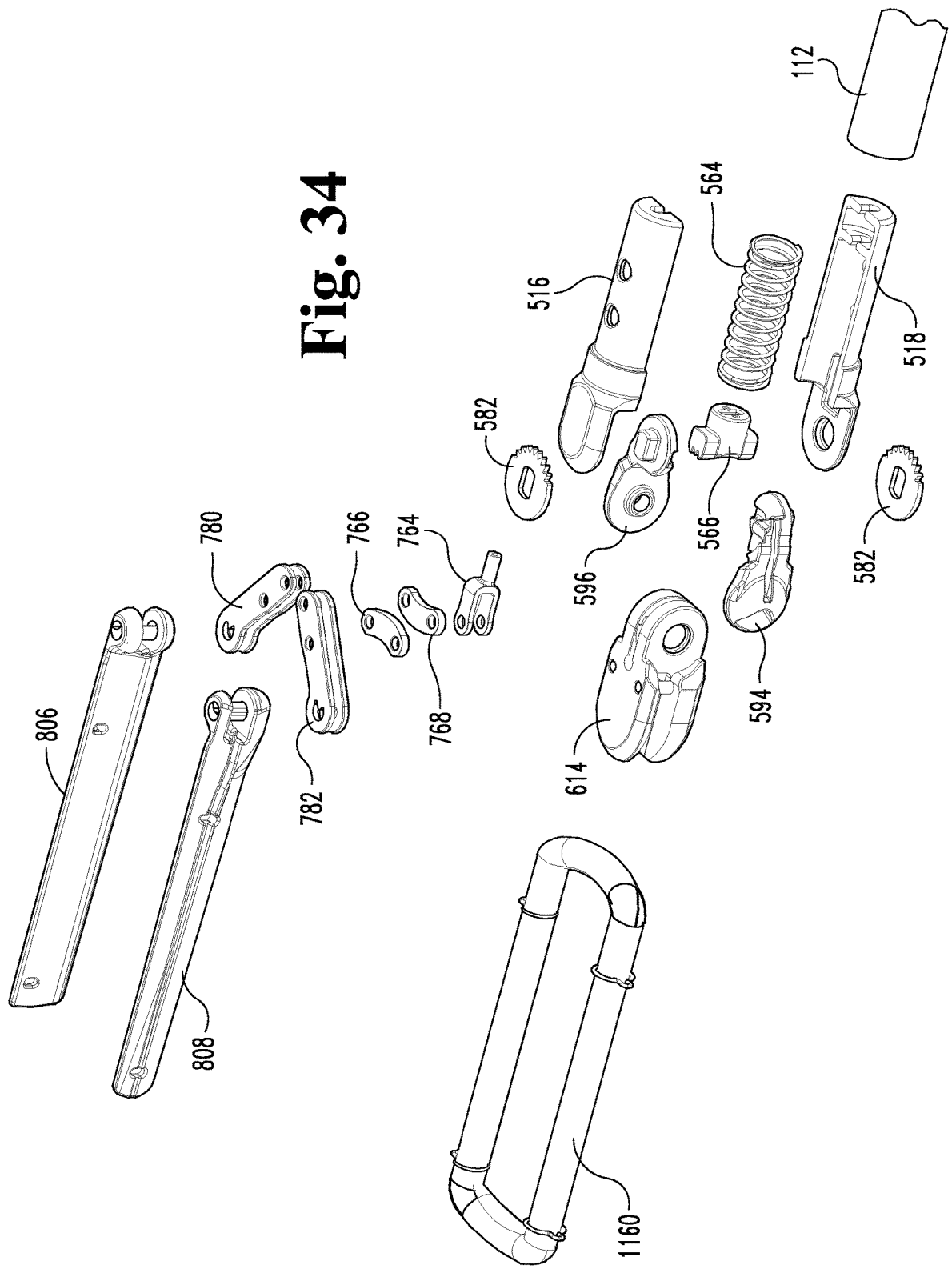
FIG. 34 is an exploded view of the distal end of the exemplary laparoscopic device of FIG. 1.

In addition, as shown in FIG. 33, the semi-rigid conduit 112 may be relatively linear but include two additional orifices 504, 506 that accommodate a separate conduit 508 adapted to provide a separate avenue for an exploratory tool 510. Exemplary exploratory tools for use with the instant semi-rigid conduit include, without limitation, forceps, ablation rails, jaws, linear cutters, ablation pens, ablation clamps, illuminated dissectors, and non-illuminated dissectors. The exemplary exploratory tool 510 may be used in combination with the end effector, which is manipulated by the repositionable mechanism 116.

Referring to FIGS. 34-38, a distal portion of the exemplary repositionable mechanism 116 comprises a clevis 514 comprising ventral and dorsal clevis housings 516, 518. Each housing 516, 518 is a mirror image of the other and includes a convex, semi-cylindrical proximal section 522 having a partially enclosed semicircular proximal end 524 except for a notch 526. Extending longitudinally in a distal direction, the exterior surface of the semi-cylindrical proximal section 522 includes a pair of through holes 530 extending into the interior of the housing that are generally longitudinally aligned and positioned to lie along the apex of the cylindrical proximal section 522. Extending longitudinally in a distal direction beyond the through holes 530 is a semi-cylindrical collar 532 operative to increase the diameter of the housing 516, 518 in comparison to the cylindrical proximal section 522 that has a generally constant diameter. Extending distally from the collar 532 is an overhang 536. The overhang 536 includes a generally planar exterior surface 538 that transitions into a sloped perimeter surface 540 embodying parallel sides with a rounded proximal end 542. The perimeter surface adjoins a substantially planar interior surface 544 that is substantially in parallel with the planar exterior surface 538. The interior surface 544 includes a circular depression 546 and includes a circular circumferential surface 548 that extends between the interior surface and a bottom, planar surface 550 of the depression. The interior surface also includes a portion of a rectangular depression 552 that continues distally into a concave, semi-cylindrical interior surface 554 of the collar 532. It should be noted that the semi-cylindrical interior surface 554 of the collar 532 takes on the same dimensions as the semi-cylindrical interior surface of the cylindrical proximal section 522. But the semi-cylindrical interior surface 554 of the cylindrical proximal section 522 includes a distal rib 558 having generally the same shape as the partially enclosed semicircular distal end 524. Similar to the semicircular distal end 524, the distal rib 558 also includes a notch 560 that is longitudinally aligned with the other notch 526 so that the notches have generally the same dimensions. When the housings 516, 518 are brought together, the distal ribs 558 are aligned over one another so that the notches 560, 526 cooperate to provide a pair of through openings. At the same time, the distal ends 524 of the housings are also aligned to create an internal cavity that houses a bias spring 564 and a tooth receiver 566 as part of the clevis 514.

Referring to FIGS. 36, 37, and 39-41, the tooth receiver 566 includes a proximal cylindrical portion 568 having a uniform circular cross-section and extending substantially linearly. The uniform circular cross-section is sized to be received within the bias spring 564 upon assembly. The proximal cylindrical portion 568 is hollow and includes a circular proximal end wall 570 having a pair of circular openings 572 each adapted to accommodate throughput of the connection wires 194. A larger, oblong opening 574 interposes the circular openings 572 and is adapted to accommodate throughput of the draw wire 408 and the clip release wires 492. Extending distally from the cylindrical portion 568 is a tooth receiving head 576 having medial M and lateral L sections that extend medially and laterally from the cylindrical portion. Interposing the medial and lateral sections is a cylindrical cavity 577 aligned with the hollow cavity of the proximal cylindrical portion 568. Each section of the tooth receiving head 576 includes a generally rectangular cross-section, but for a series of distal teeth 578. Specifically, the teeth 578 have a sawtooth pattern and are formed to extend in the medial-to-lateral direction (perpendicular to a longitudinal axis extending through the cylindrical portion 568). In this exemplary embodiment, the teeth 578 are sized to receive respective teeth 580 from a pair of toothed plates 582.

Figure 42:
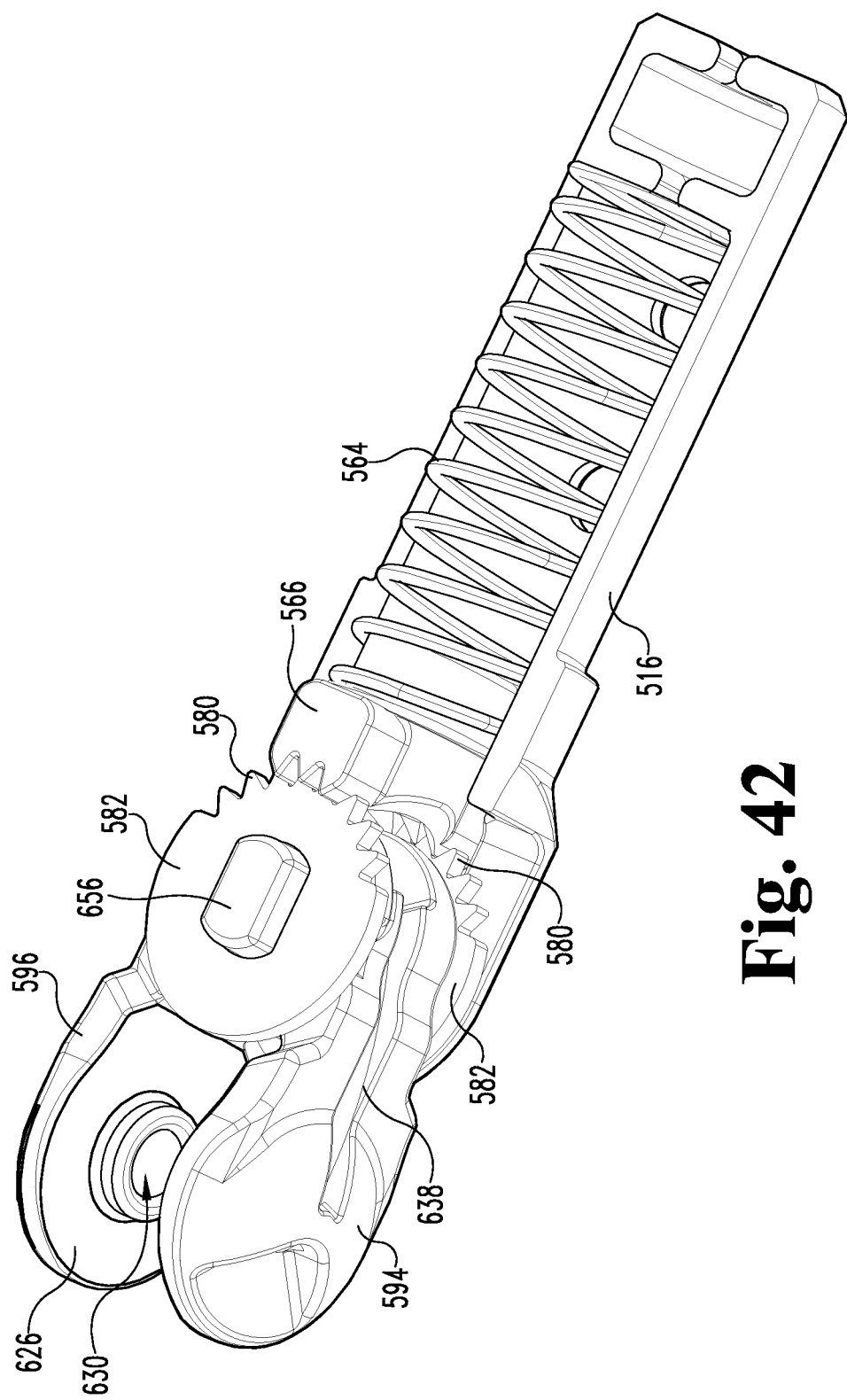
FIG. 42 is an elevated perspective view of an exemplary clevis of FIG. 35, without the top housing, and with a pair of toothed plates and pelvis halves.
Figure 43:
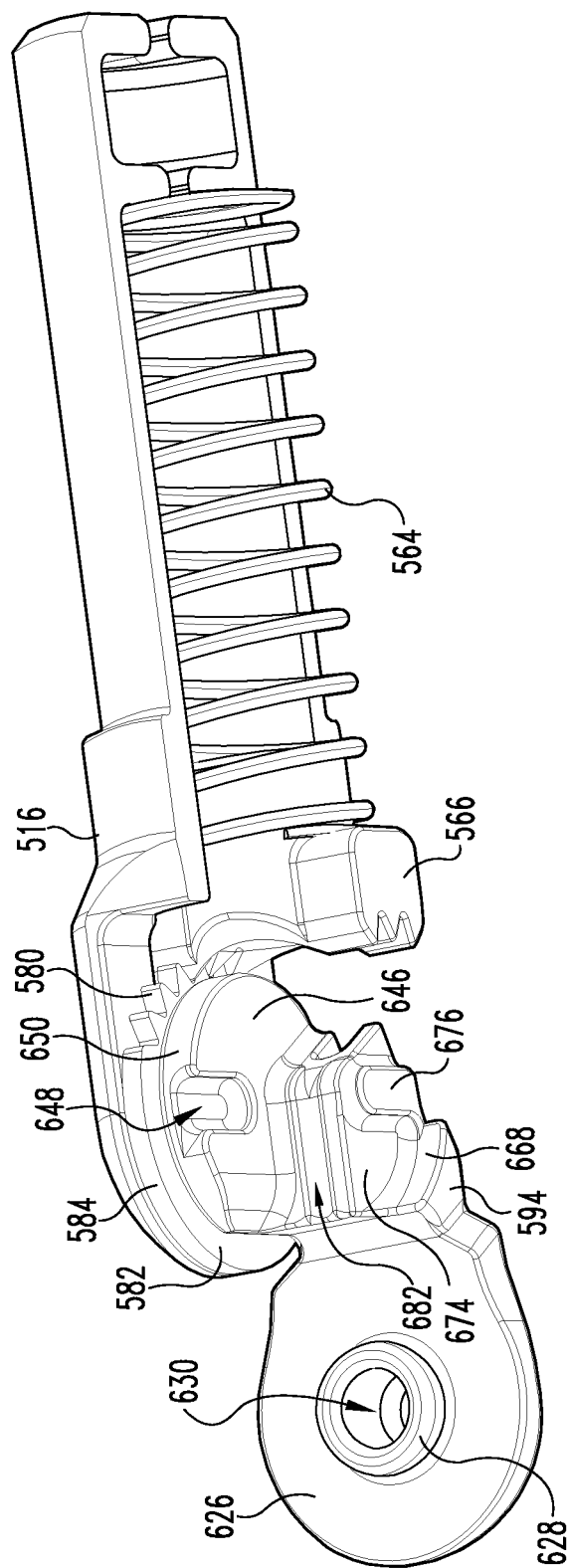
FIG. 43 is an elevated perspective view of an exemplary clevis of FIG. 35, without the top housing, and with single toothed plate and single pelvis half.
Figure 44:
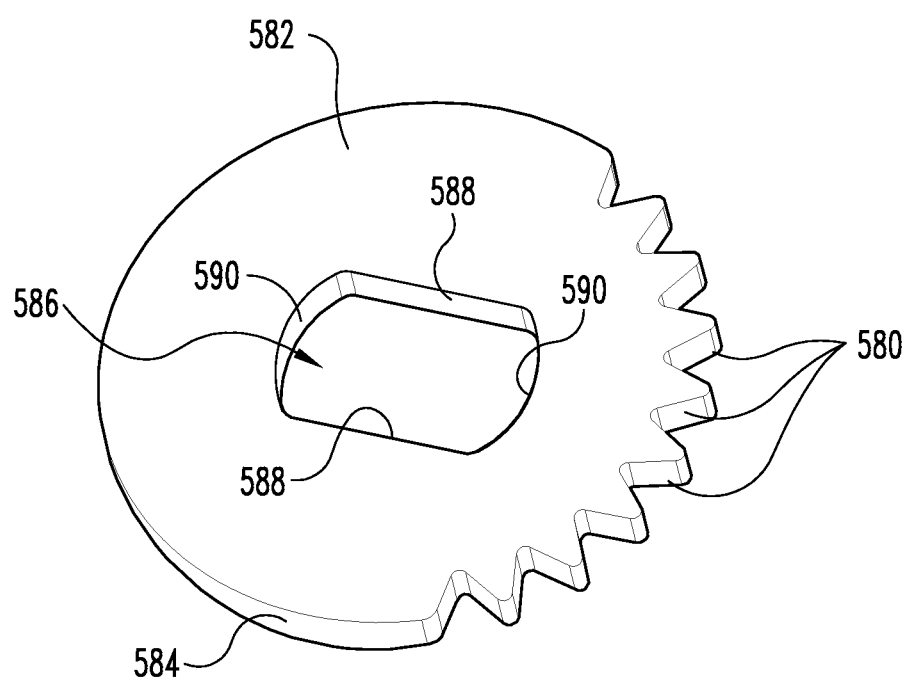
FIG. 44 is an elevated perspective view of an exemplary toothed plate of the exemplary laparoscopic device of FIG. 1.
Figure 45:
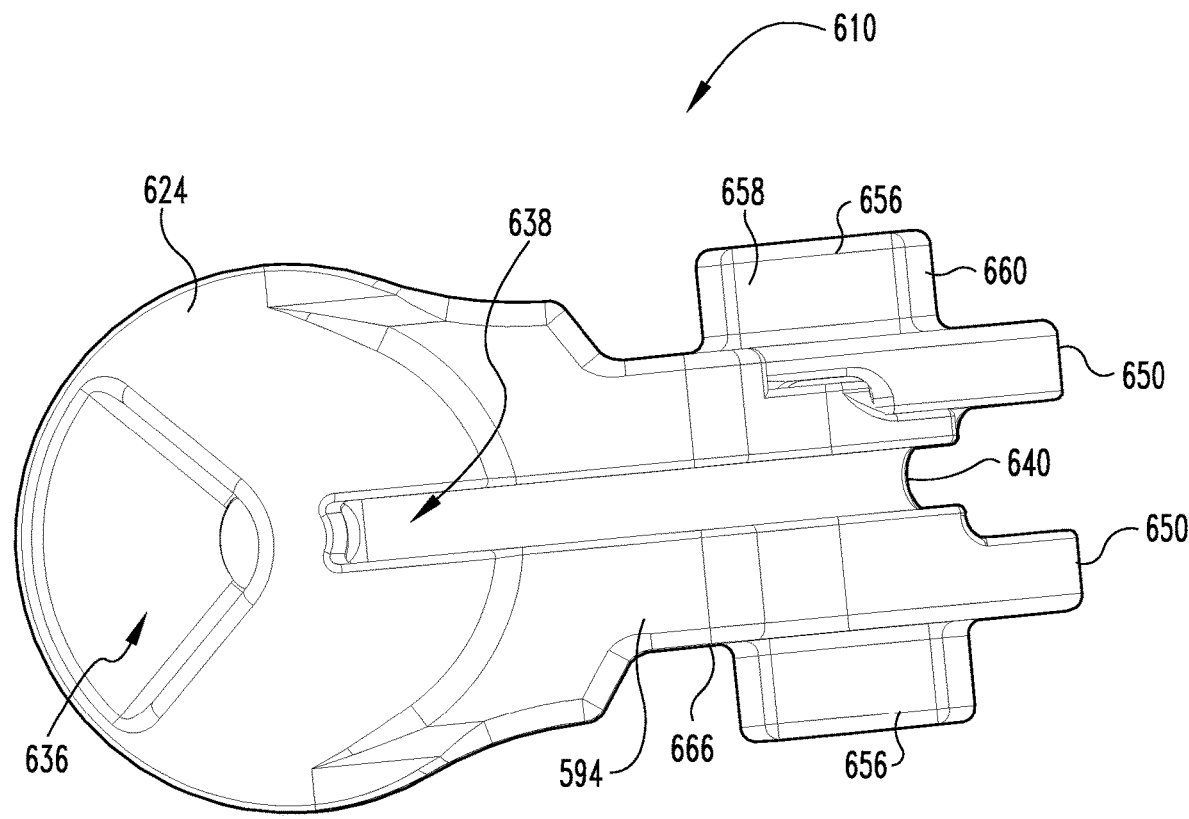
FIG. 45 is an outside profile view of an exemplary pelvis half of the exemplary laparoscopic device of FIG. 1.
Figure 46:
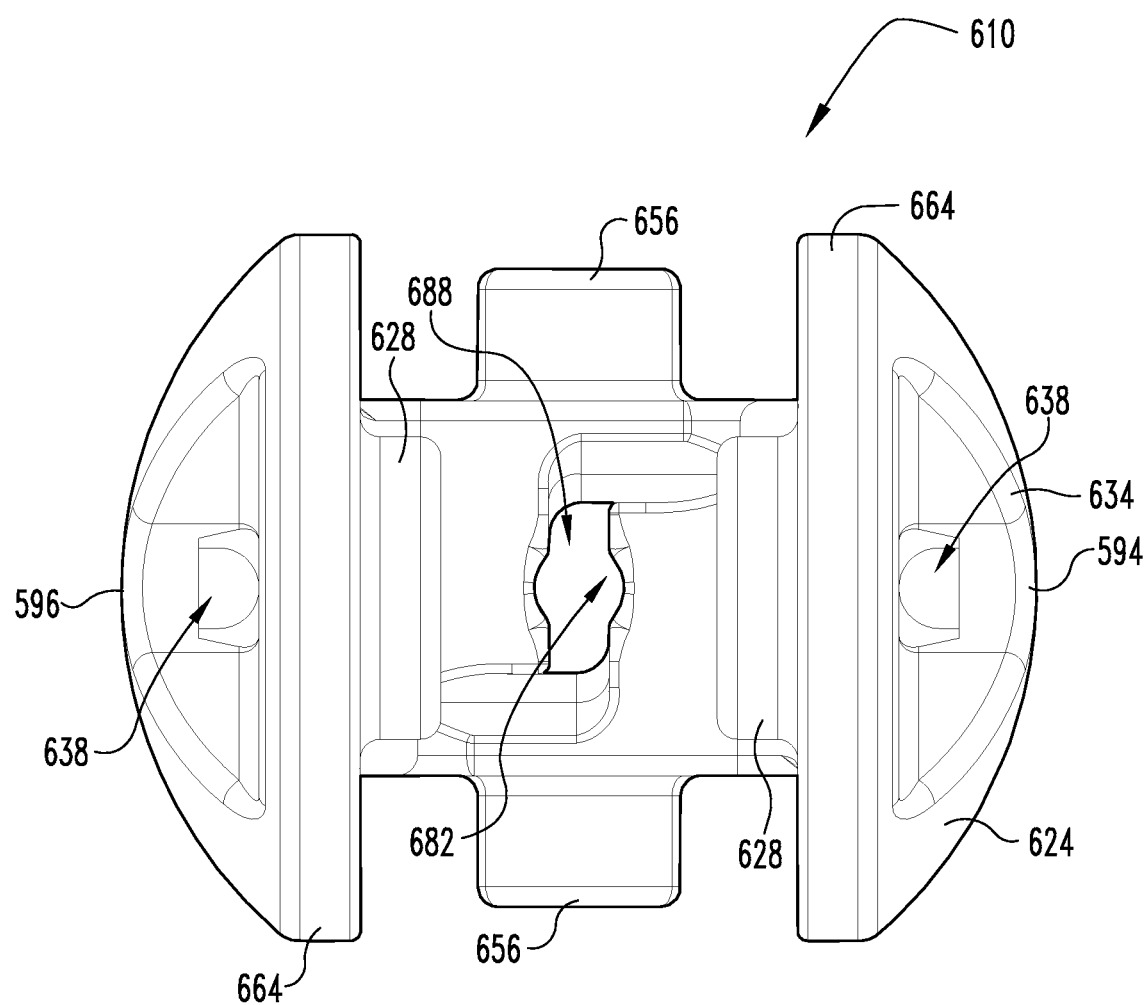
FIG. 46 is a front profile view showing the pelvis halves of FIG. 42 assembled.
Figure 47:
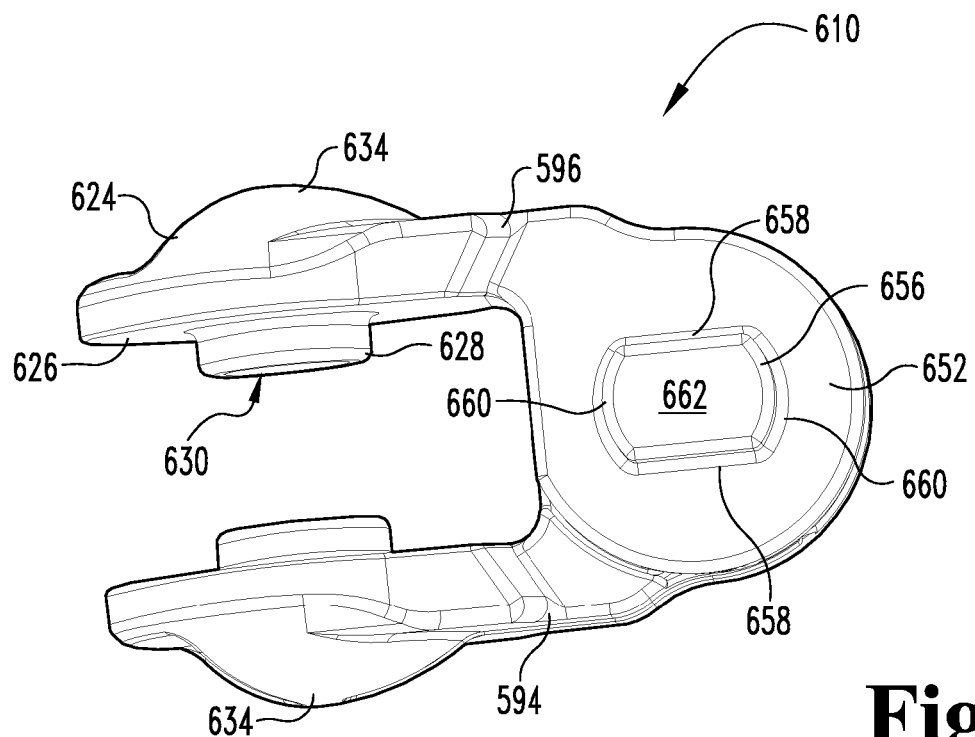
FIG. 47 is an overhead view of the pelvis halves of FIG. 46
Figure 48:
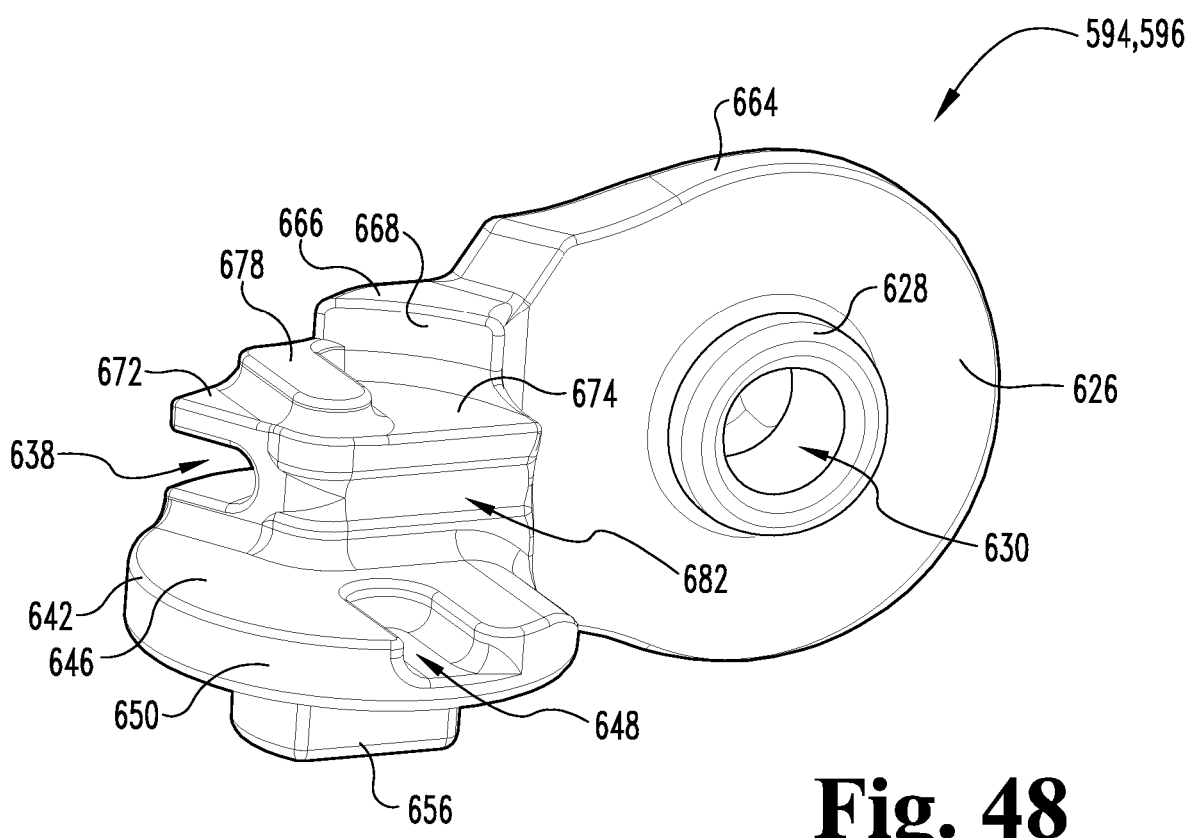
FIG. 48 an inside elevated perspective view of an exemplary pelvis half of the exemplary laparoscopic device of FIG. 1.

Referring to FIGS. 42-44, the toothed plates 582 are also part of the clevis 514 and each toothed plate 582 comprises a circular, generally flat plate. Approximately two hundred and twenty-five degrees of the plate has a circular circumferential surface 584. But the remaining one hundred and thirty-five degrees of the circumferential surface is formed to include a series of teeth 580. As discussed above, the teeth 580 are sized to be received in between the teeth 578 of the tooth receiver 566. Centered within the middle of each toothed plate 582 is a through opening 586 delineated by parallel, linear sides 588 and arcuate ends 590. These through openings 586 are adapted to receive a respective pelvis half 594 in order to allow or limit lateral movement of the pelvis half.

Figure 35:
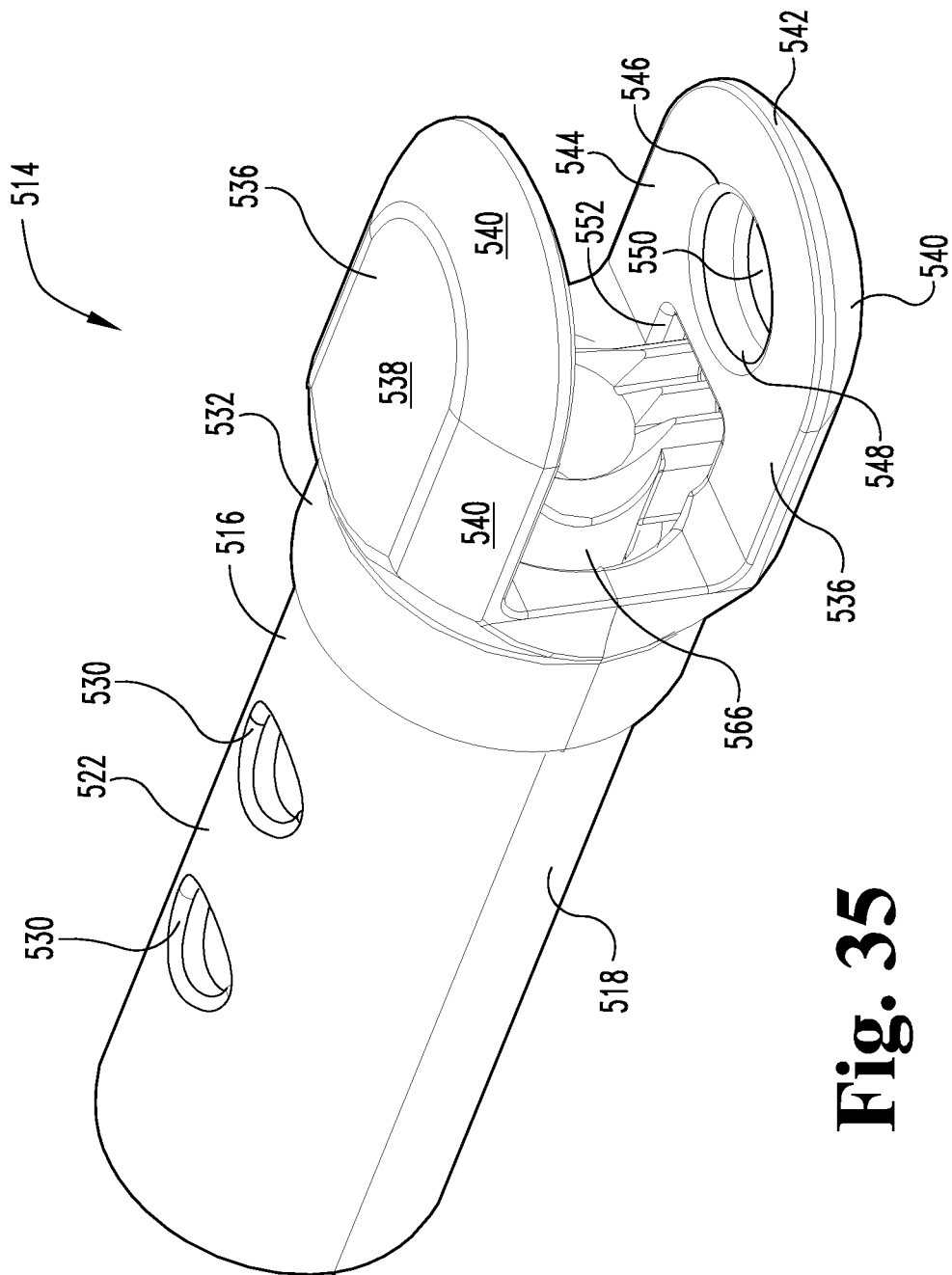
FIG. 35 is an elevated perspective view of an exemplary clevis of the exemplary laparoscopic device of FIG. 1.
Figure 36:
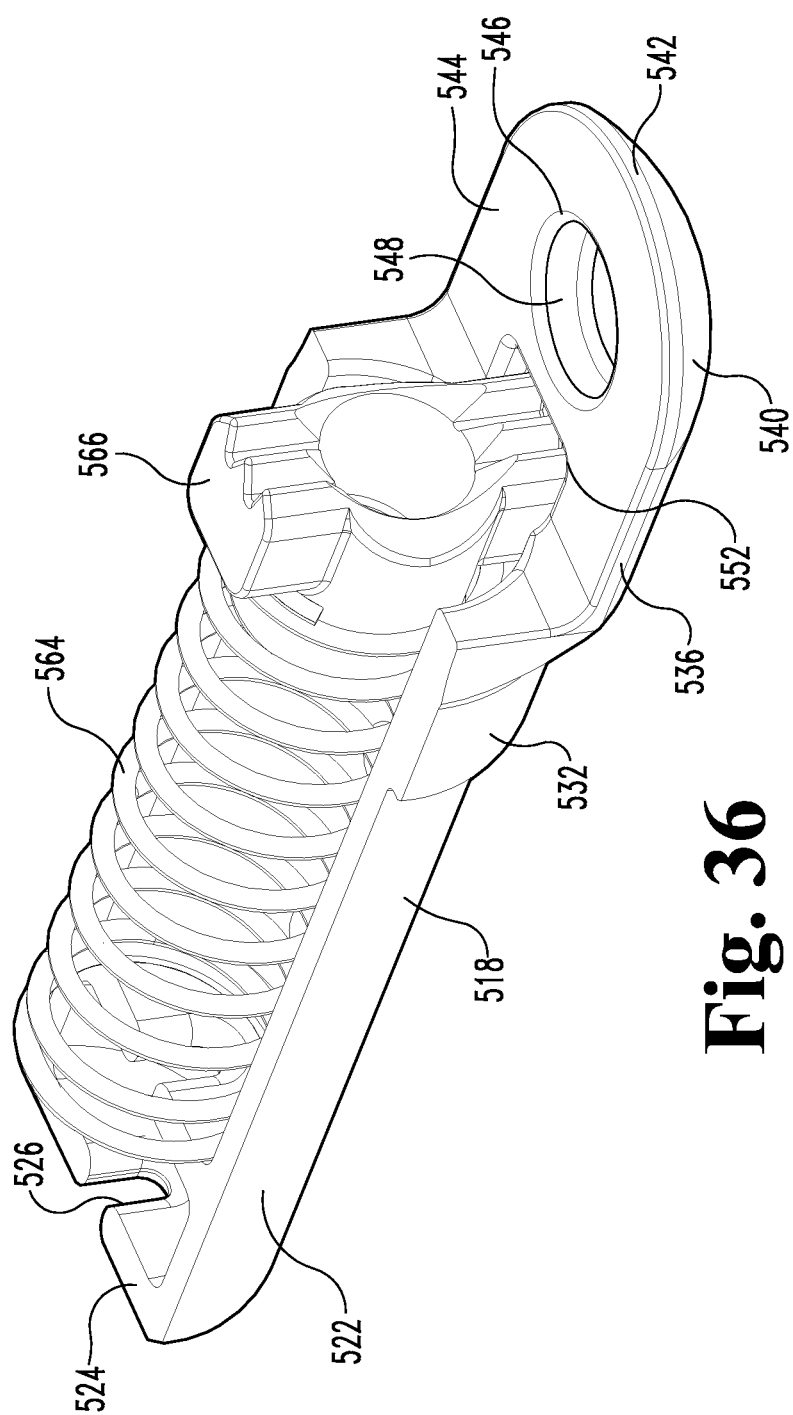
FIG. 36 is an elevated perspective view of an exemplary clevis of FIG. 35, without the top housing.
Figure 37:
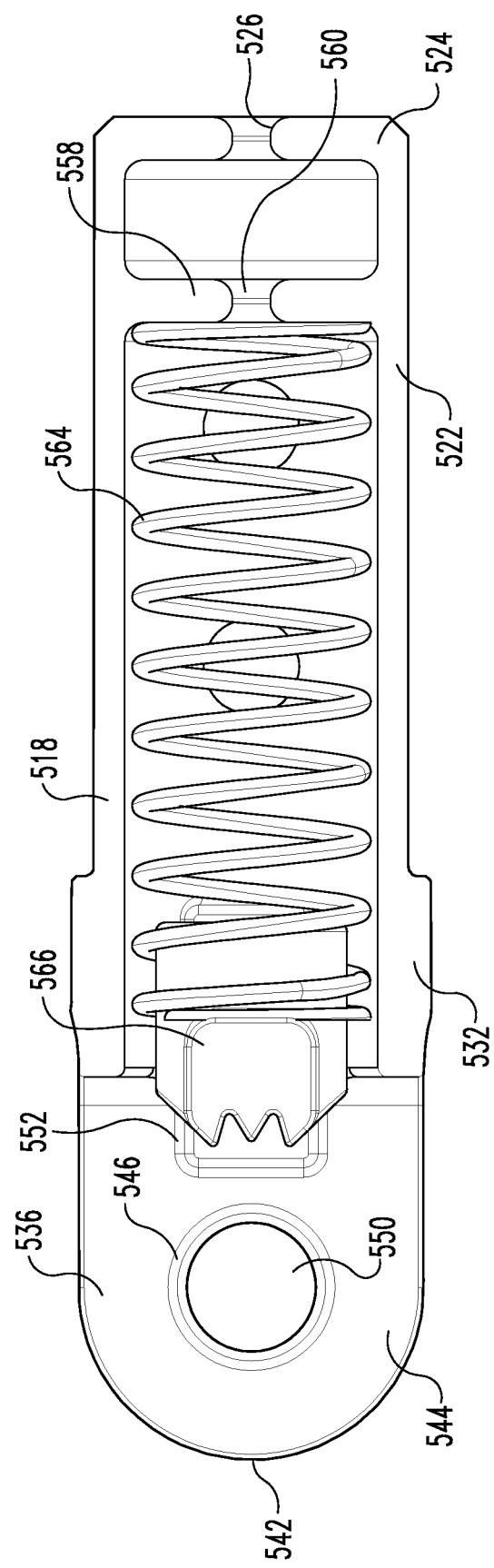
FIG. 37 is an overhead view of an exemplary clevis of FIG. 36.
Figure 38:
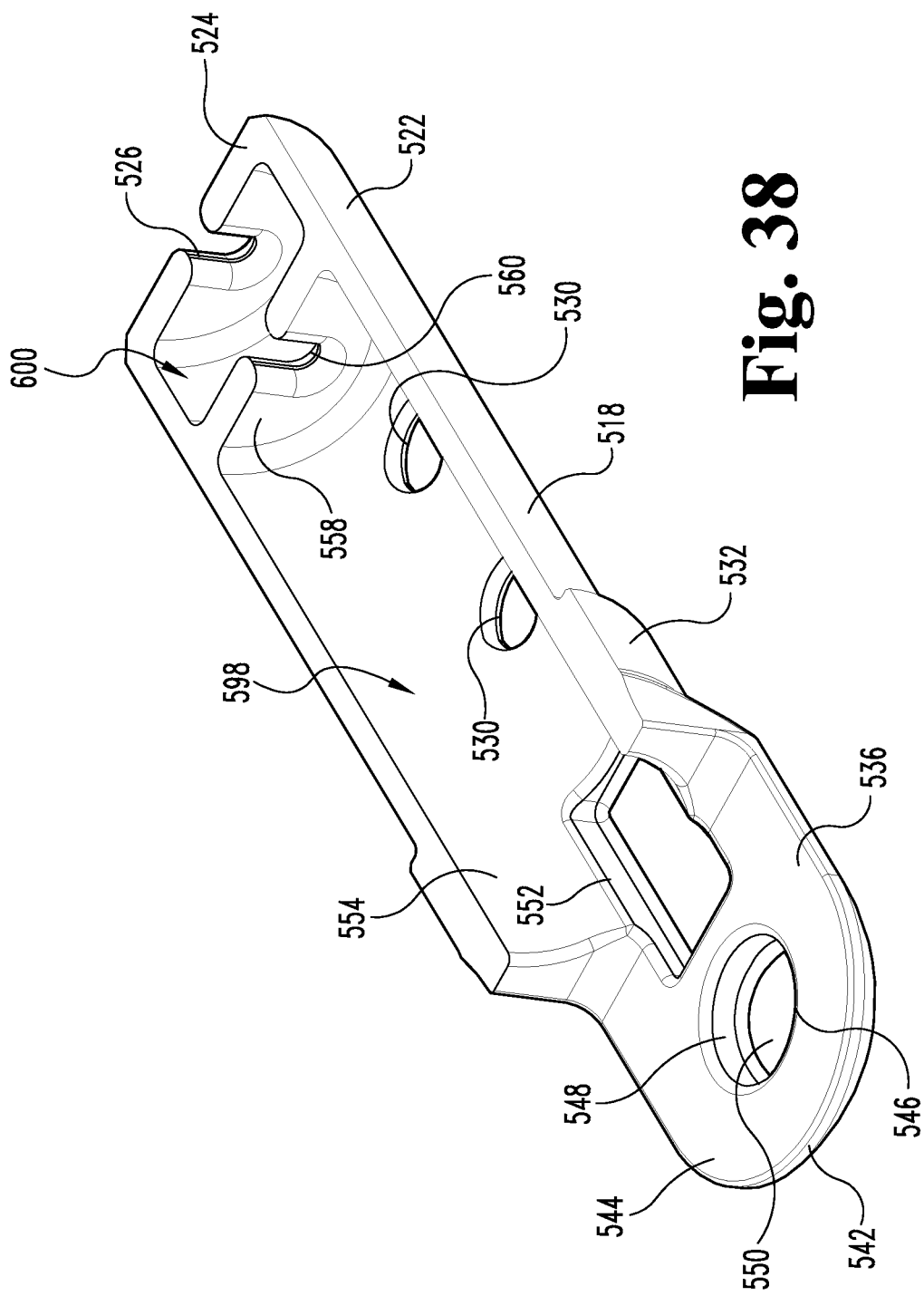
FIG. 38 is an elevated perspective view of a bottom housing of the exemplary clevis of FIG. 35.
Figure 39:
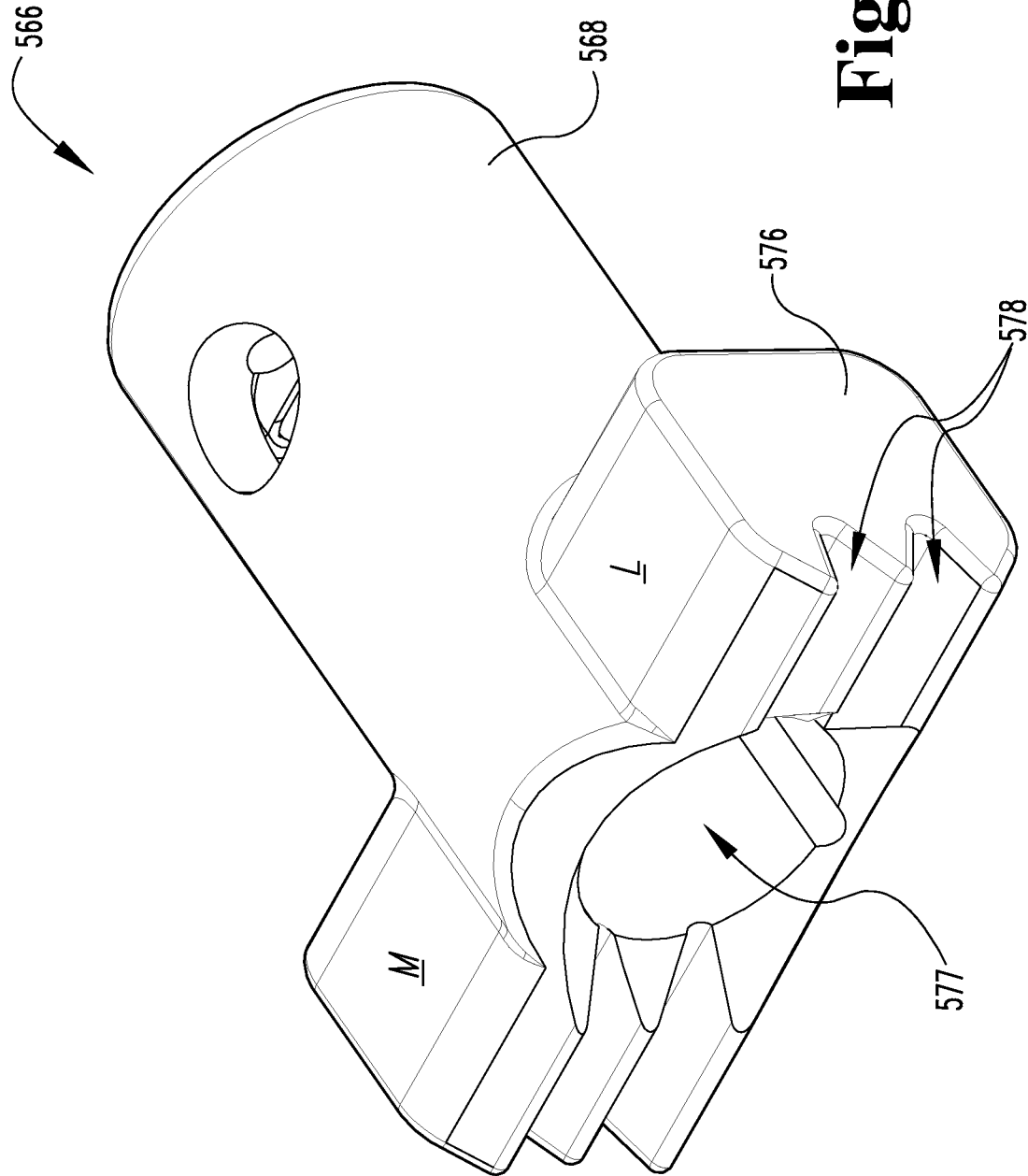
FIG. 39 is an elevated perspective view of an exemplary tooth receiver of the exemplary laparoscopic device of FIG. 1.
Figure 40:
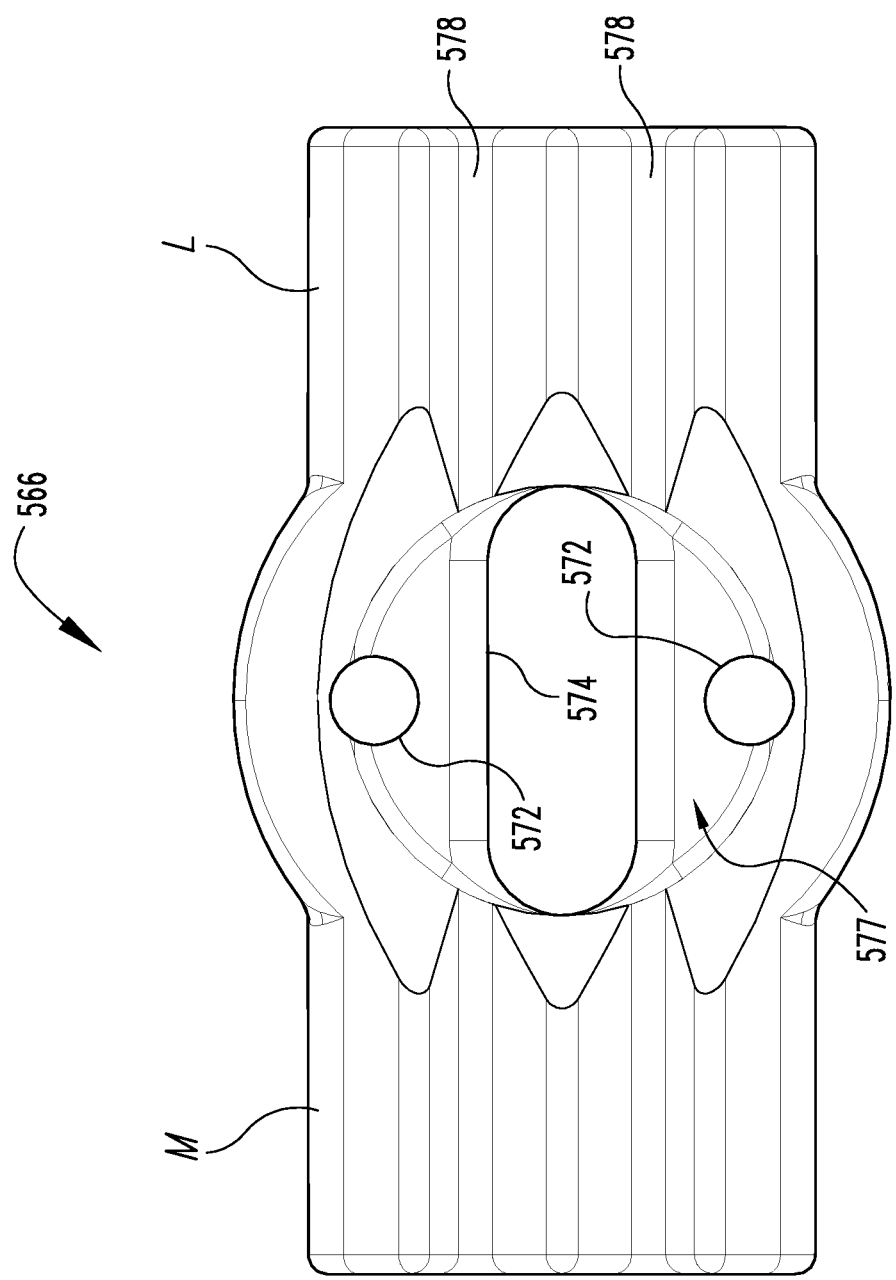
FIG. 40 is a front, profile view of the exemplary tooth receiver of FIG. 39.
Figure 41:
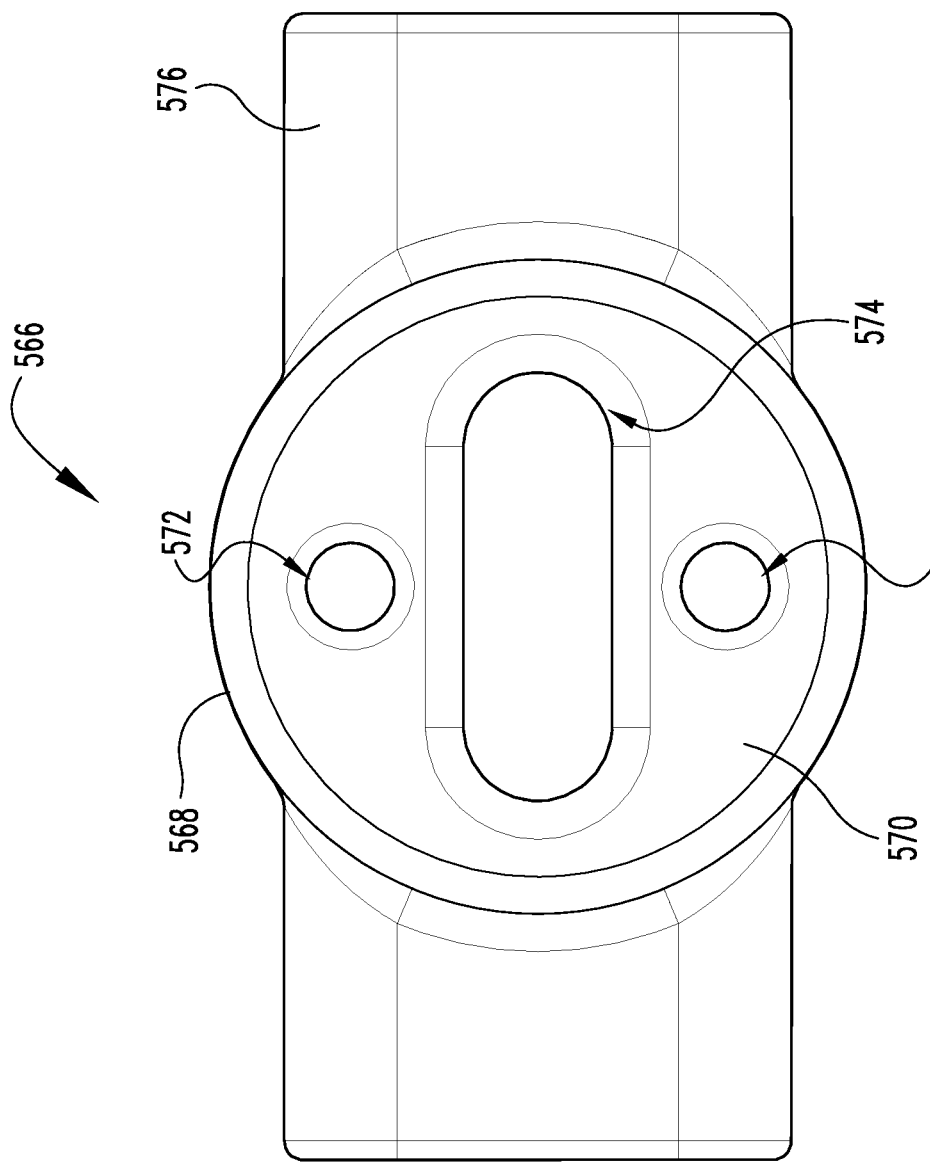
FIG. 41 is a rear, profile view of the exemplary tooth receiver of FIG. 39.

Referencing back to FIGS. 35-37, assembling the clevis 514 includes inserting the proximal cylindrical portion 568 of the tooth receiver 566 into the cylindrical cavity outlined by the spiral shape of the bias spring 564. Assembling the clevis 514 also includes aligning the ventral and dorsal clevis housings 516, 518 so that the edges where the exterior and interior surfaces meet match up and overlie each other. The edges may be welded or adhered together using conventional techniques. The resulting structure from assembly of the housings 516, 518 creates a distal cylindrical cavity 598 and a proximal cylindrical cavity 600 that are interposed by a circular wall having a through opening. As discussed previously, the circular wall is formed by joining the distal ribs 558 of the housings 516, 518, while the opening is formed by joining the notches 560. The distal cylindrical cavity 598 is sized to accommodate the tooth receiver 566 inserted into the bias spring 564 so that the end of the bias spring opposite the tooth receiver contacts the circular wall to provide a stop against which the spring may be compressed. At the same time, distal end 524 is closed off except for an opening formed by the adjoined notches 526. As mentioned above, the connection wire 261 is operatively coupled to the lever 236. This wire 261 also extends through the semi-rigid conduit 112 and through the openings until reaching the toothed receiver 566, where the wire is mounted to the toothed receiver in order to facilitate repositioning of the toothed receiver.

Referring to FIGS. 35-48, the clevis 514 is coupled to a universal joint 610. This universal joint 610 comprises a first pelvis half 594 coupled to a second pelvis half 596. In order to provide lateral repositioning, the pelvis halves 594, 596 are coupled to the clevis 514. In particular, the pelvis halves 594, 596 are identical to one another and, as such, a detailed explanation of only one of the pelvis halves is provided in furtherance of brevity.

Each pelvis half 594, 596 includes a distal paddle 624 having a substantially planar interior surface 626 that circles an upstanding rim 628. An opening 630 extends through the rim 628 and through the paddle 624, but is partially covered by an exterior convex cap 634 that is integrally formed with the paddle. The cap 634 includes a V-shaped groove 636 that extends into the opening 630 on one side, and a channel 638 that extends into the opening from the opposite side. The channel 638 extends proximally beyond the cap 634 and takes on an arcuate path to partially wrap around a proximal end 640 of the pelvis half and ends proximate an integrated platform 642 having a circular profile. A semi-circular interior surface 646 of the platform 642 is substantially planar and includes a radial groove 648 with arcuate sidewalls and a rounded end that extends to the center of the platform. The arcuate sidewalls operate to increase the width of the groove 648 as the distance from the interior surface 646 increases. The radial groove 648 also extends outward through a circular circumferential surface 650. The circumferential surface 650 defines the outer bounds of a ring-shaped, planar outer surface 652 that circumscribes an upstanding projection 656. It is this upstanding projection 656 that extends through the opening 586 of a corresponding toothed plate 582 to mount the tooted plate to the yoke half 620 (see FIG. 42). In exemplary form, the upstanding projection 656 extends perpendicularly away from the ring-shaped surface 652 and includes a pair of parallel straight sides 658 that are interposed by a pair of arcuate sides 660 that collectively define a plateau top 662.

In exemplary form, the distal paddle 624 includes a circular 664 circumferential surface connecting to a neck 666 in order to connect the distal paddle 624 to the integrated platform 642. The neck 666 also includes an arcuate wall 668 adapted to match the contour of the circular circumferential surface 650 of an opposing pelvis half 594, 596. The neck 666 further includes a centered block 672 having a planar surface 674 in parallel with the interior surface 646 of the platform 642. This planar surface 674 is partially has a raised peninsula 678 having arcuate sidewalls and an exposed rounded end. The arcuate sidewalls operate to decrease the width of the peninsula 678 as the distance from the planar surface 674 increases. As will be discussed in more detail hereafter, the dimensions of the peninsula 678 are generally the same as the dimensions of the radial groove 648 so that a peninsula of a first pelvis half 594, 596 is received within a radial groove of a second pelvis half in order to align the pelvis halves when assembled. The block 672 also includes a portion of the channel 638 on one side, while it also includes a channel 682 having a semicircular cross section and extending substantially in a straight line, except for a proximal slope. The channel 682 is generally centered and extends radially toward the interior surface 626 of the distal paddle 624. In exemplary form, the linear channel 682 interposes the peninsula 678 and the radial groove 648, which are generally parallel to one another and in a horizontally offset position.

Referring back to FIGS. 42, 43, and 45-48, assembly of the universal joint 610 includes orienting the pelvis halves 594, 596 so that the interior surfaces 626 of the paddles 624 face one another. Likewise, the necks 666 of the pelvis halves 594, 596 are oriented adjacent one another so that the peninsula 678 of the first pelvis half 594 is received within the radial groove 648 of the second pelvis half 596 so the interior surface 646 of the platform 642 of the second pelvis half contacts the planar surface of the first pelvis half. In this orientation, the pelvis halves 594, 596 are moved against one another (see FIG. 46) to define a circumferentially bounded through opening 688. After the pelvis halves 594, 596 have been mounted to one another in the foregoing orientation, respective toothed plates 582 are mounted to each of the pelvis halves. In exemplary form, the each toothed plate 582 is oriented so that the opening 586 is aligned with the upstanding projection 656. Specifically, the parallel sides 658 of the upstanding projection 656 are aligned and inset with respect to the parallel sides 588 defining the opening 586, while the arcuate sides 660 of the upstanding projection are aligned and inset with respect to the arcuate ends 590 defining the opening. Thereafter, the ventral and dorsal clevis housings 516, 518 are repositioned to sandwich the pelvis halves 594, 596. Specifically, the circular depression 546 of each housing receives a respective upstanding projection 656 of a pelvis half 594, 596. The circular boundary of the depression 546 is slightly larger in diameter than the distance between the arcuate sides 660 of the projections, thereby allowing the projections to rotate within the depressions. It should be noted that the arc of the sides 660 is more pronounced than that of the wall 548 defining the projection, but no so much that considerably play is present. At the same time as the pelvis halves 594, 596 are sandwiched by the ventral and dorsal clevis housings, both toothed plates 582 are oriented so that at least one tooth 580 is received within a gap between the teeth 578 of the tooth receiver 566. When the teeth 580 of the toothed plates 582 engage the teeth 578 of the tooth receiver 566, rotational motion (angular changes in the horizontal plane) of the pelvis halves 594, 596 with respect to the ventral and dorsal clevis housings 516, 518 is inhibited. Conversely, when the teeth 580 of the toothed plates 582 are not engaged with the teeth 578 of the tooth receiver 566, the pelvis halves 594, 596 are able to rotate with respect to the ventral and dorsal clevis housings 516, 518. The default position of the tooth receiver 566 creates engagement between the respective teeth 578, 580 based upon the bias exerted upon the tooth receiver by the spring 564. But this bias may be overcome by pulling the tooth receiver 566 proximally using the connection wire 261 concurrently coupled to the tooth receiver and the repositionable lever 236. In particular, to lock the angular position of the pelvis halves 594, 596 with respect to the ventral and dorsal clevis housings 516, 518, the lever 236 is rotated distally to allow the bias of the spring 564 to push the tooth receiver 566 into engagement with the toothed plates 582. To unlock the pelvis halves 594, 596 with respect to the ventral and dorsal clevis housings 516, 518, the lever 236 is rotated proximally to overcome the bias of the spring 564, thereby compressing the spring and pulling the tooth receiver 566 out of engagement with the toothed plates 582. When this occurs, the pelvis halves 594, 596 as a whole are able to change their angular, horizontal orientation with respect to the ventral and dorsal clevis housings 516, 518 and have a range of angular adjustment of 160 degrees. This angular adjustment and corresponding angular orientation are carried over from the pelvis halves 594, 596 to a yoke 614.

In exemplary form, the clevis 514 (housings 516, 518, spring 564, and tooth receiver 566), the toothed plates 582, and the pelvis halves 594, 596 cooperate to form the distal part of the passive mechanism. This passive mechanism allows or inhibits yaw (i.e., side to side) of the end effector 118 depending upon whether the tooth receiver 566 is distally biased by the spring 564 into engagement with the toothed plates 582. Because the tooth receiver 566 is either engaged or disengaged with respect to the toothed plates 582, the mechanism is considered passive. In other words, unlike the active mechanism previously discussed, this passive mechanism does not operate to reposition the end effector side to side. Rather, this passive mechanism provide full freedom to move laterally within the range of motion between the clevis 514 and pelvis halves 594, 596 when the tooth receiver 566 is not engaging the toothed plates 582. In exemplary form, it is anticipated that a robotic instrument (not shown) or an anatomical feature (i.e., the heart itself) in cooperation with pressure applied to the distal end of the semi-rigid conduit 112 would reposition the end effector laterally (such as shown in exemplary form by the three positions depicted in FIG. 17B) once the controller 110 is manipulated (specifically, the lever 236) to disengage the tooth receiver 566 from the toothed plates 582. As long as the tooth receiver 566 is disengaged from the toothed plates 582, the end effector 118 may be repositioned (i.e., is not laterally locked in place). But when the lever 236 is actuated so that the spring 564 force is dominant and the tooth receiver 566 engages the toothed plates 582, lateral repositioning of the end effector 118 is inhibited.

Referring to FIGS. 49-52, the yoke 614 comprises a cylindrical proximal end 690 integrally coupled to a floor 692 and a roof 694 that are identically shaped. More specifically, as will be discussed in more detail hereafter, the cylindrical proximal end 690 includes a through cavity 696 that extends into an open space 698 between the floor 692 and a roof 694 in order to accommodate certain parts of the repositionable mechanism 116.

In exemplary form, the cylindrical proximal end 690 includes a circumferential groove 702 operative to bisect the cylindrical proximal end into a pair of discs 704. Each disc 704 is a mirror image of the other and includes a rounded circumferential surface 706 having a generally constant width and defining the outer bounds of a substantially planar lateral surface 708 that is generally perpendicular with respect to the circumferential surface. This lateral surface 708 is generally ring-shaped to define a cylindrical depression 710 that does not extend entirely through the disc 704 and is equidistantly spaced with respect to the edge of the circumferential surface 706. In exemplary form, the cylindrical depression 710 is defined by a top beveled ring 714, followed by a constant diameter ring 716, followed by a second beveled ring 718 that adjoins a substantially planar bottom surface 720 in parallel with the lateral surface 708.

The circumferential groove 702 between the discs 704 extends in a semicircular path and intersects a through hole 722 extending through the floor 692 and roof 694. Opposite the through hole 722, at the proximal end of the groove 702, a V-shaped opening is formed that is part of the through cavity 696, where the distal tip of the opening is defined by a rectangular boundary 724, which is adjacent to a circular wall 726 that defines a cylindrical portion of the through cavity. Ventral and dorsal sections of the groove 702 receive a respective connection wire 194, where each connection wire is threaded within a portion of the groove so that pulling on a first of the connection wires causes the yoke 614 to move upward (i.e., ventrally), while pulling on the second of the connection wires causes the yoke to move downward (i.e., dorsally). More specifically, the connection wires 194 are partially looped around the yoke 614 by lying within a portion of the groove 702 and terminate in a cavity where the connection wire 194 is secured in place.

Extending distally from the discs 704 are the roof 694 and floor 692. Both the roof 694 and floor 692 comprise a rounded overhang having a relatively planar exterior surface 732 that transitions into a sloped circumferential surface 734, that itself transitions into a vertical circumferential surface 736 that is perpendicular to the exterior surface. It should be noted that the vertical thickness of the roof 694 is greater than that of the floor 692, but other than this thickness difference the roof and floor are identical. The vertical circumferential surface 736 defines the outer boundary for the multi-tiered interior surface 738. In particular, the interior surface 738 is partially defined by a raised plateau 740 having a relatively planar end surface 742 adjoining a relatively planar vertical sidewall 744 that is offset from a midline of the yoke 614. Adjoining the sidewall 744 is a relatively planar horizontal wall 746, which is itself adjoined by a block U-shaped groove 748. The plateau 740, sidewall 744, horizontal wall 746, and U-shaped groove 748 cooperate to create a stair-step cross-section. But the U-shaped groove does not extend distally as far as the sidewall 744 and the horizontal wall 746 because the U-shaped groove terminates in a proximal wall 752 that is distal to the ends of the sidewall and horizontal wall that terminate at a back wall 754. Proximate the back wall 754, both the roof 694 and floor 692 include a pair of vertical through openings that are aligned with their counterpart through openings and receive a pair of dowels 758. As discussed in more detail hereafter, the dowels are concurrently mounted to the roof 694 and floor 692, as well as to a repositionable jaw assembly 760.

Referencing FIGS. 49, 50, and 52-54, the repositionable jaw assembly 760 includes a pull link 764 operatively coupled to the connection wire 194 at its proximal end and concurrently coupled to right and left link plates 766, 768 at its distal end. In this exemplary embodiment, the pull link 764 comprises a hollow cylinder 770 mounted to a miniature clevis 772. In particular, the hollow cylinder 770 is mounted to extend perpendicularly away from the base of the clevis 772 and is adapted to receive the connection wire 194 therein. More specifically, the connection wire 194 is glued to the interior of the hollow cylinder 770 so that tensioning of the connection wire in the proximal direction is operative to reposition the pull link 764 proximally. This proximal repositioning is also operative to reposition the ends of the link plates 766, 768 mounted to the clevis 772. In exemplary form, the clevis 772 includes a pair of spaced apart, upstanding arms 774 having a generally constant width and height along their longitudinal length. Each upstanding arm 774 terminates at a hollow ring 776 having a height generally the same as that of the upstanding arms, but a width that is greater than the upstanding arms. The width of both rings 776 is generally the same and is sized to fit between respective vertical walls 744 of the floor 692 and roof 694 in order to ensure that motion of the clevis 772 with respect to the yoke 614 is linear.

Figure 55:
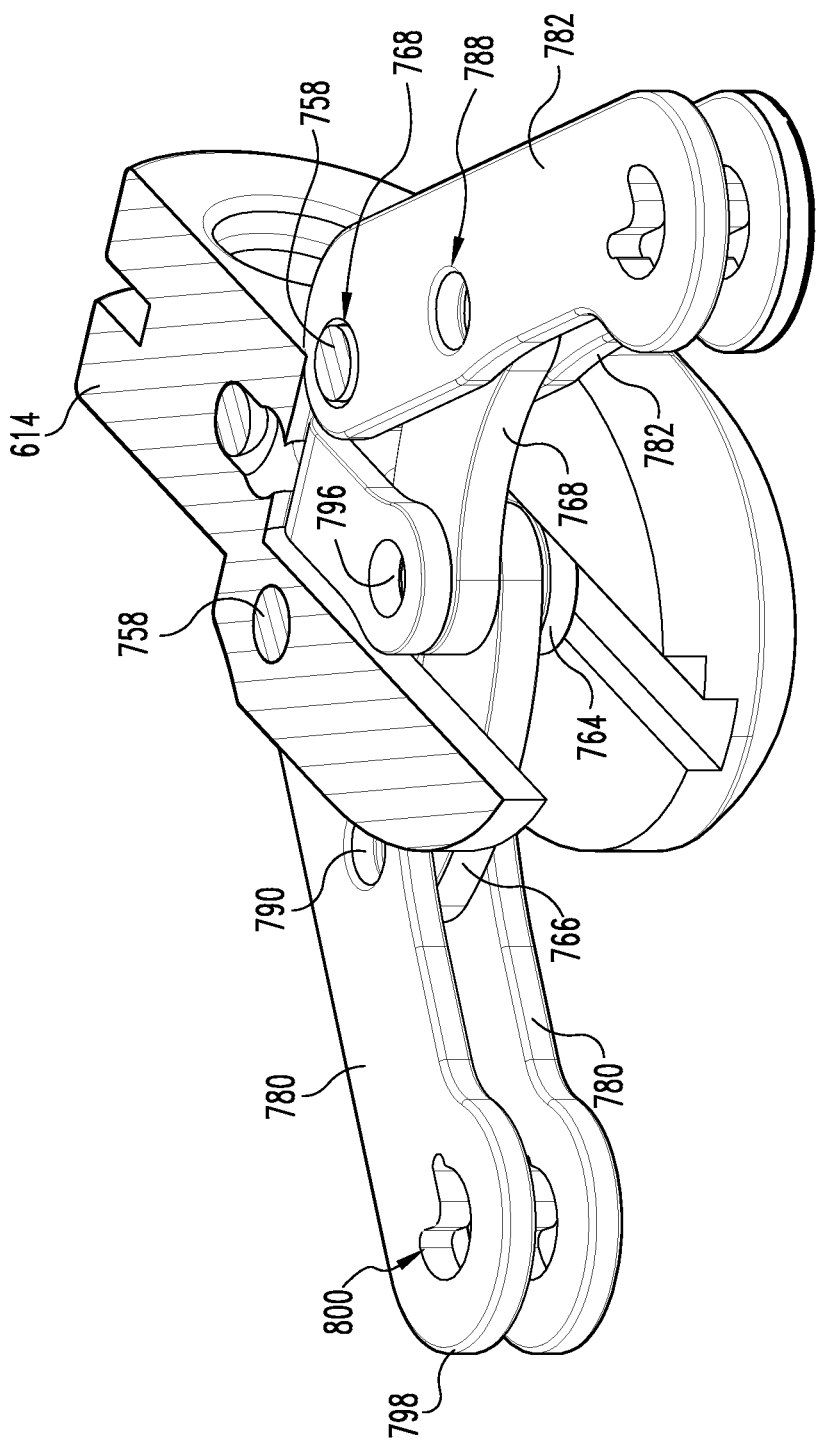
FIG. 55 is a horizontal cross-sectional view of the exemplary yoke and pull link coupled to exemplary link plates and link clips.
Figure 56:
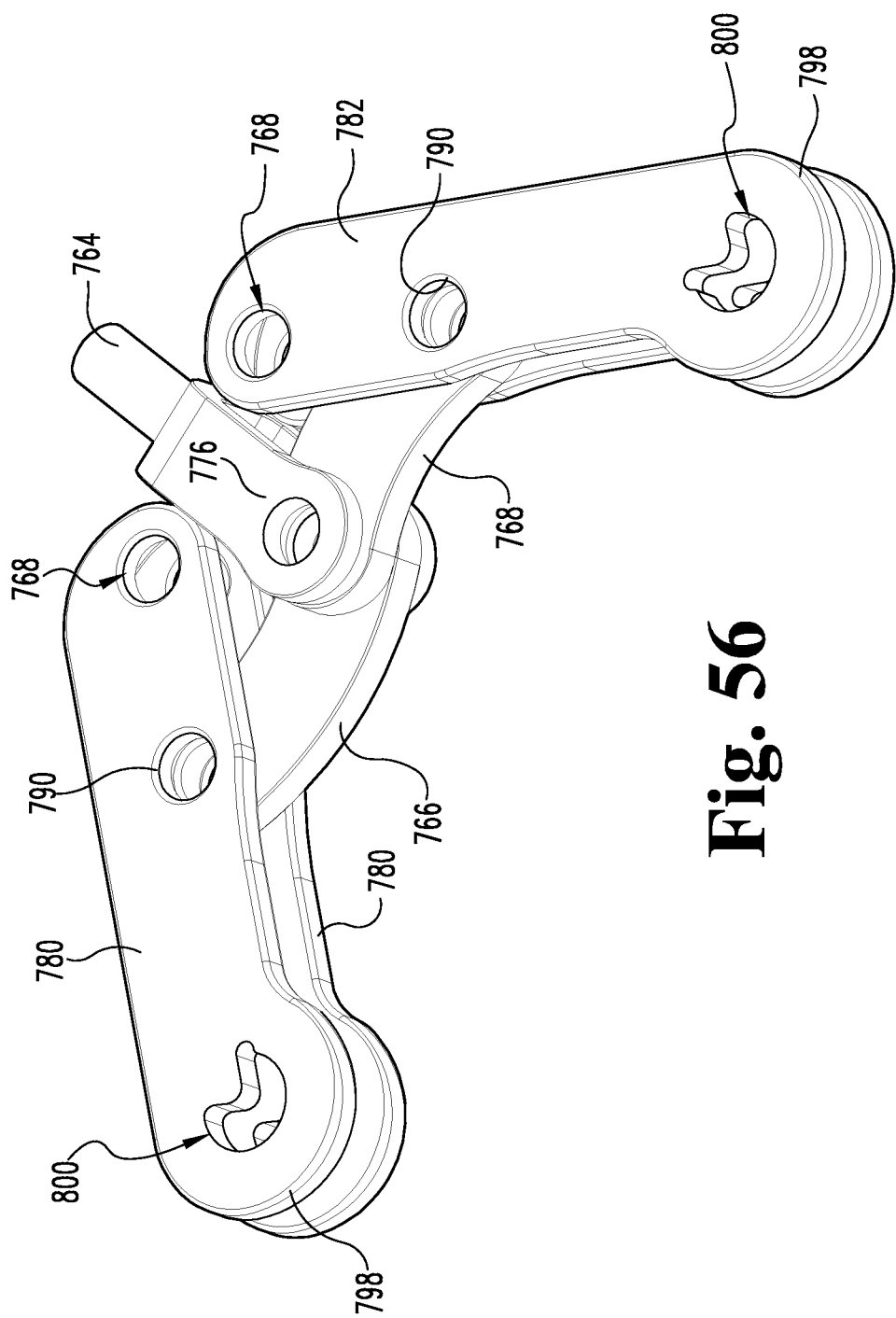
FIG. 56 is an elevated perspective view of the exemplary pull link coupled to exemplary link plates and link clips.
Figure 57:
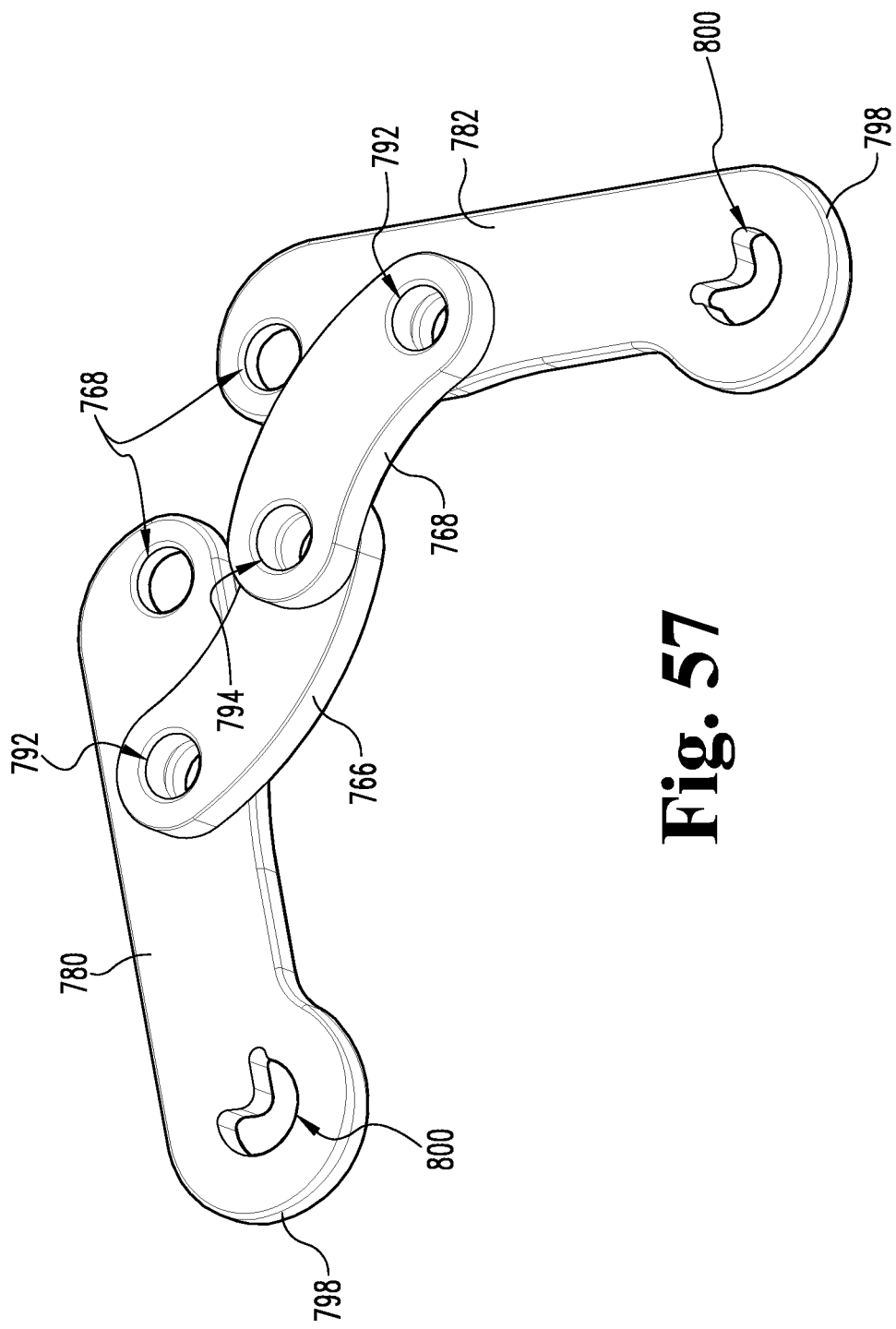
FIG. 57 is an elevated perspective view of the exemplary link plates coupled to the exemplary link clips of FIG. 56.

Referring to FIGS. 55-57, the yoke 614 also has mounted to it a pair of right and left link clips 780, 782 that are concurrently mounted to the link plates 766, 768. In exemplary from, the right and left link clips 780, 782 are mirror images of one another and each include a proximal through hole 786 that receives a dowel 758 of the yoke 614 to pivotally mount the right and left link clips to the yoke. At the same time, the right and left link clips 780, 782 include a second through hole 788, distal to the proximal hole 786, that receives a dowel 790 that is currently received through an opening 792 at the ends of the link plates 766, 768. The openings 792 at the ends of the link plates 766, 768 are larger in diameter than the diameter of the dowel 790, so that the link plates are pivotally repositionable around the dowel. Conversely, the second through hole 788 has generally the same diameter as the diameter of the dowel 790, thereby securing the dowel within the second through hole via a friction fit. Opposite the ends of the of the link plates 766, 768 is an internal through hole 794 having a diameter larger than a dowel 796 that is frictionally received within the rings 776 of the clevis 772. In this manner, the link plates 766, 768 are pivotally repositionable with respect to the dowel 796 and clevis 772. At a distal end of each right and left link clip 780, 782 is a rounded, flat head 798 that circumscribes a distal opening 800 having a three-quarter moon shape. In particular, the distal head 798 is sized so that the width of the head is greater than the width of the remainder of the link clips 780, 782. More specifically, the distal head 798 is rounded to extend toward the interior of the repositionable jaw assembly 760. As will be discussed in more detail hereafter, the rounded profile of the distal head matches a cylindrical profile of a corresponding jaw 806, 808.

When assembled, the hollowed rings 776 of the clevis 772 are interposed by the ends of the link plates 766, 768. The opposite ends of the link plates 766, 768 interpose respective right and left link clips 780, 782. Accordingly, the left link clips 782 directly overly one another and are spaced apart from one another by the thickness of the left link plate 768 and an associated gap operative to provide movement between the left link plate and the left link clips. Likewise, the right link clips 780 directly overly one another and are spaced apart from one another by the thickness of the right link plate 766 and an associated gap operative to provide movement between the right link plate and the right link clips. At the same time, the distance between the roof 694 and floor 692, proximate the plateau 740 on the right side is slightly larger than the cumulative thicknesses of the right link clips 780 and right link plate 766. Similarly, the distance between the roof 694 and floor 692, proximate the plateau 740 on the left side is slightly larger than the cumulative thicknesses of the left link clips 782 and left link plate 768. Upon assembly, the link plates 766, 768 are rotationally repositionable with respect to the clevis 772 and the right and left link clips 780, 782, while the right and left link clips are rotationally repositionable with respect to the link plates and with respect to the dowels 758 of the yoke 614. As will be discussed in more detail hereafter, retraction of the clevis 772 proximally (see FIG. 49) within the yoke 614 is operative to widen the gap between the rounded ends 798 of the right and left link clips 780, 782. Conversely, repositioning the clevis 772 distally with respect to the yoke 614 is operative to decrease the gap between the rounded ends 798 of the right and left link clips 780, 782. In this manner, the repositioning of the clevis 772 is indirectly operative to reposition the right and left jaws 806, 808.

Figure 49:
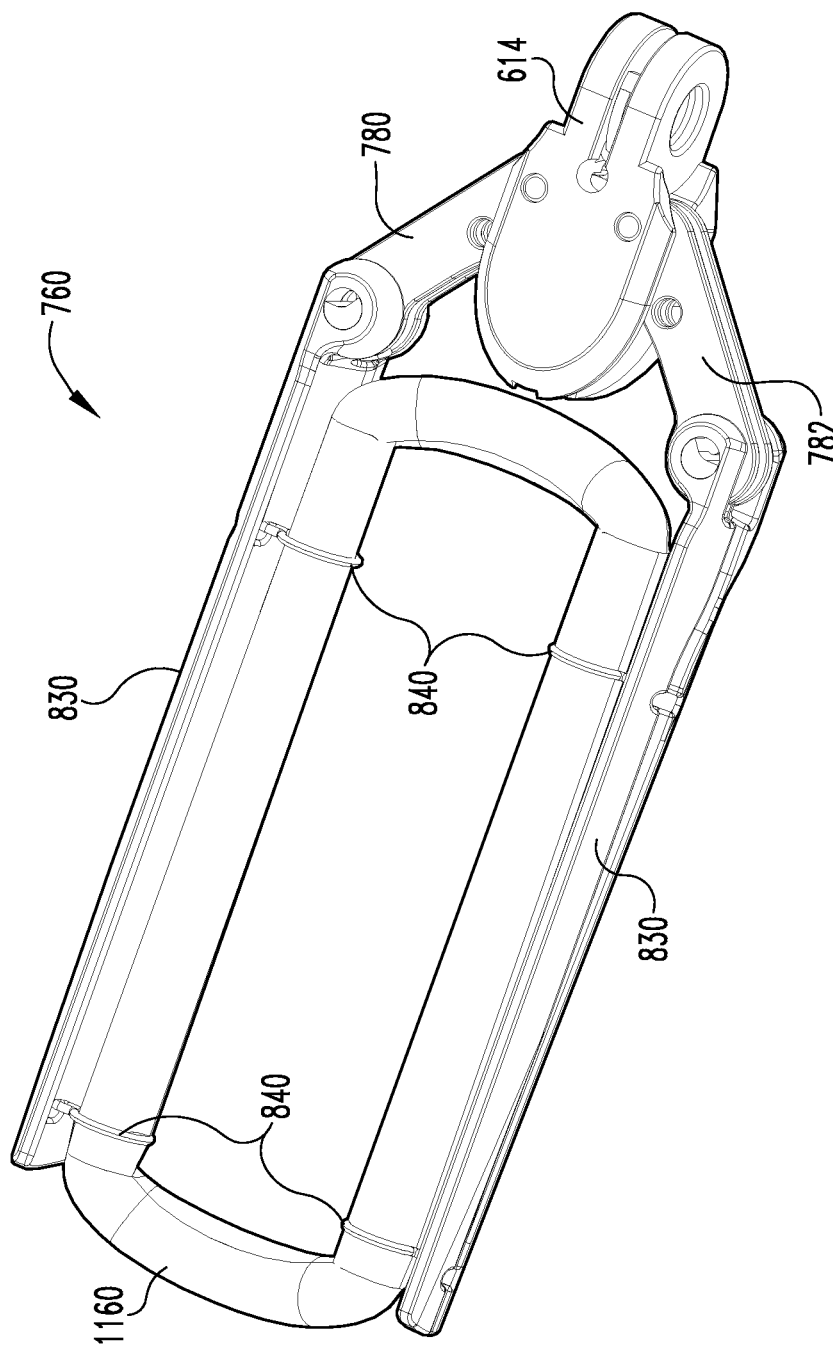
FIG. 49 is an elevated perspective view of an exemplary repositionable jaw assembly of the exemplary laparoscopic device of FIG. 1.
Figure 50:
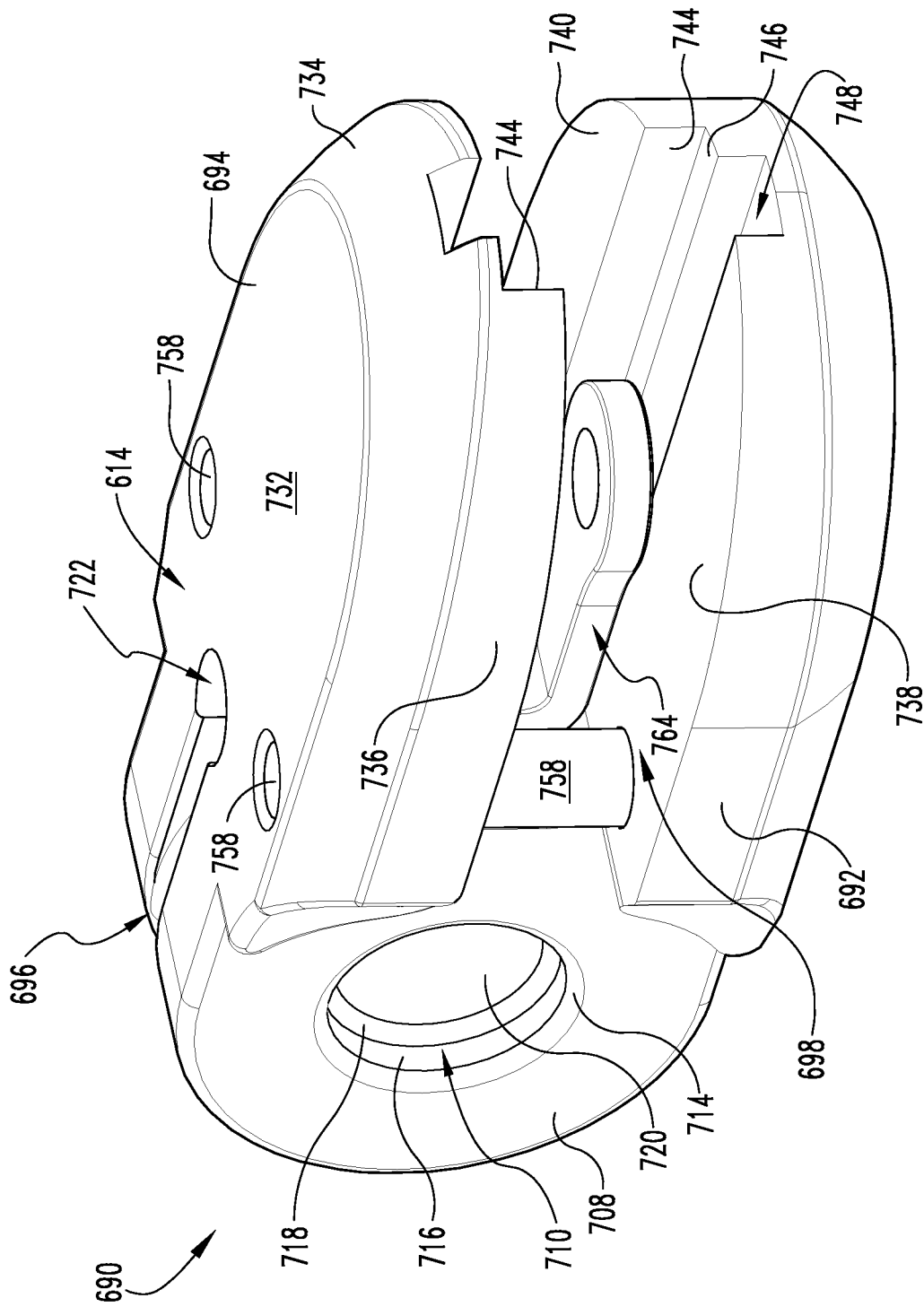
FIG. 50 is an elevated perspective view of an exemplary yoke and pull link of the exemplary laparoscopic device of FIG. 1.
Figure 51:
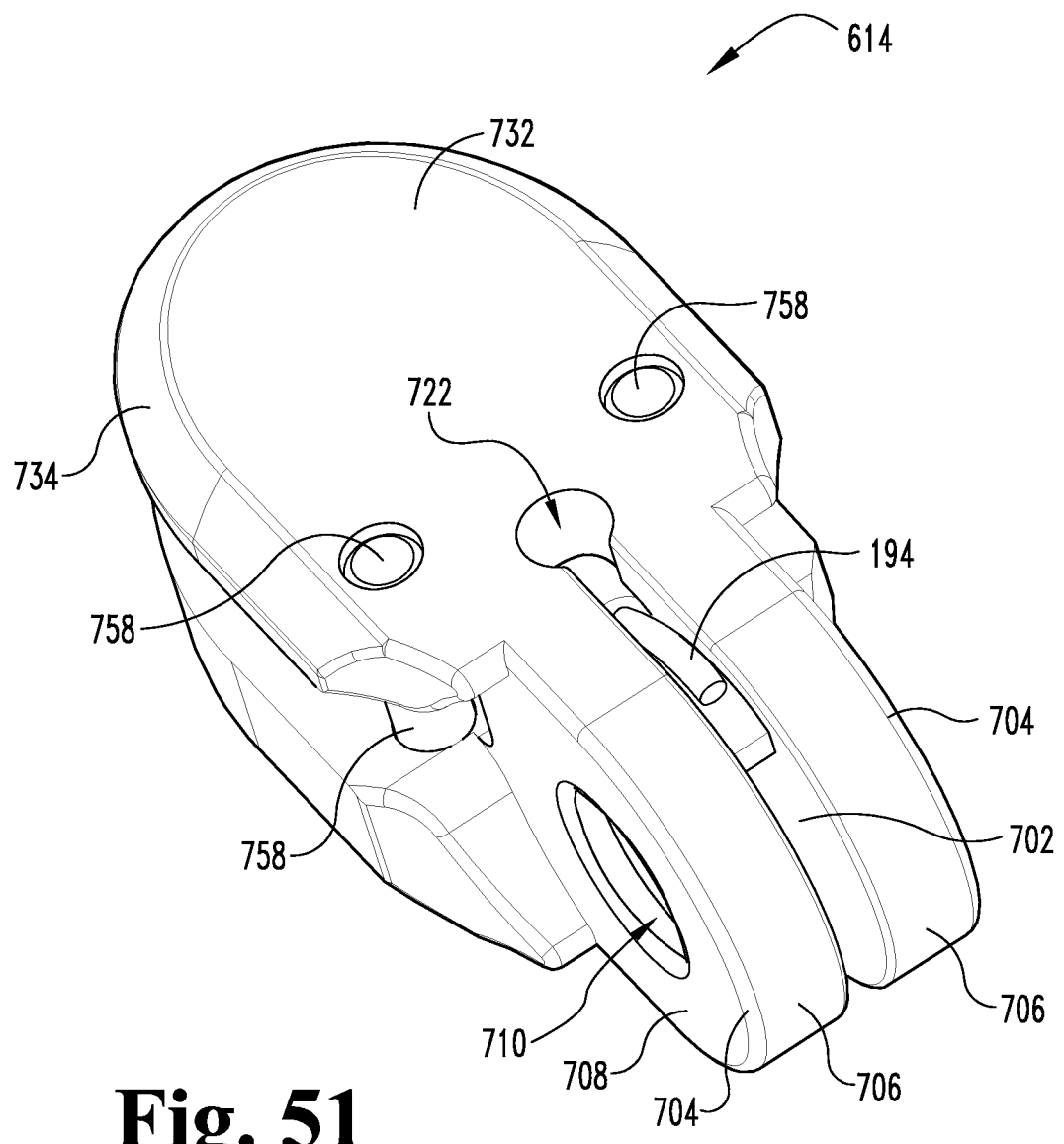
FIG. 51 is an elevated perspective view from the proximal end of the exemplary yoke of FIG. 50.
Figure 52:
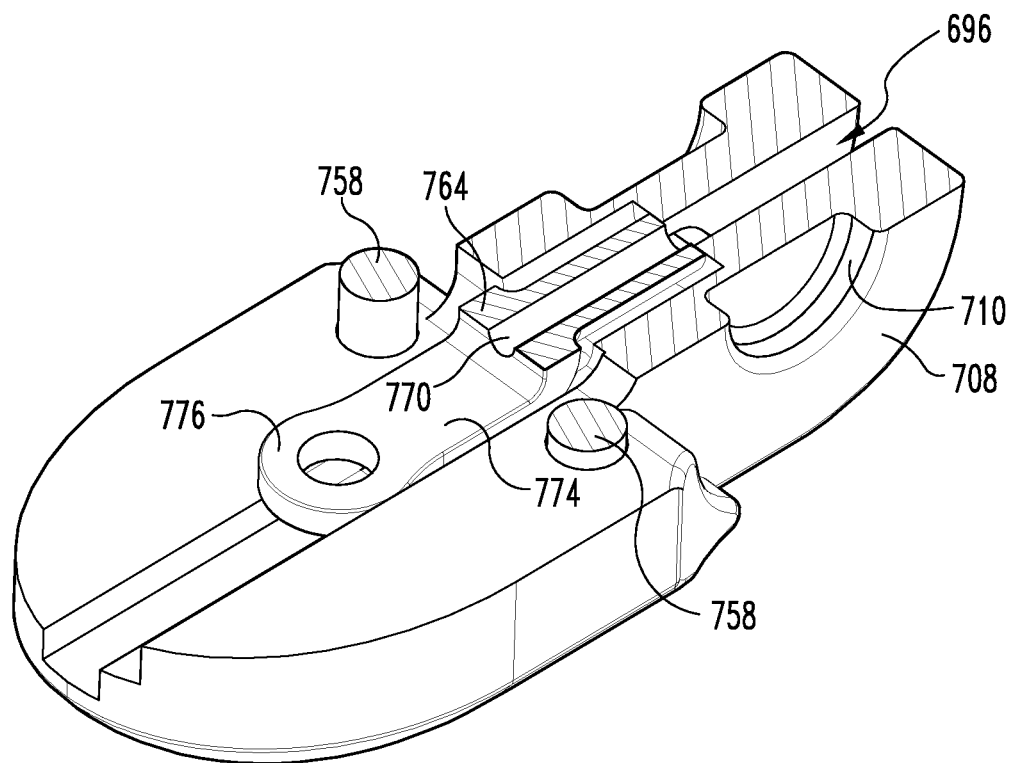
FIG. 52 is a horizontal cross-sectional view of the exemplary yoke and pull link of FIG. 50.
Figure 53:
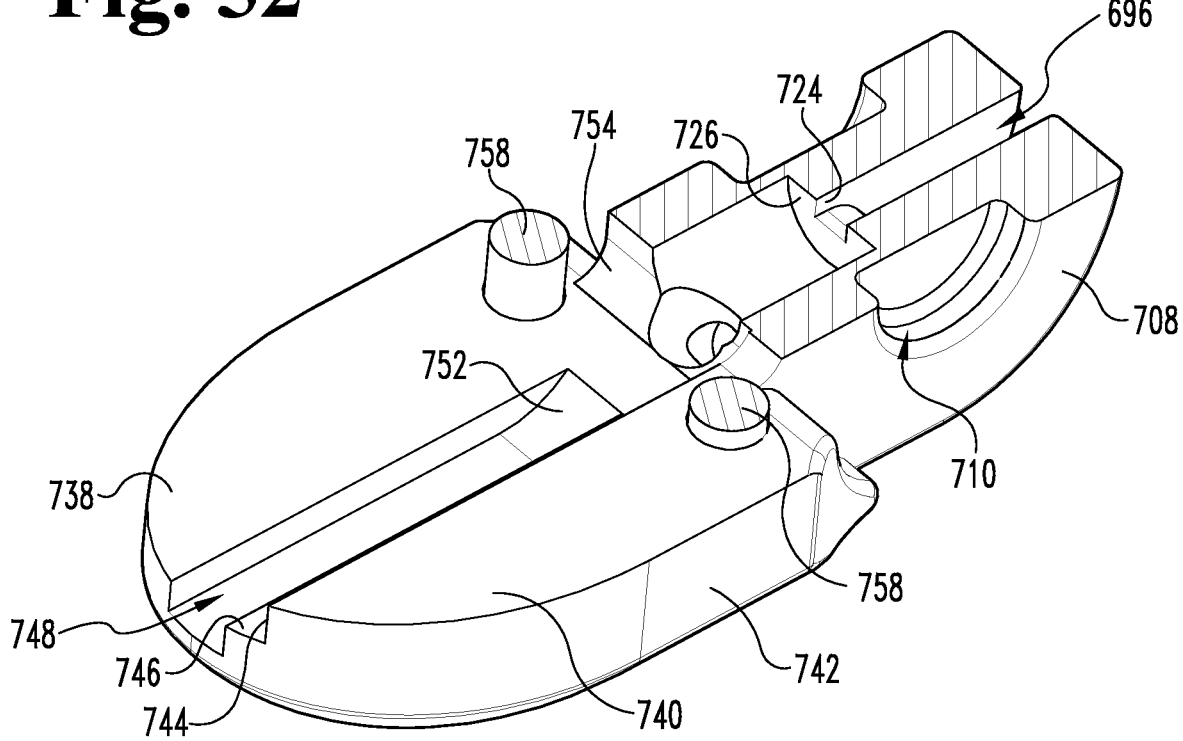
FIG. 53 is a horizontal cross-sectional view of the exemplary yoke of FIG. 50.
Figure 54:
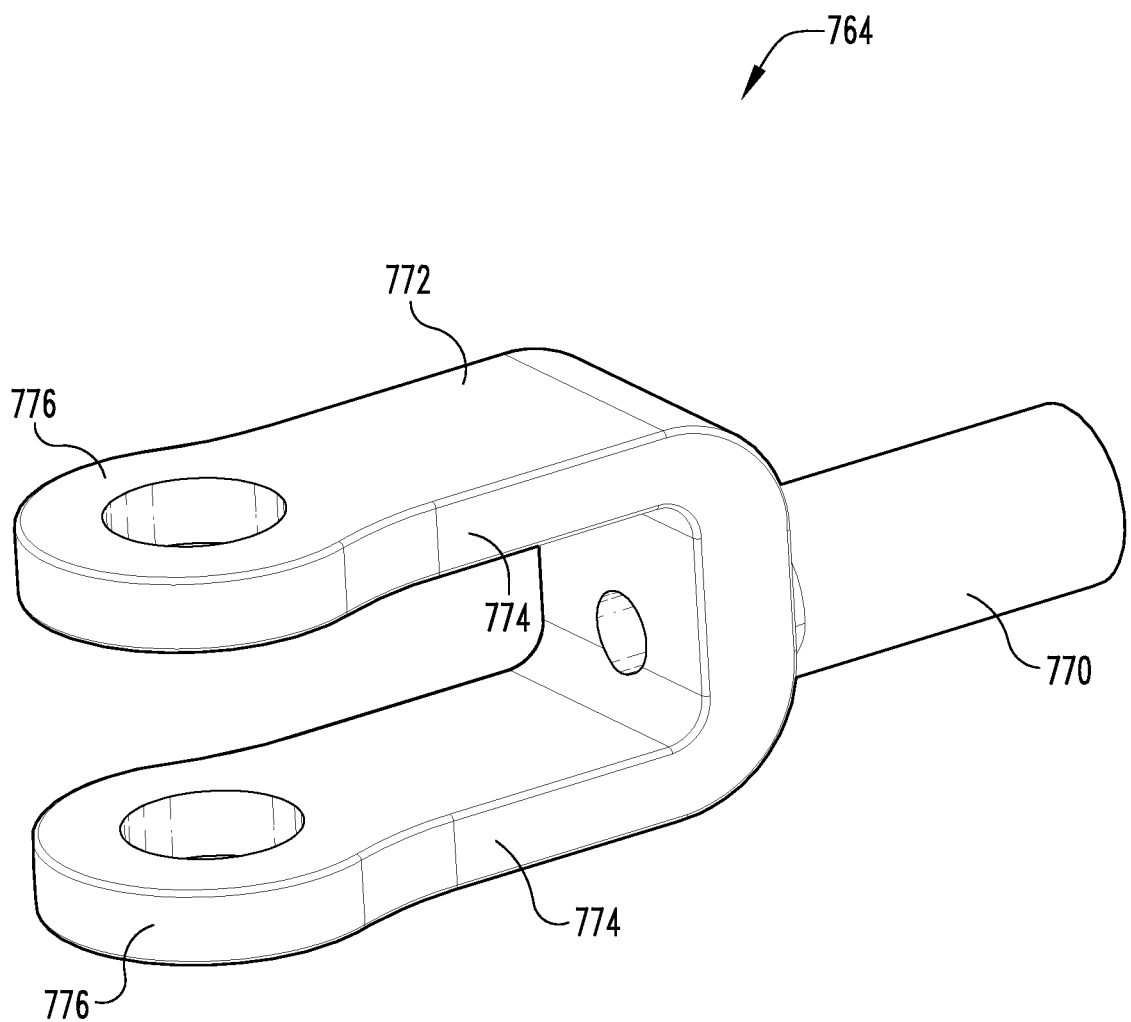
FIG. 54 is an elevated perspective view of the pull link of FIG. 50.

Referencing FIGS. 49, 58, and 59, the right and left jaws 806, 808 are mirror images of one another and are respectively mounted to the right and left link clips 780, 782. Accordingly, in furtherance of brevity, only the left side jaw will be shown and discussed with respect to FIGS. 58 and 59. Each jaw 806, 808 includes a proximal end clevis 810 that comprises a top rounded shelf 814 that is spaced apart from a bottom rounded shelf 816. Each shelf 812, 814 includes a through opening 818 operative to receive a half-moon shaped cylindrical dowel 820. This dowel 820, while being concurrently received within the through openings 818 of the shelves 812, 814, is also received within the distal opening 800 of a respective pair of the link clips 780, 782. In exemplary form, the dowel 820 is frictionally fit within the through openings 818 so that the dowel is not rotationally repositionable within the through opening. In contrast, the half-moon shape of the dowel 820 does not occupy all of the area of the three-quarter moon shape of the distal openings 800. In this manner, there is play between the walls defining the distal opening and the dowel 820 so that the dowel is rotationally repositionable with respect to the respective link clips 780, 782. In order to further stabilize the connection between the respective jaw 806, 808 and the respective link clips 780, 782, each jaw includes a projection 824 that extends proximally from a vertical wall 826 that connects the shelves 812, 814 at their respective distal ends. The thickness of this projection 824 approximates the gap between the respective overlying link clips 780, 782 in order to inhibit the distal ends 798 of the link clips from compressing against one another. Rather, because of the projection 824, compression is reduced and to the extent compression occurs, the overlying link clips 780, 782 compress against the projection instead of against one another.

Extending distally from the proximal end clevis 810 is an elongated guide 830 having a convex exterior longitudinal profile and a concave interior longitudinal profile. The elongated guide 830 has a dominant longitudinal dimension and a vertical dimension that approximates and extends beyond the thickness of a clamping portion 1162, 1164 (see FIG. 75). In exemplary form, the distal end 832 of the guide 830 is rounded. Interposing the distal end 832 and the proximal end clevis 810 is a pair of lateral through holes 836, 838 that receive sutures 840 in order to mount the jaw 806, 808 to a respective clamping portion 1162, 1164. An exterior side 844 of the guide 830 includes a longitudinal channel 846 that extends from the distal end 832, crossing each of the through holes 836, 838, proximally through the vertical wall 826 and ending adjacent the projection 824. This channel 846 receives a respective clip release wire 492 that is coupled to the removable stem 490 of the controller 110. In exemplary form, the suture 840 is concurrently wrapped around (in a loop) the clip release wire 492 and a respective Clip segment. In this manner, when the clip is ready to be deployed, the removable stem 490 is proximally repositioned with respect to the remainder of the controller 110, thereby pulling the clip release wires 492 proximally. Initially, the end of the clip release wires 492 passes completely through the distal suture 840, followed by passing completely through the proximal suture 840, thereby releasing the clip from the guides 830 and the remainder of the laparoscopic device 100.

Figure 60:
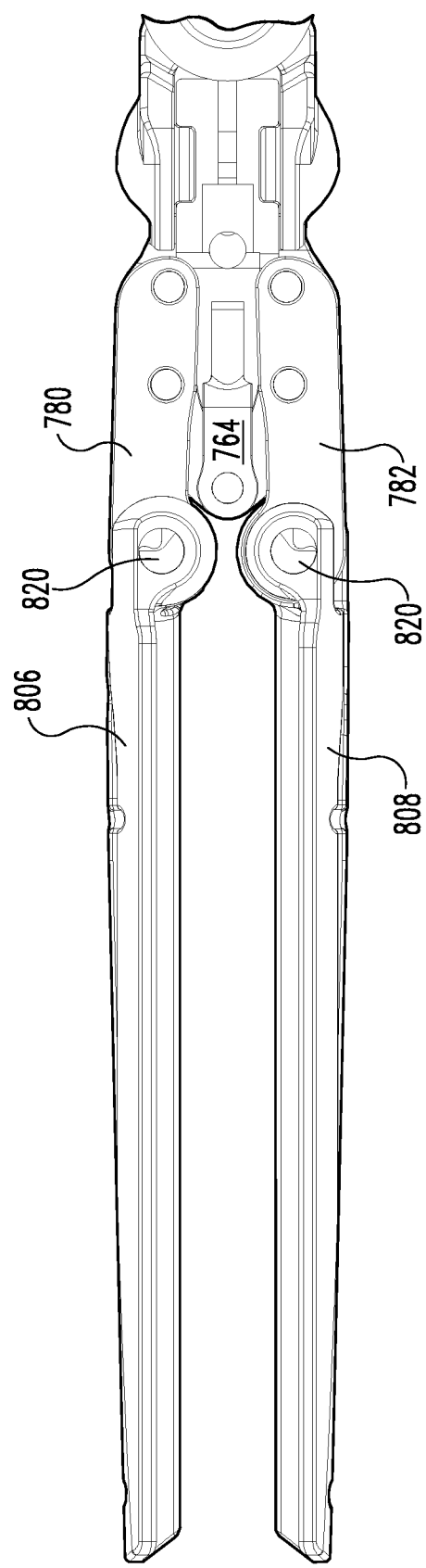
FIG. 60 is an overhead view showing the position of the jaws and various other distal end components of the exemplary laparoscopic device of FIG. 1 in a most compact widthwise orientation.
Figure 61:
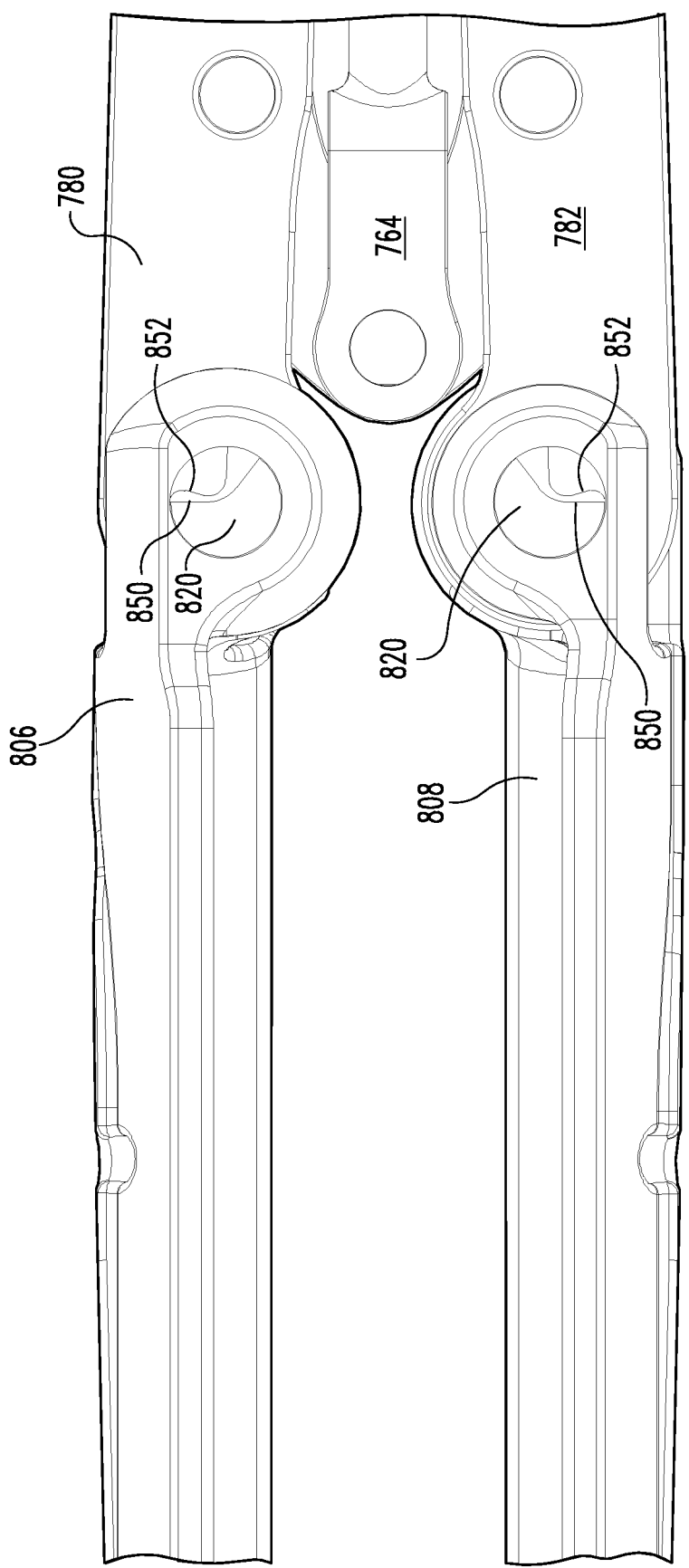
FIG. 61 is an overhead, magnified view of the jaws and link clips of FIG. 60.

Referring to FIGS. 44, 60, and 61, the repositionable jaw assembly 760 is operative to be linearly aligned to fit through a trocar for anatomical deployment. Initially, as shown in FIGS. 60 and 61, the repositionable jaw assembly 760 is linearly aligned and in a compact, widthwise position. In this position, a first face 850 of each dowel 820 of both jaws 806, 808 contacts a first face 852 defining a portion of the three-quarter shaped moon opening 800.

Figure 62:
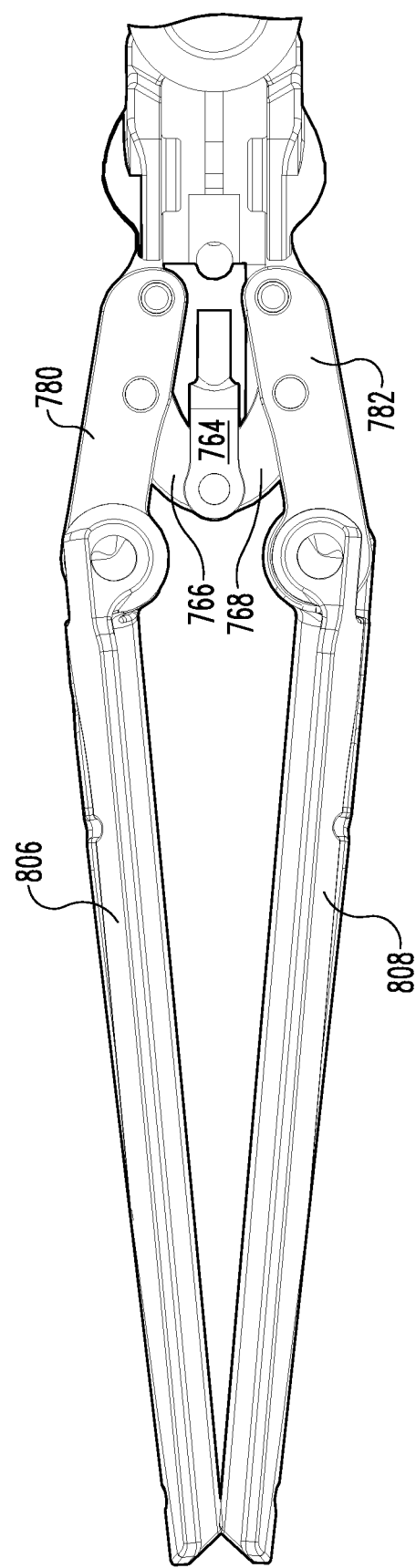
FIG. 62 is an overhead view showing the position of the jaws and various other distal end components of the exemplary laparoscopic device of FIG. 1 as the pull link is initially moved proximally.
Figure 63:
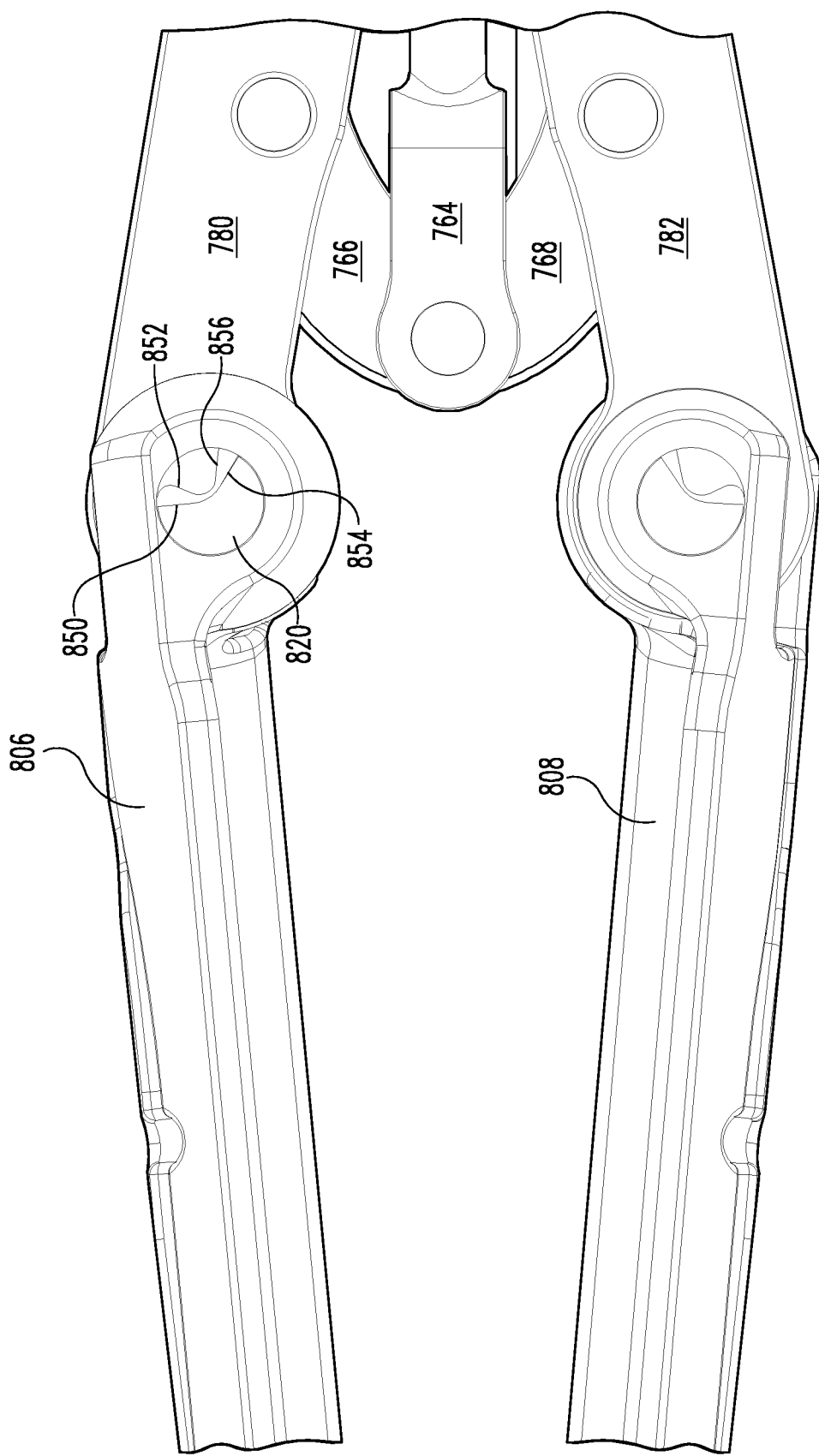
FIG. 63 is an overhead, magnified view of the jaws and link clips of FIG. 62.
Figure 64:
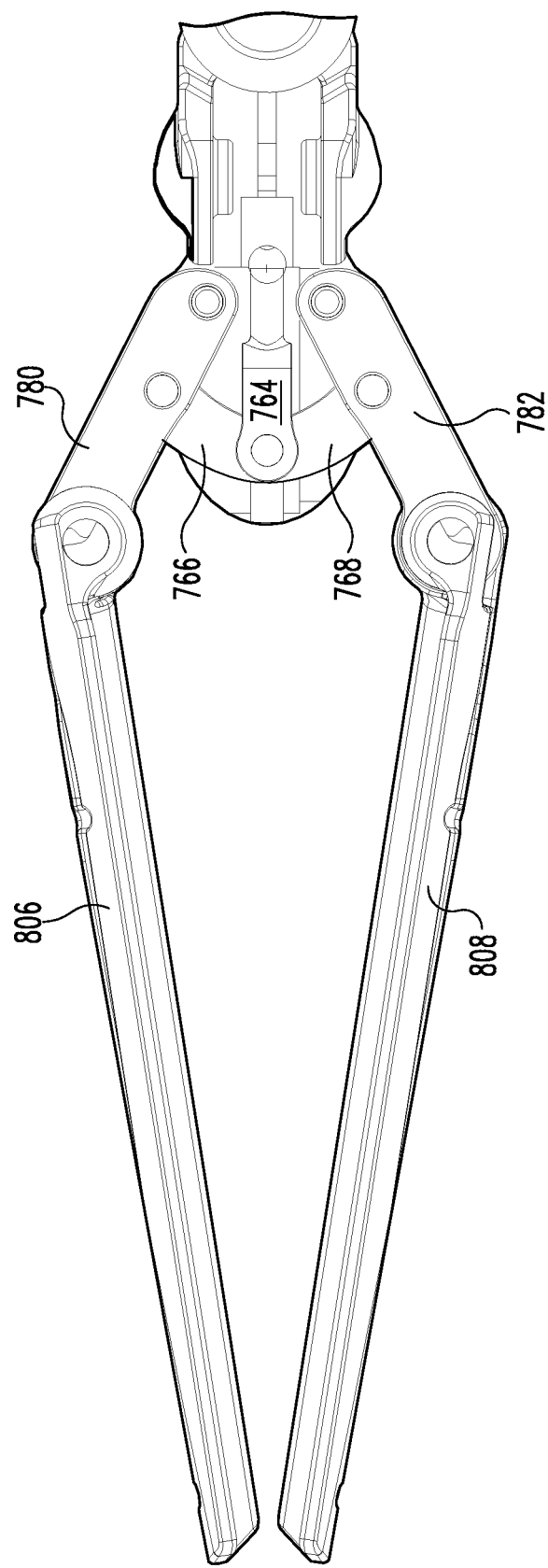
FIG. 64 is an overhead view showing the position of the jaws and various other distal end components of the exemplary laparoscopic device of FIG. 1 as the pull link is moved farther proximally that in FIG. 62.
Figure 65:
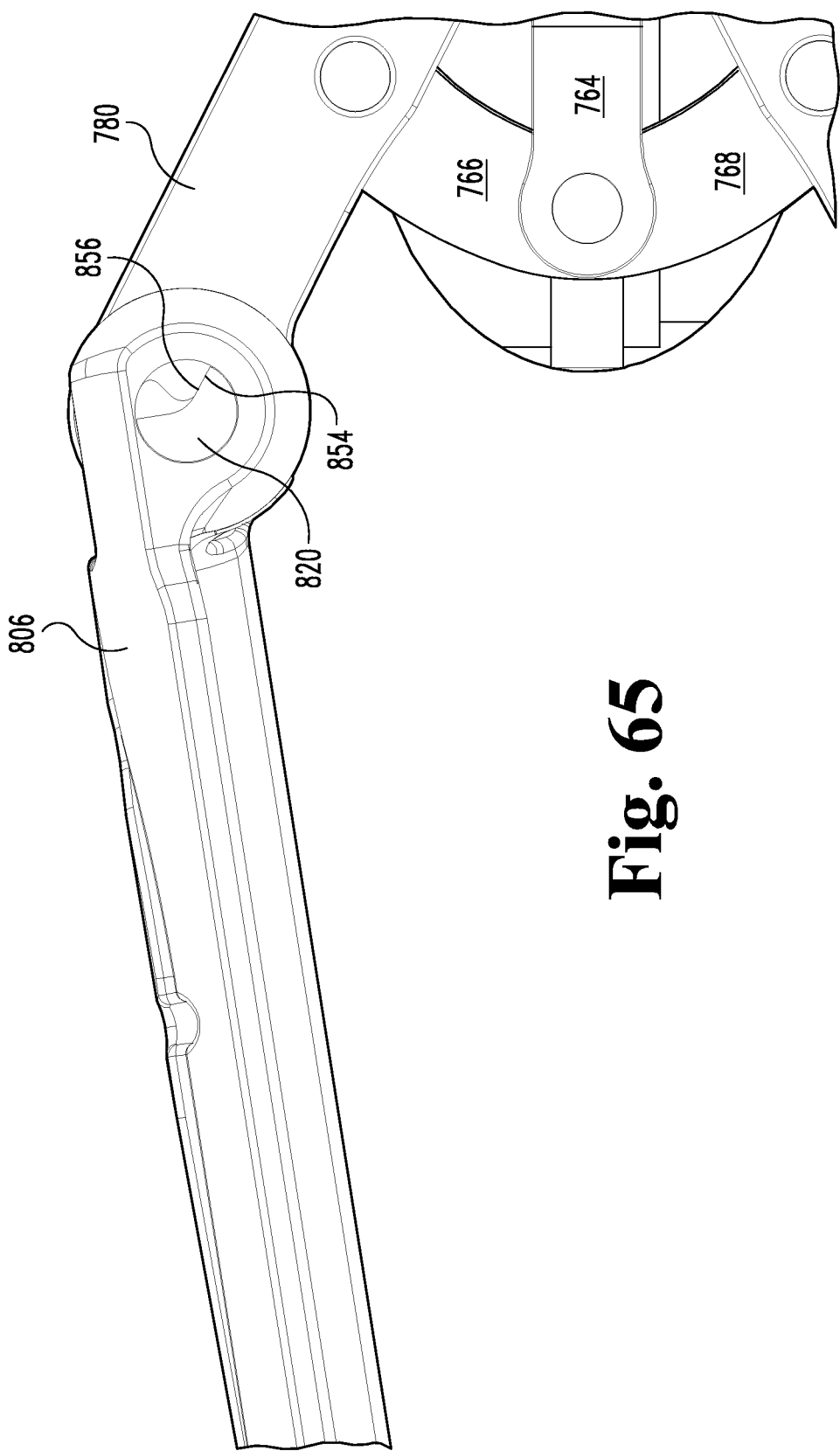
FIG. 65 is an overhead, magnified view of the jaws and link clips of FIG. 64.
Figure 66:
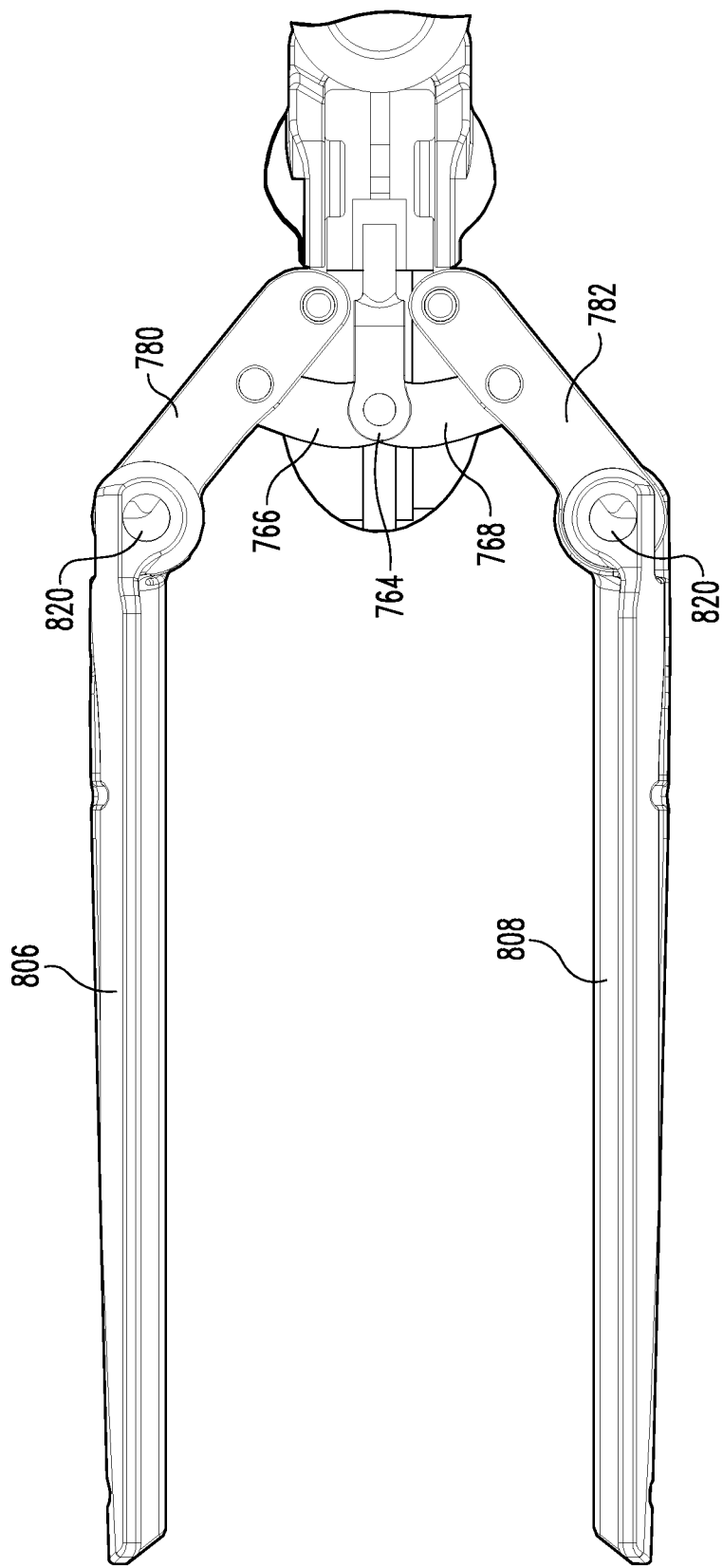
FIG. 66 is an overhead view showing the position of the jaws and various other distal end components of the exemplary laparoscopic device of FIG. 1 as the pull link is moved to its most proximal position to fully open the jaws.
Figure 67:
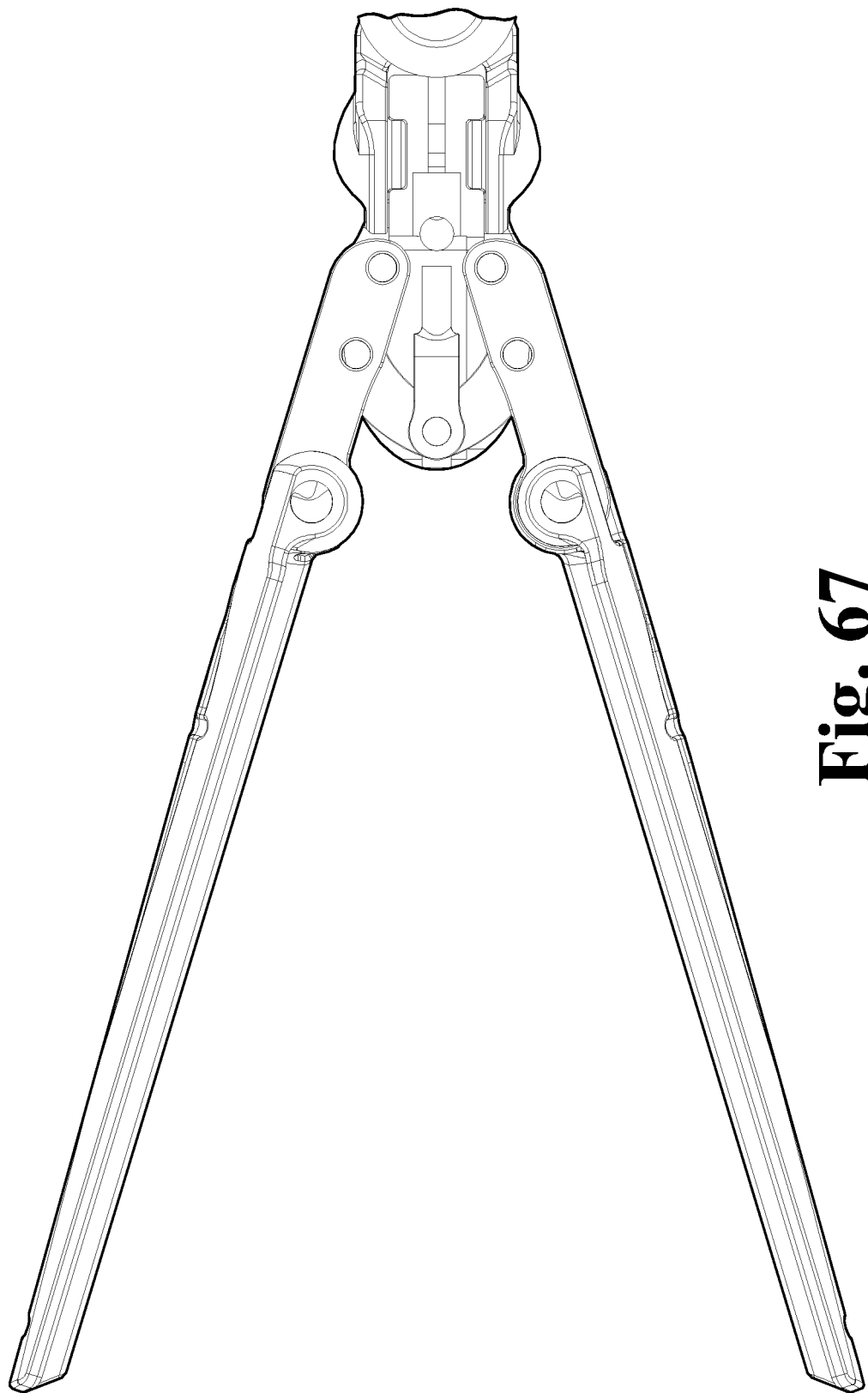
FIG. 67 is an overhead view showing the position of the jaws and various other distal end components if the exemplary laparoscopic device of FIG. 1 did not include a pivot point between the jaws and link clips.

Referring to FIGS. 44, and 62-66, in order to open the jaws 806, 808, the pull link 764 is pulled proximally via the connection wire 194. The proximal movement of the pull link 764 causes the ends of the right and left link plates 766, 768 coupled to the pull link to be repositioned proximally by pivoting around the dowel 796 extending through the pull link. Because the opposing ends of the link plates 766, 768 are pivotally coupled to the right and left link clips 780, 782 via the dowels 790, the motion of the pull link is operative to spread the distal ends of the link clips away from one another. As discussed previously, the three-quarter moon shaped opening 800 allows limited pivotal motion of the dowel 820 of a respective jaw 806, 808 with respect to the link clips 780, 782. In this manner, the pivotal motion between the link clips 780, 782 and the jaws 806, 808 causes the distal ends of the jaws 806, 808 to initially move closer to one another, while the proximal ends of the jaws move farther away from one another as shown in FIG. 62. While the link plates 766, 768 pivot with respect to the link clips 780, 782, the link clips are also operative to pivot with respect to the jaws 806, 808 evidenced by the first face 850 of the dowel 820 moving farther away from the first face 852 of the link clips as shown in FIG. 63. Continued proximal movement of the pull link 764 results in the distal ends of the link clips 780, 782 being moved even farther from one another as shown in FIG. 64. When in this position, as shown in FIG. 65, further pivoting action between the jaws 806, 808 and the link clips 780, 782 is inhibited by the second face 854 of the dowel 820 contacting the second face 856 of the link clips that defines a portion of the three-quarter moon shaped opening 800. In other words, the faces 852, 856 of the link clips 780, 782 provide range of motion boundaries for the dowel 820 to pivot between. When the second faces contact one another, the maximum angle is reached between the link clips 780, 782 and the jaws 806, 808. Thereafter, continued proximal movement of the pull link 764 to a maximum proximal end point (i.e., a travel limit) causes the distal ends of the link clips 780, 782 to reach a maximum spacing, which corresponds to the distal ends of the jaws 806, 808 moving apart from one another as shown in FIG. 66. In exemplary form, when the pull link 764 reaches the maximum proximal end point, the jaws 806, 808 arrive at a parallel position. This parallel position would not otherwise be obtainable without some pivotal motion between the jaws 806, 808 and the link clips 780, 782. As shown in FIG. 67, without the pivoting action between the link clips 780, 782 and the jaws 806, 808, the jaws would take on the angular orientation of the link clips and never arrive at a parallel position when spaced apart from one another when the pull link 764 reaches its proximal end-point.

Figure 68:
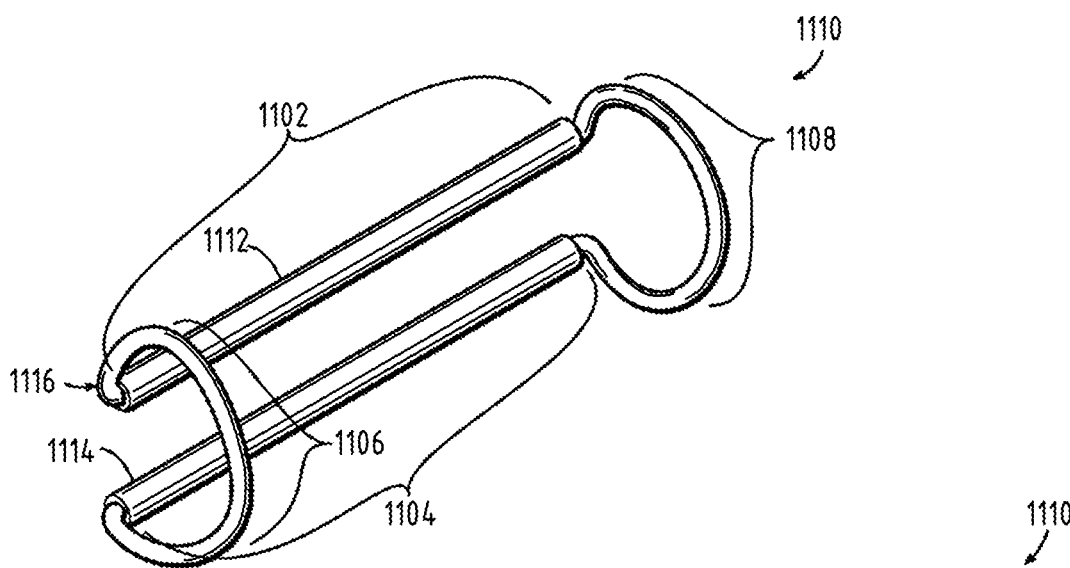
FIG. 68 is a perspective view of an exemplary clamp in an open position that may be used with the exemplary laparoscopic device of FIG. 1.
Figure 70:
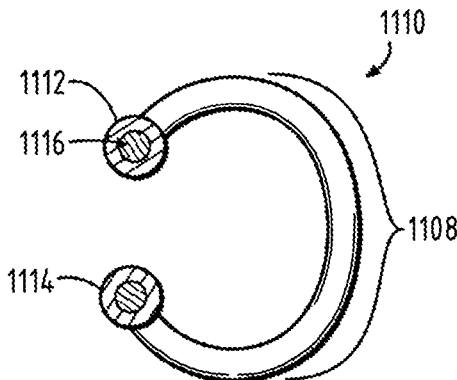
FIG. 70 is a cross-sectional view of the exemplary clamp of FIG. 68 in its open configuration, showing the wire member, rigid tubular members, and the urging members.

FIGS. 68 and 70 show one embodiment of a left atrial appendage occlusion clamp 1110 in an open position with spaced apart rigid clamping portions 1102, 1104 and resilient or elastic urging members 1106, 1108 at opposite ends of each clamping portion 1102, 1104. Clamping portions 1102, 1104 may be tubular, and both clamping portions 1102, 1104 may be at least substantially parallel to each other when arrest, i.e., when they are not being used to clamp tissue. Clamping portions 1102, 1104 may also be of substantially equal length or of different length, and each may be of larger outer diameter than the wire that may be used to form each of the urging members 1106, 1108. In this regard, the wire forming urging members 1106, 1108 can extend through the hollow interiors of the clamping portions 1102, 1104. In this illustrative example, the urging members 1106, 1108 are each shaped as a loop. The planes defined by the looped configuration of each of the urging members 1106, 1108 may be substantially parallel to each other and, in turn, substantially perpendicular to each of the clamping portions 1102, 1104. Of course, other angular orientations are possible as well.

Figure 69:
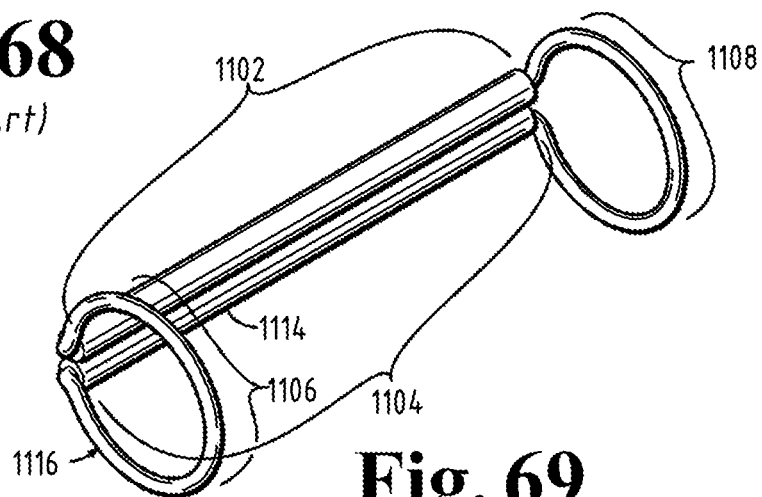
FIG. 69 is a perspective view of the exemplary clamp of FIG. 68 in a closed position.
Figure 71:
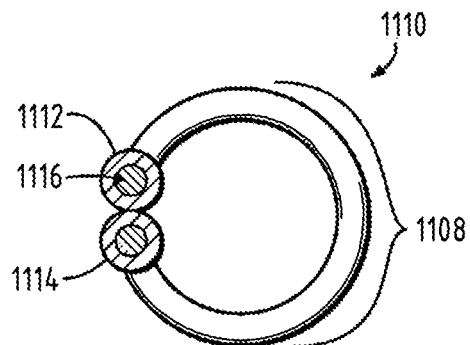
FIG. 71 is a cross-sectional view of the exemplary clamp of FIG. 69 in its closed configuration, showing the wire member, rigid tubular members, and the urging members.
Figure 72:
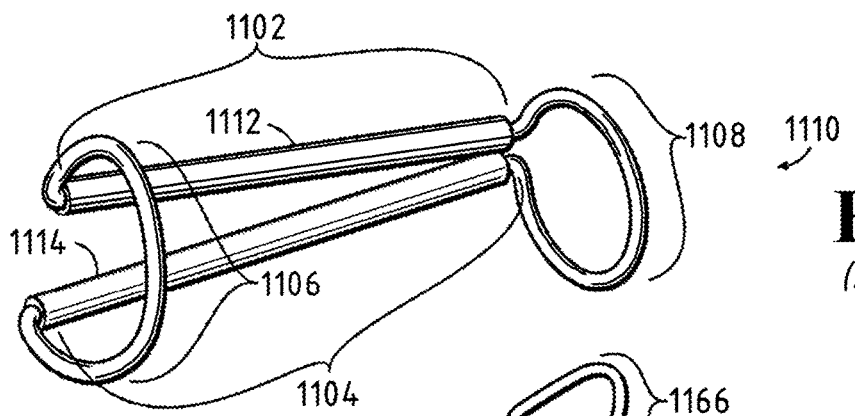
FIG. 72 is a perspective view of the exemplary claims of FIGS. 68-71 and showing the ability to close in a non-parallel fashion.
Figure 73:
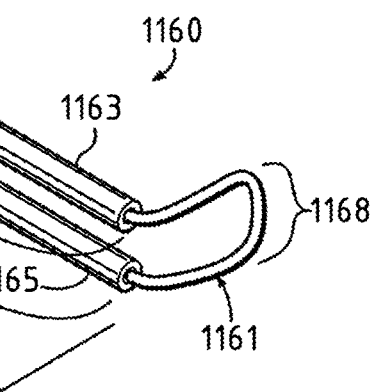
FIG. 73 is a perspective view of the first stage of assembly of an alternate embodiment of a clamp, showing a wire member surrounded by rigid tubular members.
Figure 74:
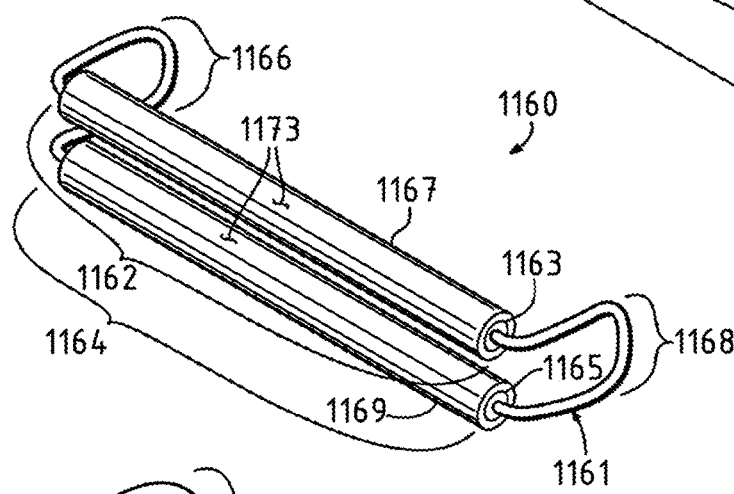
FIG. 74 is a perspective view of the second stage of assembly of the clamp of FIG. 73, in which platens have been added over the rigid tubular members.

FIGS. 69 and 71 show the same clamp 1110 of FIGS. 68 and 70 with the clamping portions 1102, 1104 in their normally biased together positions. Contact between the clamping portions 1102, 1104 may occur initially along their entire parallel lengths as shown. Of course, when clamping portions 1102, 1104 are covered in fabric or other material as later described, contact may occur between the fabric or other material instead. In FIGS. 68-71, only the structure and relative positions of the rigid members 1102, 1104 and urging members 1106, 1108 are shown. The final assembly is depicted in FIGS. 72-74 which, although describing a slightly different embodiment, show the general steps in the construction of each embodiment. The clamping portions 1102, 1104 may be made from rigid tubes 1112, 1114 of a rigid metal such as titanium disposed over a wire member 1116. In this embodiment, titanium is used for its compatibility with MRI imaging, its bio compatibility and its galvanic compatibility with the wire member 1116 when the wire member 1116 is formed from superelastic materials such as a nickel titanium alloy. This embodiment and the other embodiments disclosed herein may use a superelastic material such as a nickel titanium alloy to form the urging members 1106, 1108. Superelastic properties will allow the material to be greatly extended to open the clamping portions 1106, 1108 of the clamp 1110 without permanently deforming the material. These superelastic materials can also be compatible with MRI imaging and easily tolerated as an implant material in the body. The rigid tubular members 1112, 1114 of this embodiment are mechanically fastened to the underlying wire member 1116 preferably by mechanically swaging the titanium tubes 1112, 1114 to the wire members 1116. Although a single, continuous wire member is shown directed through both clamping portions 1102, 1104 and urging members 1106, 1108, the clamp 1110 of this embodiment may also be made with two or more wires, or with any other suitable components.

As shown in FIG. 72, in addition to being able to close on tissue or anatomical structure in a parallel fashion, the clamp 1110 can also apply force to the anatomical structure in a nonparallel clamping fashion. This allows the clamp 1110 to accommodate non-uniform tissue thickness over the length of the clamping portions 1102, 1104. In addition, with separate urging members 1106, 1108 at opposite ends of the clamping portions 1102, 1104 the nonparallel clamping can originate from either side of the clamp 1110. The nonparallel clamping feature of this embodiment allows the clamp 1110 to accommodate a wide range of hollow anatomical structures with varying wall thicknesses throughout its length and breadth. For example, some anatomical structures such as atrial appendages of the heart have internal structures called trabeculae, which are non-uniform and very often cause variable thicknesses across one or more of their dimensions. Nonuniform clamping, therefore, can be advantageous in this application for this reason or for other reasons.

FIG. 73 shows an alternate embodiment of a clamp 1160 including two urging members 1166, 1168 shaped to resemble a letter "U" instead of the more circular loop configuration of the embodiment of FIGS. 68-71. As is the case with the first clamp 1110, the U-shaped urging members 1166, 1168 of clamp 1160 may also lie in planes generally parallel to each other and perpendicular to the axes of the clamping portions 1162, 1164. A potential use of the embodiment of FIG. 73 may lie in the lesser force exerted by U-shape urging members 1166, 1168 on the clamping portions 1162, 1164 with respect to the force exerted by the loop-shape urging members 1106, 1108 of clamp 1110 in FIGS. 68-71, making it more suitable for clamping of anatomical structures not requiring a relatively high clamping force. The U-shape configuration of the urging members 1166, 1168 generally requires less space in the direction perpendicular to the axes of the clamping portions 1162, 1164. FIG. 73 shows a first stage of assembly of the clamp 1160, where the rigid tubular members 1163, 1165 are joined with the superelastic wire member 1161. In this embodiment, mechanical swaging is used to join the tubular members 1163, 1165 to the wire 1161. However, adhesives or laser welding or other methods of attachment could be easily used instead. Similarly, it will be appreciated that rigid tubular members 1163, 1165 may not necessarily need to be bonded to wire member 1161 at all. One may rely, for example, on designing the rigid tubular members 1163, 1165 so that their inside diameters simply closely fit over the wire 1161. In addition, the rigid tubular members 1163, 1165 could take on many different cross sectional shapes. Cross-sectional shapes such as ovals, triangles or rectangles with rounded edges could be preferable and may eliminate the addition of the load spreading platens 1167, 1169 shown in FIG. 74, as these alternate shapes may provide a larger area of contact against the anatomical structure to be engaged by the clamp 1150. Since different anatomical structures greatly vary from subject to subject, it is advantageous to have a manufacturing method in which the length 1171 of the clamp 1160 can be easily varied. By cutting rigid members 1163, 1165 to various different lengths, different size assemblies can be configured.

FIG. 74 shows the next step in the assembly of the clamp. Load spreading platens 1167, 1169 made of plastic or other biocompatible material such as urethane, may be slipped over the titanium or other suitable material tubing that forms rigid tubular members 1163, 1165, to provide a resilient surface 1173 to spread the load out onto a larger surface area, thereby preventing point source loading of the tissue which might otherwise result in cutting of the tissue before it has had a chance to become internally fused. The platens 1167, 1169 can be assembled and applied over the rigid tubular members 1163, 1165 prior to the swaging step or platens 1167, 1169 can alternatively be manufactured in such a way so as to have a longitudinal split which allows the material to be opened and forced onto the rigid tubular members 1163, 1165.

Figure 75:
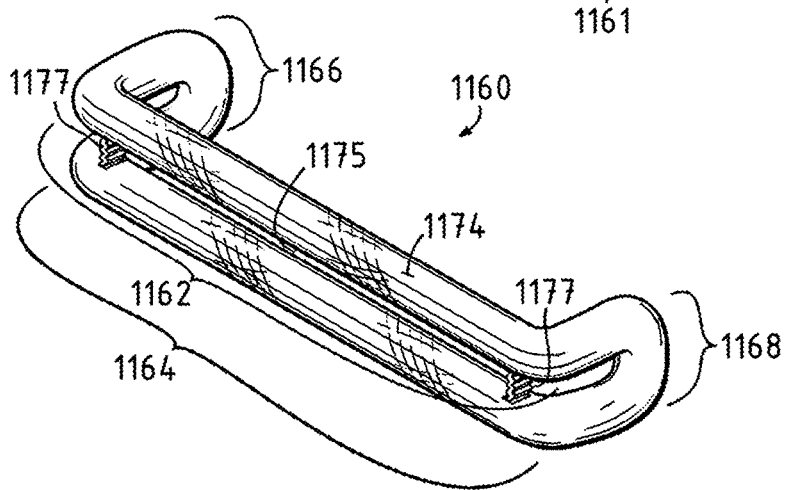
FIG. 75 is a perspective view of the clamp of FIGS. 73 and 74, once an outer fabric covering has been disposed over the entire surface of the clamp.
Figure 76:
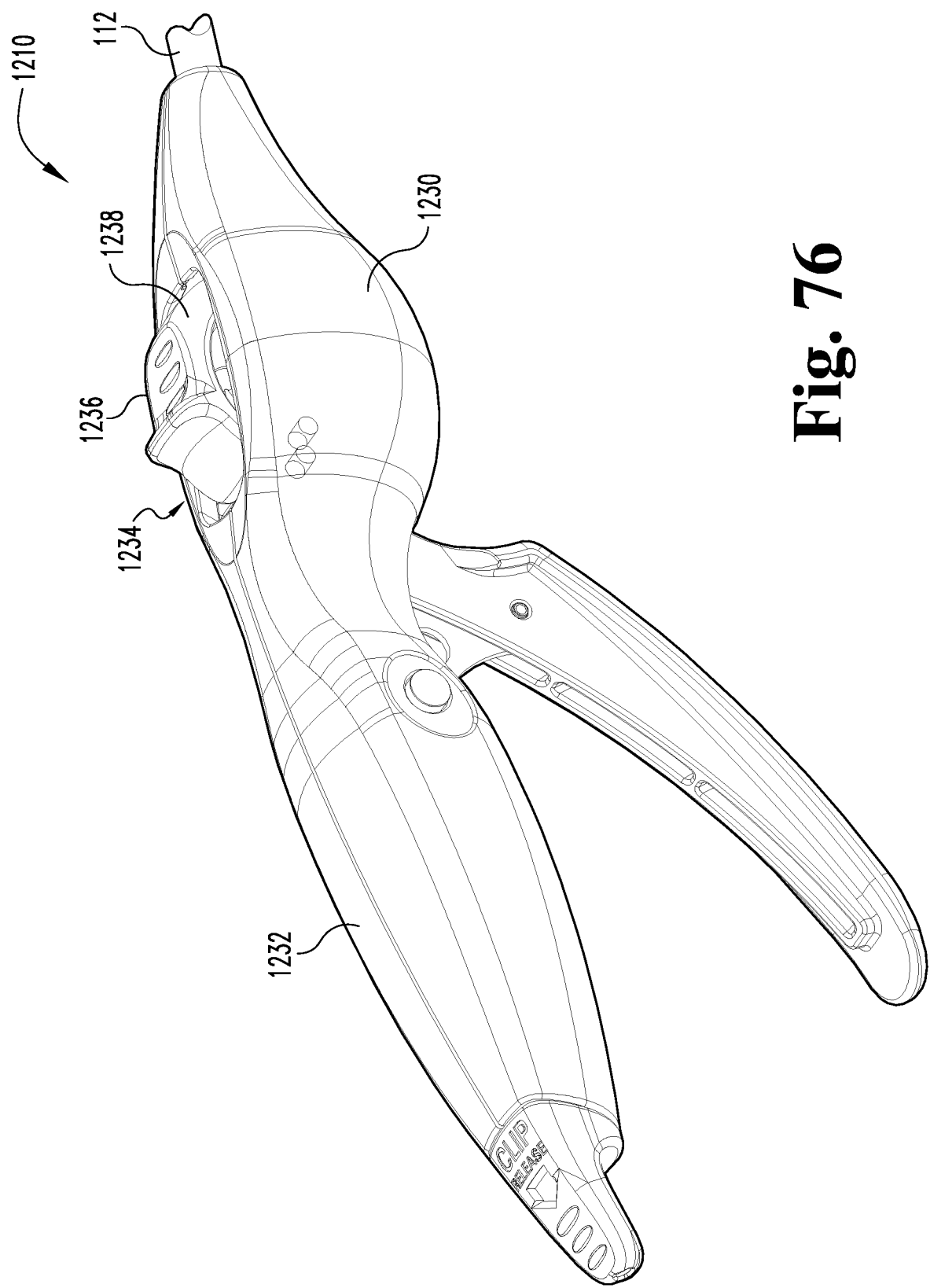
FIG. 76 is an elevated perspective view of an alternate exemplary controller that may be used with the laparoscopic device of FIG. 1.
Figure 77:
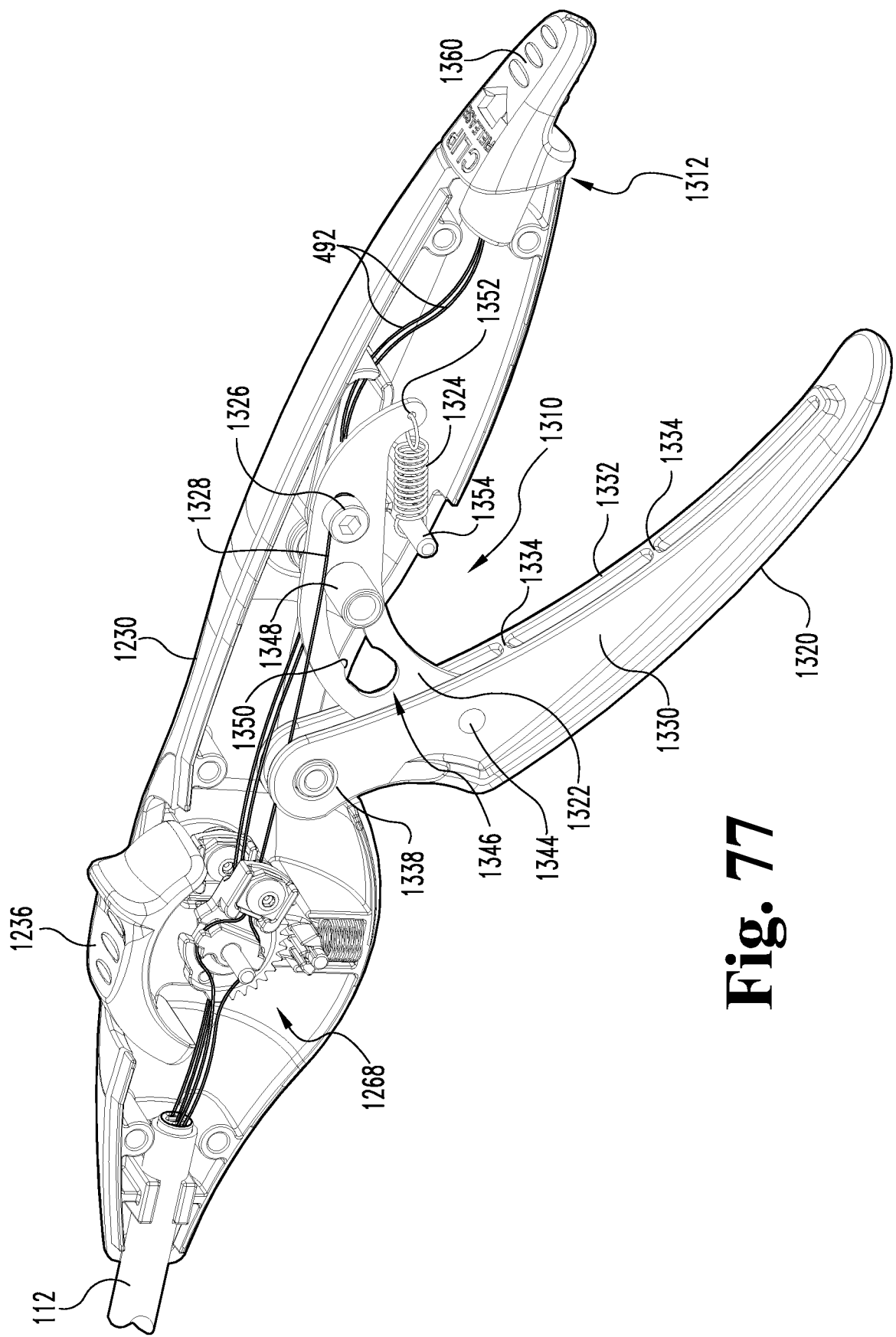
FIG. 77 is an elevated perspective view of the alternate exemplary controller of FIG. 76, shown without the left side housing.
Figure 78:
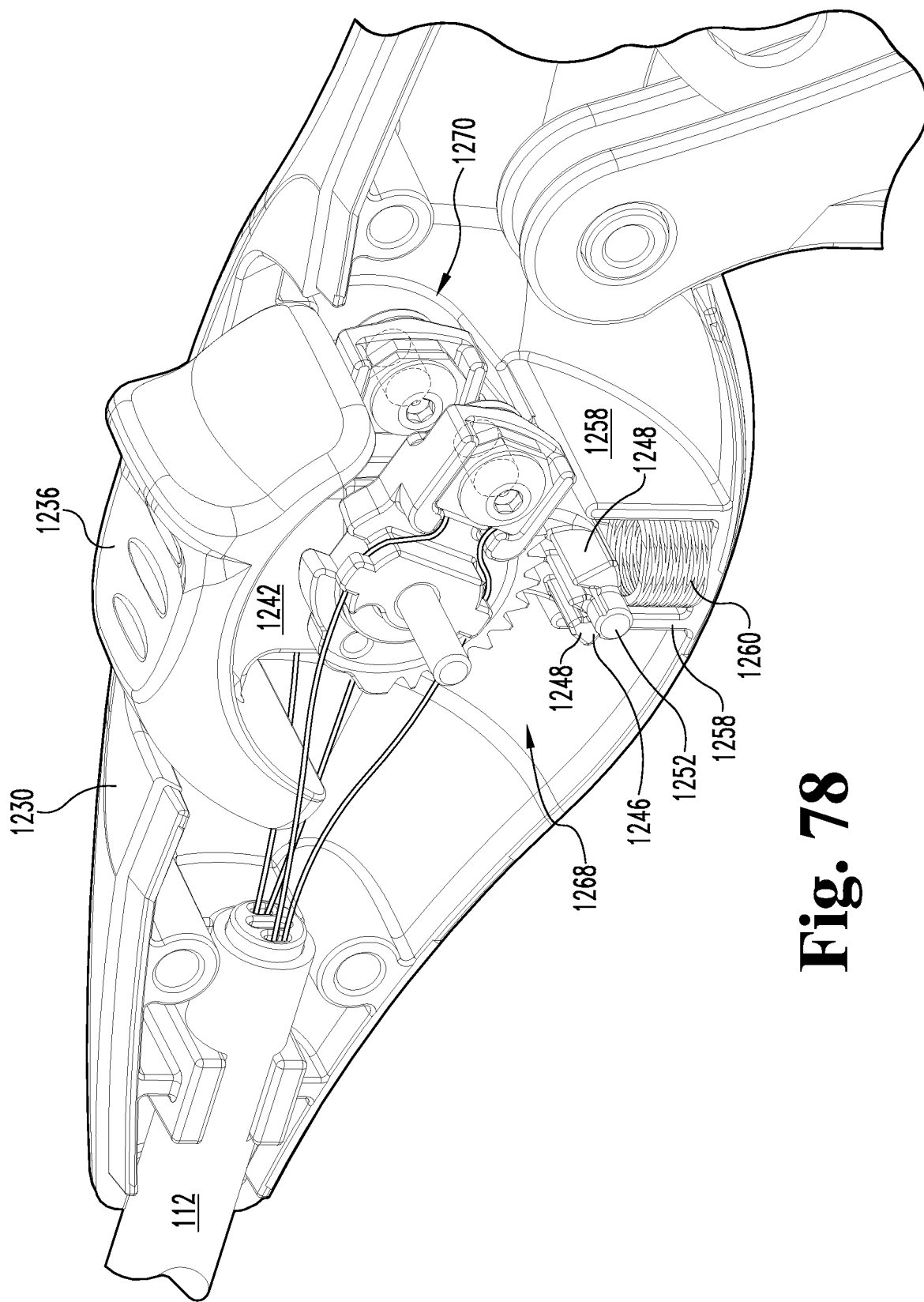
FIG. 78 is a magnified, perspective view of the interior of a distal portion of the alternate exemplary controller of FIG. 76.

FIG. 75 shows the clamp 1160 after a fabric cover material 1174 made of material such as polyester has been sewn around the clamping portions 1162, 1164 and urging members 1166, 1168. It will be appreciated that this material or any other similar materials may be used as a full or partial covering in any of the disclosed embodiments. Such a material is preferably suitable to engage the tissue of the anatomical structure being clamped as well as that of surrounding areas. Preferably, the material 1174 is circular warp knit fabric tube, with a diameter of approximately 4 to 5 mm and made from a combination of 4/100, 2/100 and 1/100 textured polyester. The material 1174 may also be heat-treated to cause a velour effect. The fabric or other material 1174 is furthermore sewn or otherwise applied over the urging members 1166, 1168. In addition, fabric pieces 1177 may be attached at opposite respective ends of clamping portions 1162, 1164 to prevent any part of the engaged anatomical structure from escaping the annular occlusion area between the clamping portions 1162, 1164. In other words, fabric pieces 1177 act as tissue blocking members or dams at opposite ends of the clamp. This or another tissue blocking feature may also be implemented into any other embodiment. This is desirable as it minimizes the probability of unintentionally leaving any part of the engaged anatomical structure unclamped. The material 1177, like material 1174, can also promote tissue in-growth.

Referring to FIGS. 76-82, an alternate exemplary controller 1210 may be used in place of the foregoing controller 110 with the exemplary laparoscopic device 100. Similar to the first controller 110, this alternate exemplary controller 1210 may be coupled to the semi-rigid conduit 112 in order to manipulate a repositionable mechanism (not shown) operatively coupled to the end effector 118. But, as will be discussed in more detail hereafter, this exemplary controller 1210 incorporates a dual passive mechanism in order to control the pitch (i.e., up and down) and the yaw (i.e., side to side) of the end effector. In exemplary form, unlike the first exemplary controller 110, this alternate exemplary controller 1210 does not includes an active mechanism to manipulate the pitch of the end effector 118, but instead utilizes a passive system that is operative to lock in the end effector in one of a predetermined number of pitch positions.

The controller 1210 comprises a right side housing 1230 and a left side housing 1232 that cooperatively define an internal cavity and corresponding openings to accommodate throughput of certain controls. A first of these openings is a dorsal opening 1234 that accommodates throughput of a vertically repositionable button 1236. As will be discussed in more detail hereafter, the repositionable button 1236 may be manipulated vertically to lock and unlock the repositionable mechanism 116 in order to provide for or constrain lateral and vertical adjustability of the end effector 118.

The repositionable button 1236 comprises a proximal-to-distal arcuate top 1238 that includes bumps and a proximal ridge to accommodate the thumb of a user being positioned on top of the button. The medial-to-lateral width of the arcuate top 1238 is generally constant and overlaps a vertical, planar appendage 1242 that extends from the underside of the arcuate top. This vertical appendage 1242 has a relatively constant and minimal medial-to-lateral dimension, but includes a proximal-to-lateral dimension that tapers from a maximum where the appendage extends from the arcuate top, to a minimum where the appendage ends. At the end of the appendage 1242, a pair of tooth receivers 1246 extend outward in the medial and lateral directions from opposing sides of the appendage. The tooth receivers 1246 each include a series of longitudinal pyramidal shapes 1248 that are in parallel and radially arranged in order to define a series of corresponding longitudinal pyramidal cavities 1250. At the medial end of the medial tooth receiver 1246 and at the lateral end of the lateral tooth receiver 1246 is a cylindrical projection 1252 that is received within corresponding vertical, oblong grooves 1254 on the interior of the housings 1230, 1232. These grooves 1254 inhibit significant medial-to-lateral and proximal-to-distal travel of the tooth receivers 1246 as the tooth receivers are vertically repositioned. In other words, as the button 1236 is depressed vertically, the toothed receivers 1246 are vertically repositioned in a corresponding vertical manner. In this way, the movement of the toothed receivers 1246 is directly attributable to the movement of the button 1236 as the toothed receivers are indirectly mounted to the button via the appendage 1242.

Figure 79:
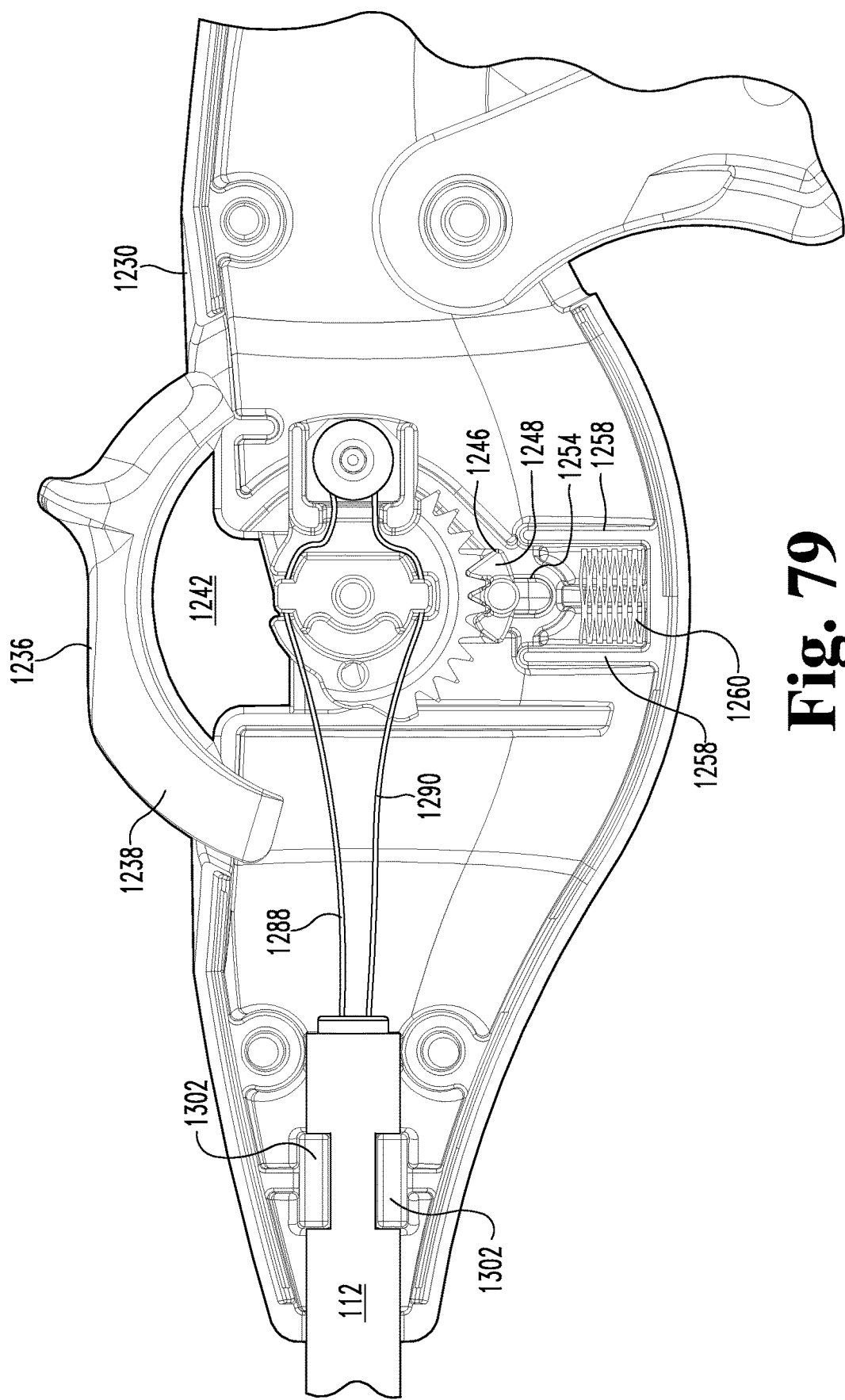
FIG. 79 is a profile view of the structure shown in FIG. 78 with the button shown in its highest vertical position.
Figure 80:
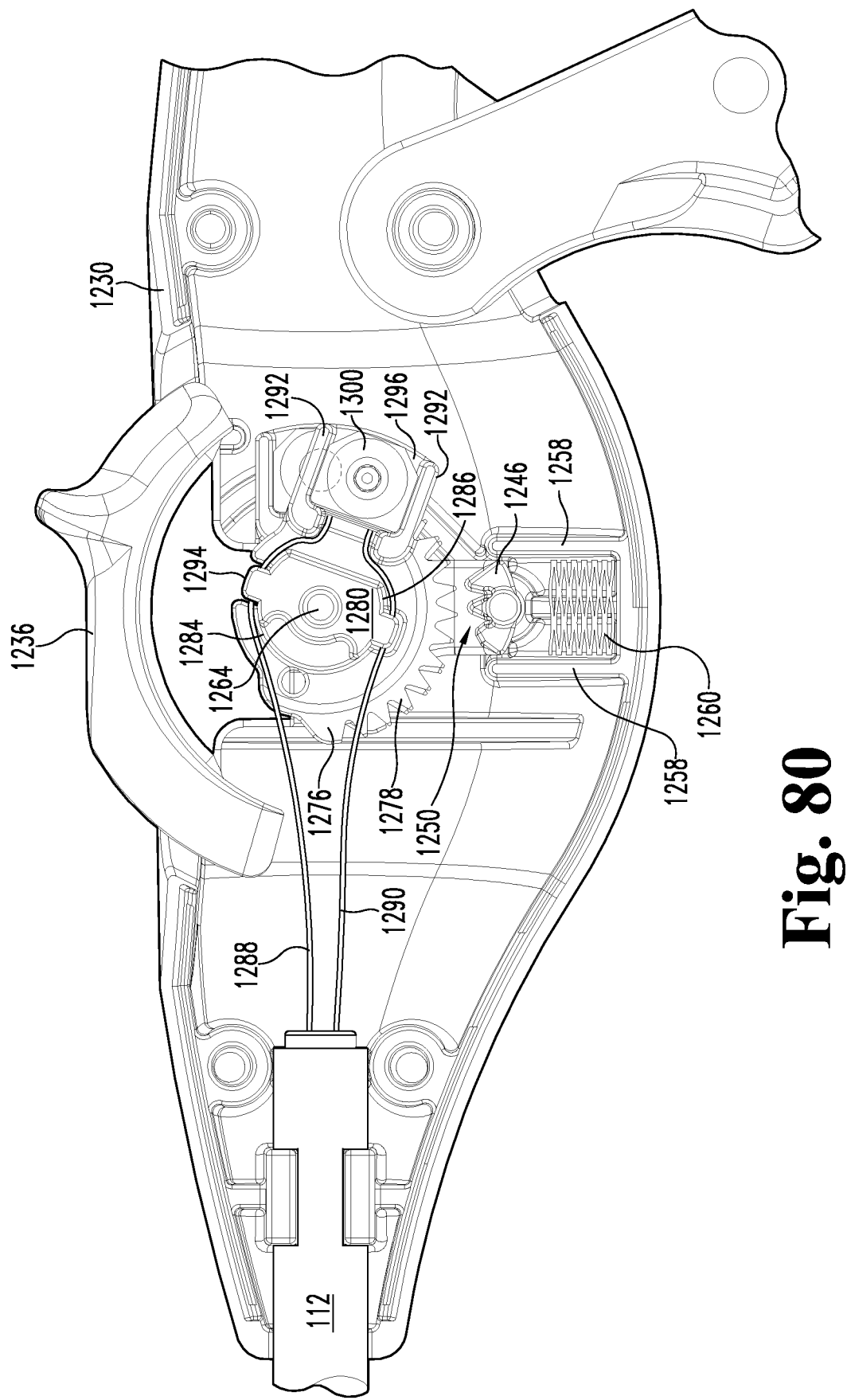
FIG. 80 is a profile view of the structure shown in FIG. 78 with the button shown depressed in its lowest vertical position.
Figure 81:
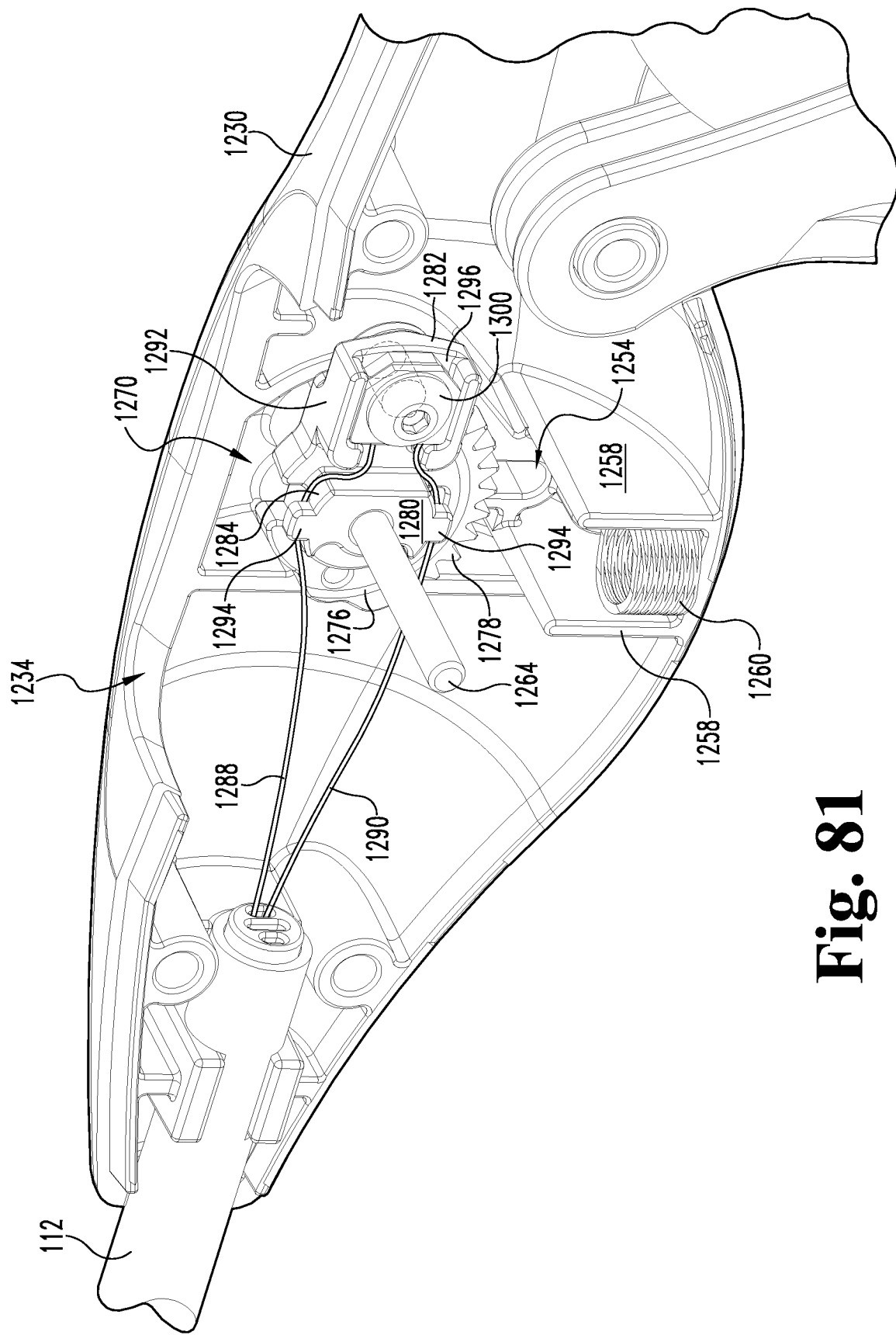
FIG. 81 is a magnified, perspective view of the interior of a distal portion of the alternate exemplary controller of FIG. 76, shown without the button and first toothed assembly.
Figure 82:
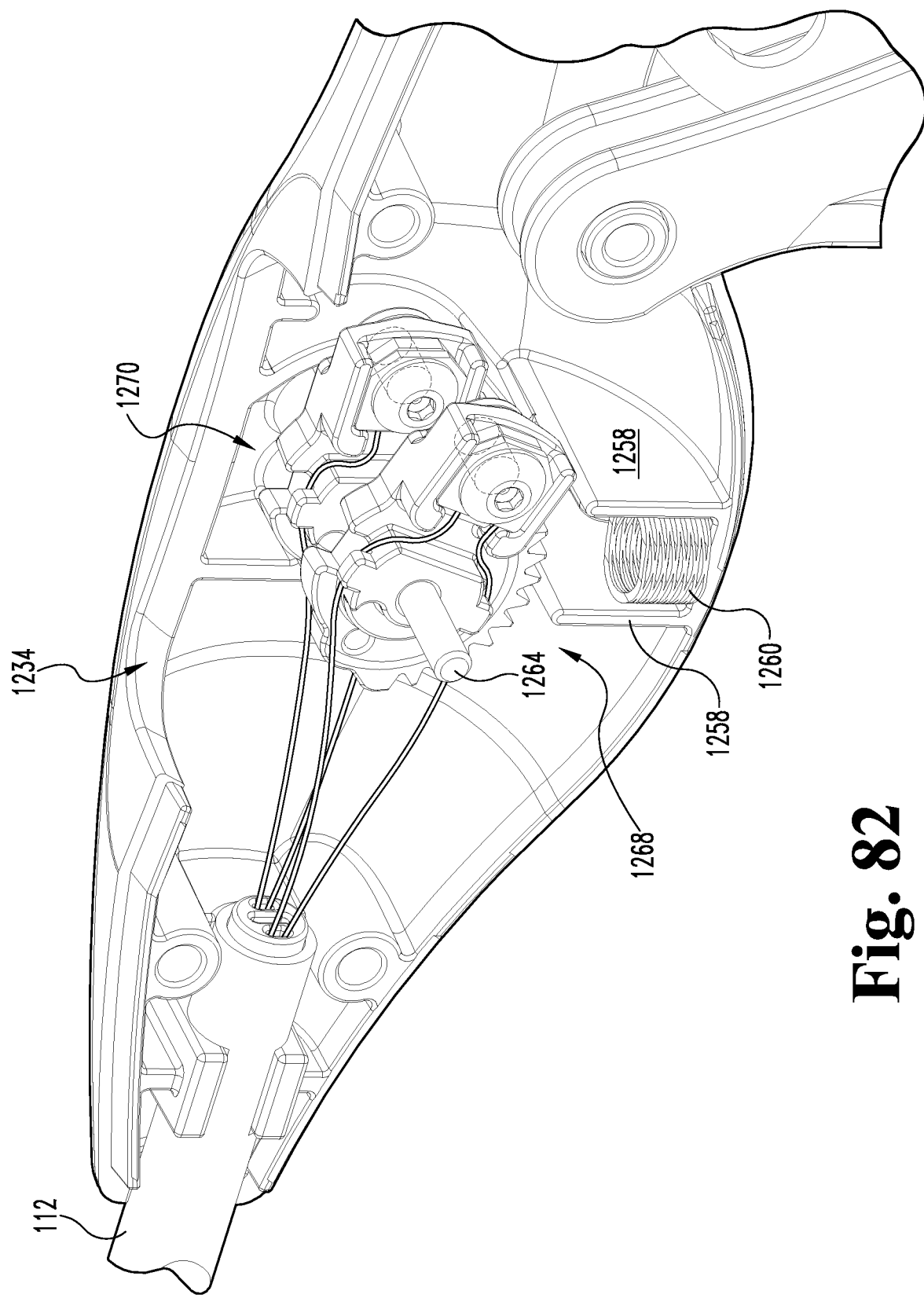
FIG. 82 is a magnified, perspective view of the interior of a distal portion of the alternate exemplary controller of FIG. 76, shown without the button.

The button 1236 is biased vertically to its highest vertical position shown in FIG. 79. To achieve this bias, the housings 1230, 1232 includes parallel walls 1258 that cooperate to form medial-to-lateral trench within which at least one spring 1260 is seated. The spring 1260 is rated at a sufficient spring force to overcome the weight of the button 1236, appendage 1242, tooth receivers 1246, and cylindrical projections 1252 to force the button to its highest vertical position. But the spring force is not so great that it requires too great a force from a user's thumb to depress the button 1236 and overcome the bias of the spring 1260.

An axle 1264 extends in the medial-to-lateral direction within the interior cavity cooperatively defined by the housings 1230, 1232. This axle 1264 is cylindrical in shape and includes a constant longitudinal diameter, thereby giving the axle a circular circumference. In exemplary form, the medial and lateral ends of the axle 1264 are received within corresponding cylindrical cavities (not shown) on the interior of the housings. The depth of these cavities is not so great as to cover the majority of the axle 1264. The exposed cylindrical portion of the axle 1264 is operative to receive a pair of toothed assemblies 1268, 1270 that are interposed by the appendage 1242, which itself includes a vertical, oblong orifice (not shown) to accommodate throughput of the axle and vertical travel of the appendage with respect to the axle, which has a fixed orientation. In exemplary form, the toothed assemblies 1268, 1270 includes a through cylindrical orifice 1272 allowing the assemblies to rotate on the outside of the axle.

Each of the toothed assemblies 1268, 1270 are identical to each other. Accordingly, a redundant description of the second toothed assembly has been omitted in furtherance of brevity. The toothed assemblies 1268, 1270 include a wheel 1276 having circumferentially distributed teeth 1278 that are sized to engage a respective tooth receivers 1246 and be received within the longitudinal pyramidal cavities 1250 when the tooth receivers in a raised vertical position (see FIG. 79). The wheel 1276 has a generally uniform width but for a pair of outgrowths 1280, 1282. The first outgrowth 1280 is generally centered radially with respect to the wheel and partially defines the through orifice 1272 that receives the axle 1264. This first outgrowth 1280 is semicircular in shape extends medially from the wheel 1276 and includes a corresponding top and bottom arcuate surfaces 1284, 1286 that are radially inset with respect to the wheel. These arcuate surfaces 1284, 1286 act as caroming surfaces for respective connection wires 1288, 1290 that extend from the second outgrowth 1282. The first outgrowth 1280 also includes a pair of vertical flanges 1294 that extend from the arcuate surfaces 1284, 1286 and cooperate with the circumferential ends of the wheels in order to provide medial and lateral guides for the connection wires 1288, 1290 so that the connection wires stay therebetween. The second outgrowth 1282 is proximally oriented with respect to the first outgrowth 1280 and includes a rectangular profile with a pair of L-shaped walls 1292 and floor 1296 cooperating to define an internal cavity. An opening (not shown) extends through the floor and into the cavity. This opening receives a fastener (such as a screw) 1300 around which the connection wires 1288, 1290 are wound and secured in place. The fastener 1300 is also recessed within the cavity so that the L-shaped walls 1292 extend laterally beyond the end of the fastener. Accordingly, the connection wires 1288, 1290 extending from the fastener are threaded through a gap between the L-shaped walls 1292, with one of the wires being threaded over the top arcuate surface 1284, while the second wire is threaded under the bottom arcuate surface 1286. Thereafter, the wires 1288, 1290 extend distally and taper to extend through a respective eyelet opening at the proximal end of the conduit 112.

Each of the toothed assemblies 1268, 1270 is independently rotatably repositionable with respect to one another. The first toothed assembly 1268 is operative provide part of a passive repositionable mechanism in order to control the pitch (i.e., up and down) of the end effector 118, while the second toothed assembly 1270 is operative to provide part of a passive repositionable mechanism in order to control the yaw (i.e., side to side) of the end effector. In exemplary form, when the button 1236 is not depressed, the spring 1260 is operative to bias the toothed receivers 1246 into engagement with the teeth 1278 of the toothed assemblies 1268, 1270, thereby inhibiting rotation of the toothed assemblies around the axle 1264. When the tooth assemblies 1268, 1279 are locked in position (see FIG. 79) the end effector 118 cannot be repositioned in the vertical direction (i.e., affecting pitch) or in the medial-to-lateral direction (i.e., affecting yaw). Thus, when the tooth assemblies 1268, 1279 are locked in position (see FIG. 79), so too is the end effector 118 locked in position.

In order to change the vertical or medial-to-lateral position of the end effector 118, a user would depress the button 1236. By depressing the button 1236, the toothed receivers 1246 are operative to further compress the spring 1260 and disengage the toothed assemblies 1268, 1270. More specifically, the longitudinal pyramidal shapes 1248 and corresponding longitudinal pyramidal cavities 1250 no longer engage the teeth 1278 of the toothed assemblies 1268, 1270, thereby allowing rotation of the toothed assemblies around the axle 1264. By allowing free rotation of the toothed assemblies 1268, 1270 around the axle 1264, the connection wires 1288, 1290 linking the end effector 118 and the toothed assemblies may be repositioned, which allows the end effector to be freely repositionable in the vertical direction (i.e., affecting pitch) and in the medial-to-lateral direction (i.e., affecting yaw). After the respective vertical and medial-to-lateral position of the end effector 118 has been reached, the user would discontinue depressing the button 1236 to lock in the relative vertical and medial-to-lateral positions. In order to lock in the positions, the spring 1260 forces the toothed receivers 1246 upward and into engagement with the toothed assemblies 1268, 1270. Because the toothed assemblies 1268, 1270 include teeth 1278 that engage the longitudinal pyramidal shapes 1248 of the toothed receivers 1246, the spring 1260 will direct the toothed receivers upward and cause the toothed assemblies to possibly rotate slightly about the axle 1264 so that the teeth are fully received within the longitudinal pyramidal cavities 1250. If the position of the end effector 118 is such that the teeth 1278 are aligned with the longitudinal pyramidal cavities 1250, then the vertical and medial-to-lateral positions will be precisely maintained because of the tension on the connection wires 1288, 1290. But if the position of the end effector 118 is such that the teeth 1278 are slightly misaligned with the longitudinal pyramidal cavities 1250, then the vertical and medial-to-lateral positions will be changed as the toothed assemblies 1268, 1270 rotate slightly about the axle 1264 so that the teeth are fully received within the longitudinal pyramidal cavities 1250. After the teeth 1278 are aligned and received within the longitudinal pyramidal cavities 1250, the vertical and medial-to-lateral positions will be precisely maintained because of the tension on the connection wires 1288, 1290.

In order to maintain the orientation of the semi-rigid conduit (which carries the connection wires 1288, 1290) with respect to the housings 1230, 1232, a distal portion of the right side housing 1230 includes a pair of detents 1302 that engage the semi-rigid conduit 112. These detents 1302 inhibit longitudinal movement of the conduit 112 with respect to the controller 1210. Both detents 1302 extend in parallel to one another and extend from an interior circumferential surface of the right side housing 1230.

The right and left side housings 1230, 1232 cooperate to delineate a handle mechanism port 1310 and a proximal port 1312 open to the interiors of the respective housings. The handle mechanism port 1310 accommodates throughput of a portion of a handle mechanism 1318 that comprises a repositionable handle 1320, a drive plate 1322, a return spring 1324, and a wire retainer 1326. As will be discussed in more detail hereafter, the wire retainer is concurrently coupled to a draw wire 1328 and the drive plate 1322 so that movement of the handle 1320 is operative to open and close an occlusion clip 1160 (see FIG. 75), such as during an atrial appendage occlusion clip deployment surgical procedure. A more detailed explanation of the respective components of the handle mechanism 1318 follows.

The repositionable handle 1320 includes an arcuate, ventral gripping surface that may include a series of convex bumps longitudinally spaced apart to facilitate gripping by a user. Opposite the ventral gripping surface is a corresponding interior surface from which a pair of spaced apart, parallel vertical walls 1330, 1332 extend. The vertical walls 1330, 1332 are also connected to one another via a plurality of cross walls 1334. The vertical walls 1330, 1332 each include a distal upstanding loop 1338 that provides a through opening in the medial-to-lateral direction to receive a axle 1340 extending from the right side housing 1230 around which the handle 1320 rotates. Extending distally from the loop 1338, the walls 1330, 1332 include a circular opening extending in the medial-to-lateral direction that receives a pin 1344 in order to repositionably mount the drive plate 1322 to the handle 1320.

The exemplary drive plate 1322 comprises an arcuate, flat plate sized to fit between the walls 1330, 1332 of the handle 1320. A distal end of the plate 1322 includes an opening to receive the pin 1344. Extending proximally from the opening is an elongated, arcuate opening 1346 adapted to receive a dowel 1348 extending from the interior of the right side housing 1230. In this manner, the dowel 1348 is repositioned with respect to the opening 1346 as the handle 1324 repositions the drive plate 1322. In exemplary form, the opening is partially defined by a lip 1350 that acts to retain the dowel 1348 in a static position after the handle 1320 is fully closed. At the same time, the proximal end of the drive plate 1322 includes an orifice 1352 that receives a portion of the spring 1324 in order to bias the handle 1320 to the open position shown in FIG. 77. The opposing end of the spring 1324 is mounted to a dowel 1354 that extends from the interior of the right side housing 1320.

The controller 1210 also includes a removable stem 1360 that is seated within the proximal port 1312 of the housings 1230, 1232. The removable stem 1360 is coupled to one or more clip release wires 492 (in this case, two clip release wires) that act to disconnect an occlusion clip from the clip deployment device 118. In this manner, the stem 1360 may be removed from the proximal end of the controller 1210, thereby drawing the release wire(s) proximally and disconnecting the occlusion clip from the clip deployment device 118. In this exemplary embodiment, the stem 1360 is secured within the proximal port 1312 via a friction fit that may be overcome by the user applying pressure to the stem to move it proximally with respect to the controller 1210. But it is also within the scope of the disclosure to use detents or other affirmative release mechanisms to release the stem 1360 from the controller 1210.

Following from the above description and invention summaries, it should be apparent to those of ordinary skill in the art that, while the methods and apparatuses herein described constitute exemplary embodiments of the present invention, the invention is not limited to the foregoing and changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A medical instrument comprising:
a hand-held control at least partially housing a plurality of controls;
a first joint including first joint components that are repositionable with respect to one another within a first degree of freedom;
a second joint operatively coupled to the first joint, the second joint including second joint components that are repositionable with respect to one another within a second degree of freedom, the second degree of freedom being different than the first degree of freedom;
an elongated conduit operatively coupling the hand-held control to at least one of the first joint and the second joint; and,
an open-ended occlusion clip deployer comprising a pair of repositionable jaws operatively coupled to the second joint, each of the pair of repositionable jaws pivotally coupled to a respective link clip that is operatively coupled to at least a portion of the second joint, each of the respective link clips being operatively coupled to a drive cable via a respective link plate, where the drive cable comprises a portion of one of the plurality of controls.

2. The medical instrument of claim 1, further comprising an occlusion clip removably coupled to the pair of repositionable jaws, the occlusion clip comprising a pair of beams each having a longitudinal axis extending along a dominant dimension thereof, the pair of beams biased toward one another transverse to the longitudinal axes.

3. The medical instrument of claim 2, wherein:
each of the repositionable jaws includes a through orifice;
a loop extends through each through orifice to at least partially circumscribe the occlusion clip and a retainer; and,
the retainer is operatively coupled to an occlusion clip deployment control comprising a second of the plurality of controls, where the occlusion clip deployment control is configured to selectively disengage the occlusion clip from the repositionable jaws.

4. The medical instrument of claim 1, wherein:
each link clip is pivotally coupled to the respective link plate, where link plate is repositionably mounted to a pin extending through each link plate; and,
the pin also extends through a clevis that is coupled to the drive cable.

5. The medical instrument of claim 1, wherein:
at least one of the repositionable jaws and the link clips includes a cam;
at least the other of the repositionable jaws and the link clips includes a camming surface engaged by the cam; and,
engagement between the cam and the camming surface allows but limits pivotal motion between a respective repositionable jaw and link clip.

6. The medical instrument of claim 1, wherein:
a respective link clip includes a longitudinal axis extending along a dominant dimension thereof that is substantially coaxial with a longitudinal axis extending along a dominant dimension of the repositionable jaw to which it is pivotally coupled when the repositionable jaws are in a closed position;
the longitudinal axis of a respective link clip is not coaxial with the longitudinal axis of the repositionable jaw to which it is pivotally coupled when the repositionable jaws are in an open position;
the longitudinal axes each extending through a respective repositionable jaw are substantially coaxial in both the open position and the closed position; and,
the closed position has the repositionable jaws closer to one another than when in the open position.

7. The medical instrument of claim 1, wherein:
each link clip coupled to a respective link plate comprises a half scissor connection; and,
each half scissor connection is pivotal about an axle that is operatively coupled to the drive cable.

8. The medical instrument of claim 1, wherein:
a first end of each link clip is repositionably mounted to at least the portion of the second joint;
a second end of each link clip, opposite the first end, is pivotally coupled to at least one of the pair of repositionable jaws; and,
each respective link clip is coupled to a respective link plate between the first and second ends.

9. The medical instrument of claim 1, wherein:
each link clip is pivotally coupled to the second joint; and,
each link plate is pivotally coupled to a respective link clip.

10. A medical instrument comprising:
a controller at least partially housing a plurality of controls;
a first joint including first joint components that are repositionable with respect to one another within a first degree of freedom via a first control of the plurality of controls;
a second joint operatively coupled to the first joint, the second joint including second joint components that are repositionable with respect to one another within a second degree of freedom via a second control of the plurality of controls, the second degree of freedom being different than the first degree of freedom;
an elongated conduit operatively coupling the controller to at least one of the first joint and the second joint; and,
an open-ended occlusion clip end effector operatively coupled to the second joint, the open-ended occlusion clip end effector including jaws repositionable between an open position and a closed position, each of the repositionable jaws repositionably coupled to a respective linkage that is repositionably coupled to at least a portion of the second joint, where the respective linkages are also coupled to one another via a repositionable connection.

11. The medical instrument of claim 10, wherein:
each of the repositionable jaws is pivotally coupled to a respective linkage;
each linkage is pivotally coupled to the portion of the second joint; and,
the respective linkages are pivotally coupled to one another.

12. The medical instrument of claim 10, wherein:
the repositionable connection comprises a first repositionable connection and a second repositionable connection;
each linkage includes a link cavity that receives a portion of the first and second connections; and,
the portion of the second joint includes a connection cavity occupied by at least a portion of the linkages and the first and second connections.

13. The medical instrument of claim 10, wherein:
the repositionable connection comprises a first repositionable connection and a second repositionable connection;
a portion of each linkage interposes respective portions of the second joint; and,
a portion of each connection interposes respective portions of a corresponding linkage.

14. The medical instrument of claim 10, wherein:
the repositionable connection comprises a first repositionable connection and a second repositionable connection;
a first axle concurrently extends through a first of the linkages and through a first portion of the second joint, the first axle fixed in position with respect to at least one of the second joint and the first of the linkages;
a second axle concurrently extends through a second of the linkages and through a second portion of the second joint, the second axle fixed in position with respect to at least one of the second joint and the second of the linkages;
a third axle concurrently extends through the first of the linkages and through a first of the connections, the third axle fixed in position with respect to at least one of the first of the connections and the first of the linkages; and,
a fourth axle concurrently extends through the second of the linkages and through a second of the connections, the fourth axle fixed in position with respect to at least one of the second of the connections and the second of the linkages.

15. The medical instrument of claim 10, wherein:
the repositionable connection comprises a first repositionable connection and a second repositionable connection; and,
a first axle concurrently extends through, and is repositionable with respect to, the first and second repositionable connections.

16. The medical instrument of claim 15, wherein the first axle extends through a pull link, where the pull link is operatively coupled to at least one of the plurality of controls.

* * * * *